United States Patent
Basu et al.

(10) Patent No.: US 7,888,506 B2
(45) Date of Patent: Feb. 15, 2011

(54) COMPOSITION, SYNTHESIS, AND USE OF A NEW CLASS OF FLUOROPHORES

(75) Inventors: Partha Basu, Pittsburgh, PA (US); Barbara Serli Mitasev, Brighton, MA (US)

(73) Assignee: Duquesne University of the Holy Spirit, Pittsburgh, PA (US)

( * ) Notice: Subject to any disclaimer, the term of this patent is extended or adjusted under 35 U.S.C. 154(b) by 116 days.

(21) Appl. No.: 12/020,343

(22) Filed: Jan. 25, 2008

(65) Prior Publication Data

US 2008/0182337 A1 Jul. 31, 2008

Related U.S. Application Data

(60) Provisional application No. 60/897,576, filed on Jan. 26, 2007.

(51) Int. Cl.
C07D 241/36 (2006.01)
G01J 3/30 (2006.01)
G01N 21/76 (2006.01)

(52) U.S. Cl. .................. 544/343; 349/70; 356/317; 436/172

(58) Field of Classification Search .................. None
See application file for complete search history.

(56) References Cited

U.S. PATENT DOCUMENTS

| | | |
|---|---|---|
| 4,997,928 A | 3/1991 | Hobbs, Jr. |
| 5,171,534 A | 12/1992 | Smith et al. |
| 5,332,666 A | 7/1994 | Prober et al. |
| 5,616,790 A | 4/1997 | Arnold et al. |
| 6,977,305 B2 | 12/2005 | Leung et al. |

| | | |
|---|---|---|
| 2006/0092146 A1 | 5/2006 | Johnson et al. |

FOREIGN PATENT DOCUMENTS

WO   WO 94/05688   3/1994

OTHER PUBLICATIONS

Bradshaw et al., "Stable pyrano[2,3-b] quinoxalines and pyrano[2,3-g] pteridines related to molybdopterin", Chemistry Communications, (2001) pp. 123-124 (Bradshaw).*

P.G. Baraldi, et al., "Synthetic studies towards forskolin," *Tetrahedron*, 1989, 45(5), 1517-1532.

C.C.J. Culvenor, et al., "Reactions of ethylene oxides. Part I. Preparation of ethylene sulphides and trithiocarbonates," *J. Chem. Soc.*, 1946, 1050-1052.

C. Schulzke, "Temperature dependent electrochemical investigations of molybdenum and tungsten oxobisdithiolene complexes," *Dalton Trans.*, 2005, 713-720.

(Continued)

*Primary Examiner*—Krishnan S Menon
*Assistant Examiner*—Dirk Bass
(74) *Attorney, Agent, or Firm*—K&L Gates LLP

(57) ABSTRACT

A new class of fluorophores is presented. The fluorophores include a conjugated ring system, such as a dithiolone, a pyran, and a pyrazine containing ring system. The structure is designed with the flexibility to have multiple substitution patterns. The fluorophores may be used in applications including, but not limited to, biomarker applications, pH sensors, metal sensors, and as components for molecular electronics.

7 Claims, 44 Drawing Sheets

OTHER PUBLICATIONS

H. Sugimoto, et al., "Dioxo-Molybdenum(VI) and Mono-oxo-Molybdenum(IV) Complexes Supported by New Aliphatic Dithiolene Ligands: New Models with Weakened Mo=O Bond Characters for the Arsenite Oxidase Active Site," *Inorg. Chem.*, 2005, 44(18), 6386-6392.

B. Bradshaw, et al., "The synthesis of pyrano[2,3-b]quinoxalines related to molybdopterin," *J. Chem. Soc., Perkin Trans. 1*, 2001, 3232-3238.

B. Bradshaw, et al., "Synthesis of a cobalt complex of a pyrano[2,3-b]quinoxaline-3,4-dithiolate related to molybdopterin," *Chem. Commun.*, 1998, 417-418.

M. Ramming, et al., "Diversityand phylogeny of gephyrin: Tissue-specific splice variants, gene structure, and sequence similarities to molybdenum cofactor-synthesizing and cytoskeleton-associated proteins," *Proceedings of the National Academy of Sciences*, 2000, 97(18), 10266-10271.

J.A. Santamaria-Araujo, et al., "The Tetrahydropyranopterin Structure of the Sulfur-free and Metal-free Molybdenum Cofactor Precursor," *J. Biological Chemistry*, 2004, 279(16), 15994-15999.

P. Hanzelmann, et al., "Functionality of Alternative Splice Forms of the First Enzymes Involved in Human Molybdenum Cofactor Biosynthesis," *J. Biological Chemistry*, 2002, 277(21), 18303-18312.

S. Leimkuhler, et al., "In Vitro Incorporation of Nascent Molybdenum Cofactor into Human Sulfite Oxidase," *J. Biological Chemistry*, 2001, 276(3), 1837-1844.

S. Leimkuhler, et al., "A Sulfurtransferase is Required in the Transfer of Cysteine Sulfur in the in Vitro Synthesis of Molybdopterin from Precursor Z in *Escherichia coli*," *J. Biological Chemistry*, 2001, 276(25), 22024-22031.

M. Neumann, et al., "Transfer of the Molybdenum Cofactor Synthesized by *Rhodobacter capsulatus* MoeA to XdhC and MobA," *J. Biological Chemistry*, 2007, 282(39), 28493-28500.

G. Gutzke, et al., "Thiocarboxylation of Molybdopterin Synthase Provides Evidence for the Mechanism of Dithiolene Formation in Metal-binding Pterins," *J. Biological Chemistry*, 2001, 276(39), 36268-36274.

F-A Alphonse et al., "A bis($\eta^5$-cyclopentadienyl)cobalt complex of a bis-dithiolene: a chemical analogue of the metal centres of the DMSO reductase family of molybdenum and tungsten enzymes, in particular ferredoxin aldehyde osidoreductase," *Tetrahedron*, 2005, 614, 11010-11019.

S. Kugler, et al., "Long-Term Rescue of a Lethal Inherited Disease by Adeno-Associated Virus-Mediated Gene Transfer in a Mouse Model of Molybdenum-Cofactor Deficiency," *Am. J. of Human Genetics*, 2007, 80, 291-297.

M. Armengol, et al., "Synthesis of thieno[2,3-b]quinoxalines from 2-haloquinoxalines," *J. Chem. Soc., Perkin Trans. 1*, 2001, 154-158.

B. Bradshaw, et al., "Synthesis of the organic ligand of the molybdenum cofactor, in protected form," *J. Chem. Soc., Perkin Trans. 1*, 2001, 3239-3244.

P.D. Smith, et al., "Detection, Isolation, and Characterization of Intermediates in Oxygen Atom Transfer Reactions in Molybdoenzyme Model Systems," *J. Am. Chem. Soc.*, 2000, 122, 9298-9299.

K. Ushio, et al., "Identification of a Dephosphorylated Oxidation Product of the Molybdenum Cofactor as 2-(1,2-Dihydroethyl)thieno[3,2-g]pterin," *Biochem. and Biophys. Res. Comm.*, 1986, 135(1), 256-261.

A. Matthies et al., "Molybdenum Cofactor Biosyntheis in Humans: Identification of a Persulfide Group in the Rhodanese-like Domain of MOCS3 by Mass Spectroscopy," *Biochemistry*, 2005, 44, 7912-7920.

J.N. Daniels et al., "Crystal Structure of a Molybdopterin Synthase-Precursor Z Complex: Insight into its Sulfur Transfer Mechanism and its Role in Molybdenum Cofactor Deficiency," *Biochemistry*, 2008, 47, 615-626.

L.E. Bevers, et al., "Function of MoaB Proteins in the Biosynthesis of the Molybdenum and Tungsten Cofactors," *Biochemistry*, 2008, 47, 949-956.

S. Goswami et al., "A One-pot Synthesis of Cyclic Pyrido[1,2-a]quinoxaline Phosphate, a New Molecule of Biological Importance from a Quinoxaline Derivative of Sugar," *Chem. Lett.*, 2003, 32(8), 678-679.

B. Bradshaw, et al., "Synthesis of 1,3-dithioI-2-ones as proligands related to molybdopterin," *Org. Biomol. Chem.*, 2003, 1, 129-133.

G. Kaupp, et al., "Quantitative Cascade Condensations between o-Phenylenediamines and 1,2-Dicarbonyl Compounds without Production of Wastes," *Eur. J. Org. Chem.*, 2002, 1368-1373.

S. Goswami, et al., "Molybdenum pentachloride ($MoCl_5$) or molybdenum dichloride dioxide ($MoO_2Cl_2$): advanced catalysts for thioacetalization of heterocyclic, aromatic and aliphatic compounds," *Tet. Lett.*, 2008, 49, 3092-3096.

S. Goswami, et al., "The first microwave-assisted regiospecific synthesis of 6-substituted pterins," *Tet. Lett.*, 2002, 43, 8371-8373.

S. Goswami, et al., "The first synthesis of a cyclic dihydroxyacetone phosphate, a new molecule of biological importance," *Tet. Lett.*, 2002, 43, 503-505.

S. Goswami, "Molybdenum Cofactor: Its Biological Significance, Structural, and Synthetic Aspects," *Heterocycles*, 1993, 35(2), 1551-1570.

A. Sakurai, et al., "Studies on Urothion. Synthesis of (R)-Dephospho Form B, a Degradation Product of the Molybdenum Cofactor," *Heterocyclic Communications*, 1996, 2(4), 383-386.

R.S. Pilato et al., "Model Complexes for Molybdopterin-Containing Enzymes: Preparation and Crystallographic Characterization of a Molybdenum-Ene-1-perthiolate-2-thiolate (Trithiolate) Complex," *J. Am. Chem. Soc.*, 1991, 113, 9372-9374.

E.C. Taylor, et al., "Studies on the Molbdenum Cofactor. An Unequivocal Total Synthesis of (±)-Urothione," *J. Am. Chem. Soc.*, 1989, 1111, 285-291.

B. Fischer, et al., "A chemical approach to systematically designate the pyranopterin centers of molybdenum and tungsten enzymes and synthetic models," *J. Inorg. Biochem.*, 1998, 72, 13-21.

J.D. Schrag, et al., "The Crystal Structure of *Escherichia coli* MoeA, Protein from the Molybdopterin Synthesis Pathway," *J. Mol. Biol.*, 2001, 310, 419-431.

E.C. Taylor, et al., "Model Studies Directed toward the Molybdenum Cofactor: 2-Alkylidene- and 2-(Phenylimino)-1,3-dithioles from Acetylenes," *J. Org. Chem.*, 1991, 56, 1816-1822.

E.C. Taylor, et al., "Studies on the Molybdenum Cofactor: Model Synthetic Routes Directed at Form B," *J. Org. Chem.*, 1988, 53, 5839-5847.

K. Ichida, et al., "A Turkish Case with Molybdenum Cofactor Deficiency," *Nucleosides, Nucleotides, and Nucleic Acids*, 2006, 25, 1087-1091.

L. Larsen, et al., "Model Studies Related to the Cofactor of Oxomolybdoenzymes. Part 3," *J. Chem. Soc. Perkin Trans. 1*, 1989, 2317-2327.

A. Dinsmore, et al., "Synthesis of ($\eta^5$-cyclopentadieny1)-1-(4-benzyloxycarbonyl-3,4-dihydroquinoxalin-2-yl)ethene-1,2-dithiolatocobalt(III) and ($\eta^5$-cyclopentadienyl)-1-[2-(N,N-dimethylaminomethyleneamino)-3-methyl-4-oxopteridin-6-yl]ethene-1,2-dithiolatocobalt(III)," *J. Chem. Soc., Perkin Trans. 1*, 1997, 801-807.

S. Goswami, et al., "Microwave Assisted Improved Synthesis of 6-Formylpterin and Other Heterocyclic Mono- and Di-aldehydes," *Synth. Comm.*, 2003, 33(3), 475-480.

S. Goswami, et al., "A novel one-pot two-component synthesis of tricyclic pyrano[2,3-b]quinoxalines," *Tet. Lett.*, 2005, 46, 221-224.

L. Larsen, et al., "Synthesis of 1-(Quinoxalin-2-yl)-alkane-1,2-dithiols and -alkene-1,2-dithiols of Relevance to the Molybdoenzymes Cofactor, Moco," *Tet. Lett.*, 1988, 29(12), 1453-1456.

A. Dinsmore, et al., "4-(2,2-Dimethyldioxalan-4-yl)-5-(quinoxalin-2-yl)-1,3-dithiol-2-one, a Proligand Relating to the Cofactor of the Oxomolybdoenzymes," *Tetrahedron*, 1998, 54, 3291-3302.

E.C. Taylor et al., "Synthesis of N-{4-[2-(2-Amino-3,4-dihydro-4-oxo-7H-pyrrolo[2,3-d]pyrimidin-5-yl)ethyl]benzoyl}-L-flutamic Acid (LY231514) and Analogues," in Chemistry and Biology of Pteridines and Folates, Proceedings of the 11th International Symposium on Pteridines and Folates, Berchtesgaden, Germany, Jun. 15-20, 1997, Pfleiderer and Rokos, eds., Blackwell Science Publishing, Berlin, 1997, pp. 83-91.

E.S. Davies, et al., "Synthetic Approaches to the Molybdenum Cofactor," in Chemistry and Biology of Pteridines and Folates, Proceedings of the 11th International Symposium on Pteridines and Folates, Berchtesgaden, Germany, Jun. 15-20, 1997, Pfleiderer and Rokos, eds., Blackwell Science Publishing, Berlin, 1997, pp. 693-696.

G. Schwarz, et al., "The Plant Protein Cnx1 Binds Molybdopterin with High Affinity and is Involved in the Last Step of Molybdenum Cofactor Biosynthesis," in Chemistry and Biology of Pteridines and Folates, Proceedings of the 11th International Symposium on Pteridines and Folates, Berchtesgaden, Germany, Jun. 15-20, 1997, Pfleiderer and Rokos, eds., Blackwell Science Publishing, Berlin, 1997, pp. 697-702.

I.S. Heck, et al., "The Product of the Molybdenum Cofactor Gene mob of *Escherichia coli* is a GTP Binding Protein," in Chemistry and Biology of Pteridines and Folates, Proceedings of the 11th International Symposium on Pteridines and Folates, Berchtesgaden, Germany, Jun. 15-20, 1997, Pfleiderer and Rokos, eds., Blackwell Science Publishing, Berlin, 1997, pp. 703-706.

G. Klein, et al., "A fluorescent metal sensor based on macrocyclic chelation," Chem. Commun., 2001, 561-562.

Europe joins R&D forces on Organic LED technology for Lighting Applications (Jan. 31, 2005), available at http://www.physorg.com/news2884.html (last visited Aug. 20, 2008), 2 pages.

Photoluminescence, available at http://en.wikipedia.org/wiki/Photoluminescence (last visited Aug. 20, 2008), 2 pages.

Stokes shift, available at http://en.wikipedia.org/wiki/Stokes_shift (last visited Aug. 20, 2008), 2 pages.

Fluorescence, available at http://en.wikipedia.org/wiki/Fluorescence (last visited Aug. 20, 2008), 8 pages.

"Fluorescent Indicators for $Zn^{2+}$ and Other Metal Ions," The Handbook—A Guide to Fluorescent Probes and Labeling Technologies, Tenth Edition, Section 19.7, Invitrogen, available at http://probes.invitrogen.com/handbook/print/1907.html (last visited Aug. 20, 2008), 8 pages.

"Trace metal sensors for coastal monitoring," An ACT 2005 Workshop Report, A Workshop for Developers, Deliverers, and Users of Technologies for Monitoring Coastal Environments, Workshop Proceedings, Alliance for Coastal Technologies (ACT), Seaside CA, Apr. 11-13, 2005, 27 pages.

\* cited by examiner

Figure 2. Synthetic scheme for the preparation of the different components of fluorophores.

Figure 3. Synthetic schemes for generating a wide variety of fluorophores from compound 5. Note that the thiol group in 11 can be further functionalized for cellular application such as to attach an antibody or other recognition motifs.

Figure 4. Synthetic schemes for generating a wide variety of fluorophores from compound 4

Figure 5. Synthetic schemes for generating a wide variety of fluorophores. Similar compounds shown in Figures 3 and 4 have already been prepared and characterized.

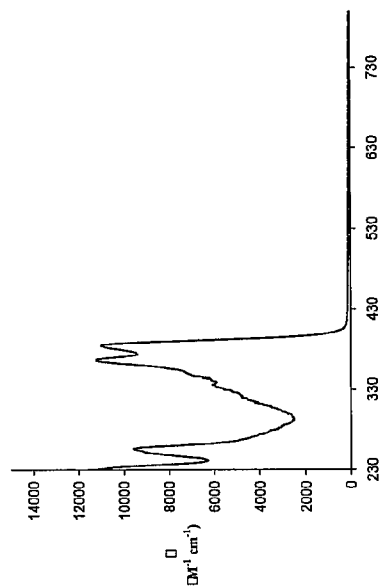
Figure 9. Electronic spectrum of compound 7 in MeOH.
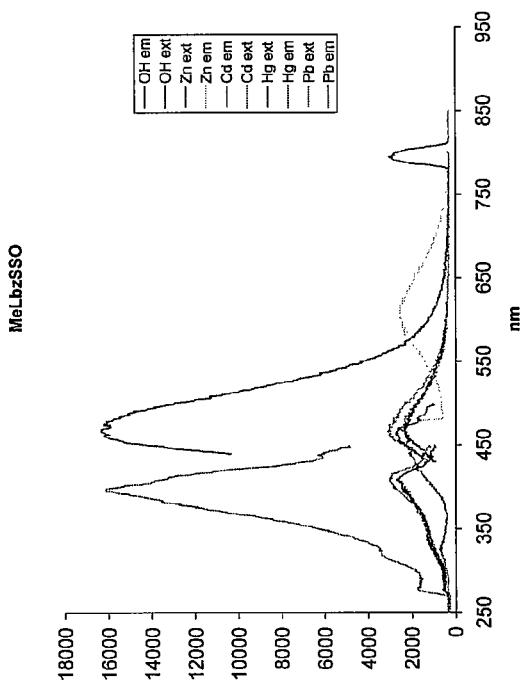
Figure 8. Fluorescence spectra of solutions containing metal ion in question, and compound 7 in the presence of $NH_4OH$.

Figure10. Fluorescence spectrum of compound 7 in the mixed solvent described in the text.

Figure 11. Use of the fluorophores in metal binding.

Fig. 37 Compound 7 (in MeOH)

COMPOSITION, SYNTHESIS, AND USE OF A NEW CLASS OF FLUOROPHORES

CROSS REFERENCE TO RELATED APPLICATIONS

This application claims the priority benefit under 35 U.S.C. §119(e) from U.S. Provisional Application No. 60/897,576, filed Jan. 26, 2007, the disclosure of the entirety of which is incorporated by this reference.

GOVERNMENTAL INTEREST

Portions of this invention was made with Government support under grant GM061555 awarded by the National Institutes of Health. The Government may have certain rights in the invention.

FIELD OF THE TECHNOLOGY

The present invention relates to a new class of fluorescent compounds and their synthesis. Various uses of these new fluorophores are also disclosed.

BACKGROUND

Fluorescent molecules are of great interest because of their potential uses, for example, but not limited to, in labeling and detection of substrates or molecules in cell based assays, as components in organic electronic materials in molecular electronics, as pH sensors, and as metal sensors. There are currently several general classes of fluorescent molecules. These have been divided based on their structural motifs. For example, some common fluorescent structures include xanthene based fluorescein and rhodamine compounds, coumarins, pyrenes, and molecules based on the cyanine dyes. Other common fluorophores include, for example, auramine, acridine orange, dipyrrin, and porphyrin. The basic structures of these common fluorophores are presented in FIG. 1.

Molecular fluorescence is a type of photoilluminescence, which is a chemical phenomenon involving the emission of light from a molecule that has been promoted to an excited state by absorption of electromagnetic radiation. Specifically, fluorescence is a luminescence in which the molecular absorption of a photon triggers the emission of a second photon with a longer wavelength (lower energy) than the absorbed photon. The energy difference between the absorbed photon and the emitted photon results from an internal energy transition of the molecule where the initial excited state (resulting from the energy of the absorbed photon) transitions to a second, lower energy excited state, typically accompanied by dissipation of the energy difference in the form of heat and/or molecular vibration. As the molecule decays from the second excited state to the ground state, a photon of light is emitted from the compound. The emitted photon has an energy equal to the energy difference between the second excited state and the ground state.

Many fluorescent compounds absorb photons having a wavelength in the ultraviolet portion of the electromagnetic spectrum and emit light having a wavelength in the visible portion of the electromagnetic spectrum. However, the absorption characteristics of a fluorophore are dependent on the molecules absorbance curve and Stokes shift (difference in wavelength between the absorbed and emitted photon), and fluorophores may absorb in different portions of the electromagnetic spectrum.

The basic structures of the known fluorophores (FIG. 1) may be modified to provide different excitation and emission profiles. For example, two related compounds, fluorescein and rhodamine have different fluorescent characteristics. Fluorescein absorbs electromagnetic radiation having a wavelength of ~494 nanometers ("nm") and emits light having a wavelength at ~525 nm, in the green region of the visible spectrum, whereas rhodamine B absorbs in radiation having a wavelength of ~510 nm and emits light with an emission maximum of ~570 nm, in the yellow-green region of the visible spectrum. Other fluorophores have different absorption and emission profiles. For example, coumarin-1 absorbs radiation at 360 nm and emits light at ~460 nm (blue light); and pyrene absorbs radiation at ~317 nm and emits light having a wavelength of ~400 nm (violet light).

Despite their versatility, the known fluorophores have a number of disadvantages. For example, the absorption spectra of the fluoroscein class of fluorophores are generally pH sensitive, such that fluorescent yield decreases rapidly at pH levels below 8. Rhodamine and pyrene based fluorescent dyes are hydrophilic and hydrophobic, respectively.

BRIEF SUMMARY

Various embodiments provide for fluorescent compounds. Other embodiments relate to uses of the fluorescent compounds.

In one embodiment, the present disclosure provides a compound having the formula:

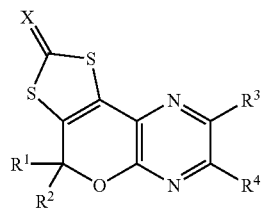

wherein X is selected from the group consisting of O, S, Se, $NR^x$, and $NNHR^x$, wherein $R^x$ is selected from the group consisting of hydrogen, -L—$R^y$, $C_1$-$C_6$ alkyl, phenyl, and substituted phenyl, wherein the phenyl substituents are one or more of fluoro, chloro, bromo, nitro, cyano, $C_1$-$C_6$ alkyl, and $C_1$-$C_6$ alkoxy; $R^1$ and $R^2$ are independently selected from the group consisting of hydrogen, -L—$R^y$, $C_1$-$C_6$ alkyl, amino $C_1$-$C_6$ alkyl, hydroxy $C_1$-$C_6$ alkyl, thio $C_1$-$C_6$ alkyl, carboxy $C_1$-$C_6$ alkyl, halo $C_1$-$C_6$ alkyl, phenyl, substituted phenyl, aryl, substituted aryl, heteroaryl, and substituted heteroaryl, wherein the phenyl, aryl, and heteroaryl substituents are one or more of -L—$R^y$, fluoro, chloro, bromo, nitro, cyano, $C_1$-$C_6$ alkyl, and $C_1$-$C_6$ alkoxy; and $R^3$ and $R^4$ are independently selected from the group consisting of hydrogen, -L—$R^y$, $C_1$-$C_6$ alkyl, amino $C_1$-$C_6$ alkyl, hydroxy $C_1$-$C_6$ alkyl, thio $C_1$-$C_6$ alkyl, carboxy $C_1$-$C_6$ alkyl, halo $C_1$-$C_6$ alkyl, phenyl, substituted phenyl, aryl, substituted aryl, heteroaryl, and substituted heteroaryl, wherein the phenyl, aryl, and heteroaryl substituents are one or more of fluoro, chloro, bromo, nitro, cyano, $C_1$-$C_6$ alkyl, and $C_1$-$C_6$ alkoxy, or $R^3$ and $R^4$ come together to form one of a benzo ring, a substituted benzo ring, a aryl ring, a substituted aryl ring, a heteroaryl ring, and a substituted heteroaryl ring, wherein the benzo, aryl, and heteroaryl substituents are one or more of -L—$R^y$, fluoro, chloro, bromo, nitro, $C_1$-$C_6$ alkyl, amino $C_1$-$C_6$ alkyl, hydroxy $C_1$-$C_6$ alkyl, thio $C_1$-$C_6$ alkyl, carboxy $C_1$-$C_6$ alkyl, halo $C_1$-$C_6$ alkyl, and $C_1$-$C_6$ alkoxy.

Other embodiments relate to a method of marking a substrate, such as a biomolecule, comprising reacting a compound having a formula as described herein with a substrate.

Still other embodiments provide for a method of detecting a metal ion comprising forming a complex between a metal ion and a fluorophore having a formula as described herein; and measuring an fluorescence emission spectrum of the complex.

Further embodiments provide for a method of measuring a pH of a solution comprising measuring an fluorescence emission spectrum of a solution containing a fluorophore having a formula as described herein.

Still further embodiments provide for an electronic device comprising a compound having a formula as described herein.

BRIEF DESCRIPTION OF THE DRAWINGS

The various embodiments of the present disclosure will be better understood when read with reference to the following figures.

FIG. 8 illustrates the fluorescence emission spectra of metal/fluorophore complexes according to certain embodiments of the present disclosure.

FIG. 9 illustrates the electromagnetic absorption spectrum in methanol of a fluorophore according to the present disclosure.

DETAILED DESCRIPTION

Figure 1:
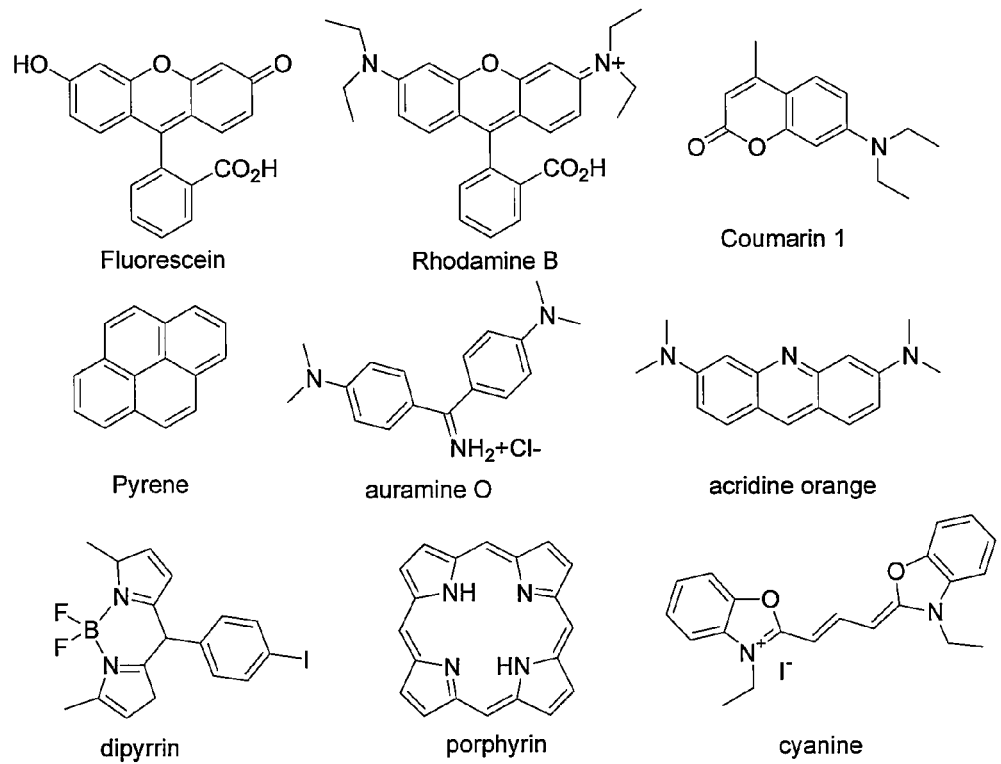
FIG. 1 illustrates various fluorescent molecules known in the prior art.

The present disclosure relates to a new class of fluorophores that may be synthesized from readily available materials. The structure of the fluorophore is designed with the flexibility to have multiple substitution patterns. Various uses of the fluorophores, including for example, as molecular markers, pH sensors, organic electric materials in molecular electronics, and metal binders/sensors, are also disclosed.

Other than the operating examples, or where otherwise indicated, all numbers expressing quantities of ingredients, processing conditions and the like used in the specification and claims are to be understood as being modified in all instances by the term "about". Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical values, however, may contain certain errors, such as, for example, equipment and/or operator error, necessarily resulting from the standard deviation found in their respective testing measurements.

Also, it should be understood that any numerical range recited herein is intended to include all sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of less than or equal to 10.

Any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The present disclosure describes several different features and aspects of the invention with reference to various exemplary non-limiting embodiments. It is understood, however, that the invention embraces numerous alternative embodiments, which may be accomplished by combining any of the different features, aspects, and embodiments described herein in any combination that one of ordinary skill in the art would find useful.

The present disclosure relates to the development of a new class of fluorophores having a structure comprising at least three fused rings including a five membered ring containing an ene-dithiolate moiety, a six-membered pyran ring, and a six-membered pyrazine ring. The general structure of the new class of fluorophores is represented by formula I.

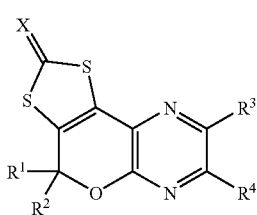

I

In formula I, X represents a group such as 0 (i.e., a carbonyl, a "dithiolone"), S (i.e., a thiocarbonyl), Se (i.e., a selenocarbonyl), $NR^x$ (i.e., an imine), $NR^x_2{}^+$ (an iminium ion), or $NNHR^x$ (a hydrazine). Each $R^x$ may independently be a group such as hydrogen, the group -L—$R^y$, $C_1$-$C_6$ alkyl, phenyl, and substituted phenyl. The substituted phenyl may have from 1 to 5 substituents where each substituent may independently be one or more of the group -L—$R^y$, a fluoro, chloro, bromo, nitro, cyano, hydroxy, amino, thiol, $C_1$-$C_6$ alkyl, and $C_1$-$C_6$ alkoxy. As used herein, the term "$C_1$-$C_6$ alkyl" means an alkyl substituent having from 1 to 6 carbon atoms arranged either as a linear chain or as a branched chain. As used herein, the term "$C_1$-$C_6$ alkoxy" means an alkoxy substituent having from 1 to 6 carbon atoms arranged either as a linear chain or as a branched chain and attached via an ether linkage.

Further, in formula I, $R^1$ and $R^2$ may each independently be hydrogen, the group -L—$R^y$, $C_1$-$C_6$ alkyl, amino $C_1$-$C_6$ alkyl, hydroxy $C_1$-$C_6$ alkyl, thio $C_1$-$C_6$ alkyl, carboxyl $C_1$-$C_6$ alkyl, halo $C_1$-$C_6$ alkyl phenyl, substituted phenyl, aryl, substituted aryl, heteroaryl, or substituted heteroaryl. The substituted phenyl, aryl, or heteroaryl may have from 1 to 5 substituents where each substituent may be one or more of fluoro, chloro, bromo, nitro, cyano, hydroxy, amino, thiol, $C_1$-$C_6$ alkyl, amino $C_1$-$C_6$ alkyl, hydroxy $C_1$-$C_6$ alkyl, thio $C_1$-$C_6$ alkyl, carboxyl $C_1$-$C_6$ alkyl, halo $C_1$-$C_6$ alkyl, and $C_1$-$C_6$ alkoxy. As used herein, the terms "aryl" or "aryl ring" include an aromatic ring (i.e., a single aromatic ring) or ring system (i.e., a polycyclic aromatic ring system) in which all ring atoms are carbon. As used herein, the terms "heteroaryl" or "heteroaryl ring" include an aromatic ring (i.e., a single aromatic ring) or ring system (i.e., a polycyclic aromatic ring system) in which at least one of the ring atoms is a heteroatom, such as nitrogen, oxygen or sulfur heteroatom.

In formula I, $R^3$ and $R^4$ may independently be the group -L—$R^y$, hydrogen, $C_1$-$C_6$ alkyl, amino $C_1$-$C_6$ alkyl, hydroxy $C_1$-$C_6$ alkyl, thio $C_1$-$C_6$ alkyl, carboxy $C_1$-$C_6$ alkyl, halo $C_1$-$C_6$ alkyl, phenyl, substituted phenyl, aryl, substituted aryl, heteroaryl, or substituted heteroaryl. The substituted phenyl, aryl, or heteroaryl may have from 1 to 5 substituents where each substituent may be one or more of a fluoro, chloro, bromo, nitro, cyano, hydroxy, amino, thiol, $C_1$-$C_6$ alkyl, amino $C_1$-$C_6$ alkyl, hydroxy $C_1$-$C_6$ alkyl, thio $C_1$-$C_6$ alkyl, carboxy $C_1$-$C_6$ alkyl, halo $C_1$-$C_6$ alkyl, and $C_1$-$C_6$ alkoxy. Alternatively in certain embodiments, $R^3$ and $R^4$ may come together to form one of a benzo ring, a substituted benzo ring, an aryl ring, a substituted aryl ring, a heteroaryl ring, or a substituted heteroaryl ring. The substituted benzo, substituted aryl, or substituted heteroaryl ring(s) may have from 1 to 4 substituents where each substituent may be one or more of the group -L—$R^y$, a fluoro, chloro, bromo, nitro, cyano, hydroxy, amino, thiol, $C_1$-$C_6$ alkyl, amino $C_1$-$C_6$ alkyl, hydroxy $C_1$-$C_6$ alkyl, thio $C_1$-$C_6$ alkyl, carboxy $C_1$-$C_6$ alkyl, halo $C_1$-$C_6$ alkyl, and $C_1$-$C_6$ alkoxy.

For example, according to certain embodiments, the fluorophores of the present disclosure may have a structure as represented by formula II.

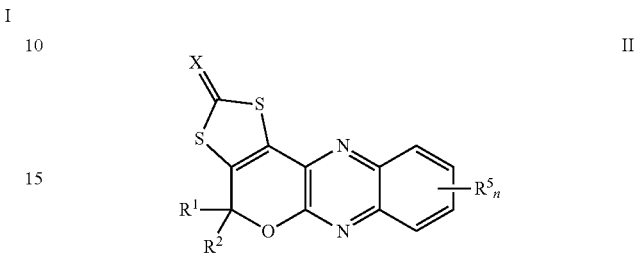

II wherein X, $R^1$ and $R^2$ are as set forth above and $R^3$ and $R^4$ come together to form a benzo ring or substituted benzo ring, wherein n is an integer from 0 to 4 and each $R^5$ is independently a substituent such as, for example, the group -L—$R^y$, fluoro, chloro, bromo, nitro, cyano, hydroxy, amino, thiol, $C_1$-$C_6$ alkyl, hydroxy $C_1$-$C_6$ alkyl, amino $C_1$-$C_6$ alkyl, thio $C_1$-$C_6$ alkyl, carboxyl $C_1$-$C_6$ alkyl, halo $C_1$-$C_6$ alkyl, or $C_1$-$C_6$ alkoxy, or two or more $R^5$ groups come together to form at least one other aromatic ring or heteroaromatic ring (i.e., a aryl ring or heteroaryl ring, respectively).

According to other embodiments, $R^3$ and $R^4$ may come together to form a heteroaryl ring or substituted heteroaryl ring, such as a nitrogen containing heteroaromatic ring as shown in formula III. As shown in formula III, each Y in the ring may be either a N or a C, provided that at least one Y is N.

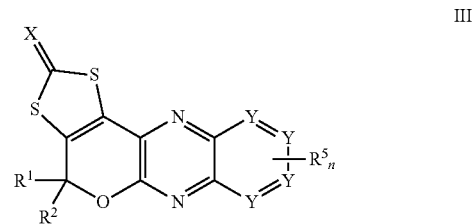

III

Examples of heteroaryl and substituted heteroaryl rings include, but are not limited to, for example, pyridyl, pyrimidyl, pyrazyl, pyridazyl, uracil, thiouracil (2-thiouracil or 4-thiouracil), pyrimidonyl, and the like. With reference to formula III, the groups X, $R^1$, $R^2$, and $R^5$ may be as described herein and integer n may range from 0 to 3. As will be understood by one having ordinary skill in the art with reference to the synthetic procedures set forth herein, a wide variety of aryl, substituted aryl, heteroaryl and substituted heteroaryl ring structures may be fused to the pyrazine ring of formula I.

According to the various embodiments, the fluorophores of the present disclosure exhibit fluorescence. That is, the fluorophores of the present disclosure absorb electromagnetic radiation. Upon absorption of the electromagnetic radiation, the frontier electron (for single electron excitation) of the fluorophores is promoted to an excited electronic state which then decays to a second excited electronic state concomitant with molecular vibration and/or the release of heat. The fluorophores decay from the second excited state to the ground electronic state with the emission of electromagnetic radiation, wherein the emitted electromagnetic radiation has a wavelength that is longer than the wavelength of the absorbed radiation. For example, certain embodiments of the fluorophores having the structures set forth herein may absorb electromagnetic radiation having a wavelength within the ultraviolet region of the electromagnetic spectrum and fluoresce, that is emit electromagnetic radiation, at a wavelength within the blue light region of the visible spectrum. In certain embodiments, the fluorophores of the present disclosure may fluoresce with an emission maximum at a wavelength within the ultraviolet or visible regions of the electromagnetic spectrum. According to certain embodiments, the fluorophores of the present disclosure may fluoresce with an emission maximum at a wavelength from 200 nm to 850 nm. According to other embodiments, the emission maximum may be at a wavelength from 300 nm to 600 nm. According to other embodiments, the emission maximum may be at a wavelength from 400 nm to 500 nm. As used herein, the term "emission maximum" means the wavelength of the greatest intensity within the fluorescence spectrum of a fluorophore.

Without intending to be limited by any theory or interpretation, it is believed by the inventors that the fluorescent character of the core structure of the fluorophores disclosed herein may depend on and may be manipulated by changing the nature of the conjugated pi system of the fluorophore, the atoms present in the fluorophore, and/or the substituents attached to the fluorophore. As used herein, the term "fluorescent character" includes such characteristics of the fluorophore, such as, but not limited to, the wavelength of light absorbed, the wavelength of the fluorescence emission, the fluorescence intensity, and the quantum yield. Thus, the fluorescent character of the fluorophores of the present disclosure may be affected by changing one or more of the nature of the pi system of the fluorophore, the atoms in the fluorophore, or the substitution pattern on the fluorophore.

Changes in the conjugated pi system of the fluorophore having formula I may be affected, for example, by extending the conjugated pi system of the fluorophore, such as by fusing a benzo group (substituted or unsubstituted), an aryl group (substituted or unsubstituted), or a heteroaryl group (substituted or unsubstituted) to the pyrazine ring of the fluorophore (for example, but not limited to, as set forth in formula II or III). Alternatively, or additionally, the conjugated pi system of the fluorophore may be extended by attaching a conjugation extending substituent to the pyrazine ring or an aromatic or heteroaromatic ring fused to the pyrazine ring. The aromatic or heteroaromatic ring may be fused directly to the pyrazine ring (that is the rings share two common atoms) or fused indirectly to the pyrazine ring (that is the aromatic or heteroaromatic ring may be fused to an aromatic or heteroaromatic ring that is fused (directly or indirectly) to the pyrazine ring. For example, attaching a substituent, such as an electron withdrawing group or an electron donating group, directly to the pyrazine ring or aromatic ring would alter the electronic nature of the conjugated pi system of the fluorophore. As used herein, the term "electron withdrawing group" means a substituent which withdraws electron density from the fluorophore. As used herein, the term "electron donating group" means a substituent that donates electron density into the fluorophore. Altering the conjugated pi system of the fluorophore, such as, by extending the pi system and/or attaching an electron donating group or electron withdrawing group may change the fluorescent character of the fluorophore, such as, by changing the wavelength of light absorbed and/or emitted or changing the fluorescent quantum yield. As used herein, the term "fluorescence quantum yield" is a measurement of the efficiency of the fluorescence process and is defined by the ratio of the number of photons emitted to the number of photons absorbed by the fluorophore.

Changing the atoms on the fluorophore skeleton may also change the fluorescence characteristics of the fluorophore. For example, and with reference to formula I, changing the nature of X may affect the fluorescence characteristics of the fluorophore. That is, a fluorophore having formula I wherein X is O may have a different fluorescence character than a fluorophore having structure I wherein X is S, Se, $NR^x$, $NR^x_2{}^+$, or $NNHR^x$. Thus, each different X group may affect the fluorescence characteristics differently.

In addition, changing the substitution pattern on the fluorophore may also change the fluorescence characteristics of the fluorophore. For example, as set forth herein, attaching a substituent, such as, an electron donating group or an electron withdrawing group may affect the fluorophore and therefore change the fluorescence characteristics of the fluorophore. Alternatively, or in addition, changing the substitution pattern on the fluorophore may also include changing the nature of the substituent $R^1$ and/or $R^2$. For example, changes in the nature of the substituent at $R^1$ and/or $R^2$ may affect the energy of the excited state of the fluorophore, the wavelength of radiation absorbed or emitted, and/or the fluorescent quantum yield. In addition, changing the position of one or more substituent on the ring system of the fluorophore (i.e., changing the ring atom that the one or more substituent is bonded to) may change the fluorescence characteristics of the fluorophore.

According to certain embodiments of the present disclosure, the fluorophores may be used as a molecular probe, such as a biological probe. According to certain embodiments, the fluorophore may be modified with a reactive group that can react with and form a bond to a compound or substrate of interest (i.e., the molecule or substrate to be probed). The product of the chemical reaction between the fluorophore and the compound or substrate of interest will then fluoresce. For example, according to certain embodiments, the fluorophores may contain at least one group -L—$R^y$, wherein $R^y$ is a reactive group that is attached to the fluorophore by a covalent linkage L. Covalent linkage L may be attached to the skeleton of the fluorophore, for example as substituent $R^1$, $R^2$, and/or $R^5$ or any other available covalent attachment site (such as, for example, $R^x$) on the skeleton (as shown in formulae, I, II, and III). According to certain embodiments, the covalent linkage attaching the fluorophore to $R^y$ may contain multiple intervening atoms that may serve as a spacer, for example an alkylene glycol spacer such as a polyalkylene glycol spacer.

Fluorophores of the present disclosure with one or more reactive groups $R^y$ may label a wide variety of organic or inorganic substances that contain or may be modified to contain functional groups with suitable reactivity to react with reactive group $R^y$. The resulting reaction product may be represented by the formula F-L-Sub, where F represents the fluorophore core, L is the linkage group and Sub indicates the substrate that the fluorophore is now bound to (by the residue of reactive group $R^y$). As used herein, the term "reactive group" means any moiety on the structure L—$R^y$ that is capable of reacting chemically with a functional group on a different compound (i.e., the substrate of interest) to form a covalent or ionic linkage. Examples of suitable reactive groups include electrophiles or nucleophiles that can form a covalent linkage by reaction with a corresponding nucleophile or electrophile, respectively, on the substrate of interest. Non-limiting examples of suitable electrophilic reactive groups may include, for example, esters including activated esters (such as, for example, succinimidyl esters), amides, acrylamides, acyl azides, acyl halides, acyl nitriles, aldehydes, ketones, alkyl halides, alkyl sulfonates, anhydrides, aryl halides, aziridines, boronates, carbodiimides, diazoalkanes, epoxides, haloacetamides, haloplatinates, halotriazines, imido esters, isocyanates, isothiocyanates, maleimides, phosphoramidites, silyl halides, sulfonate esters, sulfonyl halides, and the like. Non-limiting examples of suitable nucleophilic reactive groups may include, for example, amines, anilines, thiols, alcohols, phenols, hyrazines, hydroxylamines, carboxylic acids, glycols, heterocycles, and the like.

The covalent linkage L binds the reactive group $R^y$ or the reacted group Sub to the fluorophore, either directly (when L is a single bond) or with a combination of stable chemical bonds, for example, single, double, triple, or aromatic carbon-carbon bonds, carbon-nitrogen bonds, carbon-oxygen bonds, carbon-sulfur bonds, nitrogen-nitrogen bonds, phosphorus-oxygen bonds, phosphorus-nitrogen bonds, and nitrogen-platinum bonds. L may include, for example, ether, alkyl, alkylene glycol, polyalkylene glycol, thioether, carboxamide, sulfonamide, urea, urethane, phosphate ester, and hyrdrazine moieties, including combination of any thereof.

The choice of the reactive group $R^y$, used to attach the fluorophore to the substrate, typically depends on the functionality of the substrate and the type of linkage desired. The types of functionality typically present in organic or inorganic substrates of interest include, but are not limited to, amines, amides, thiols, alcohols, phenols, aldehydes, ketones, phosphates, imidazoles, hydrazines, hydroxylamines, disubstituted amines, halides, epoxides, carboxylate esters, sulfonate esters, purines, pyrimidines, carboxylic acids, olefinic bonds, or a combination of these functionalities. A single type of reactive functionality may be present on a substrate, such as the hydroxyl group on a sugar, or alternatively, multiple different reactive functionality may be present on the substrate (such as with a protein or nucleotide).

According to various embodiments, the fluorophores may be used to bond to or label a variety of organic or inorganic substrates, thereby forming a fluorescent labeled product. For example, according to certain embodiments, the fluorophores may have a reactive group $R^y$ suitable for reacting with a biological monomer or polymer, such as, an amino acid, a peptide, a protein, an enzyme, an enzymatic substrate, an antibody, a nucleic acid base, a nucleoside, an oligonucleotide, or a nucleic acid polymer (single or double stranded). As used herein, the term "enzymatic substrate" includes molecules or compounds capable of binding to an enzyme, for example at the active site of the enzyme or another binding site on the enzyme.

According to certain embodiments, the fluorophore, such as a fluorophore with a reactive group thereon may be reacted with an amino acid or peptide chain to give, respectively, a fluorophore labeled amino acid or peptide chain. The fluorophore labeled amino acid or peptide chain may then be incorporated into a larger peptide or protein chain. In another embodiment, the fluorophore and reactive group thereon may be reacted with a nucleic acid base or nucleoside to give, respectively, a fluorophore labeled nucleic acid base or nucleoside. The fluorophore labeled nucleic acid base or nucleoside may then be incorporated into a larger oligonucleotide or nucleic acid polymer.

For example, according to one embodiment, the fluorophore may be incorporated or bonded to an enzymatic substrate or an antibody to give a fluorescent enzymatic substrate or antibody. The fluorescent enzymatic substrate or antibody may then bind to specific enzymes or antigens, respectively, providing fluorescent labeled enzymes or antigens. In another embodiment, the fluorophore may be incorporated or bonded to a nucleoside which may then be incorporated into a nucleic acid strand to provide a fluorescent labeled nucleic acid.

Various embodiments of the fluorophores disclosed herein may be used according to methods extensively known in the art, such as, use of antibody/protein conjugates in microscopy and immunofluorescent assays or as nucleotide or oligonucleotide conjugates for nucleic acid hybridization assays and nucleic acid sequencing, such as those disclosed in U.S. Pat. Nos. 5,332,666, 5,171,534, 4,997,928, and WO Application 94/05688, the disclosures of each are hereby incorporated in their entirety by reference.

For example, once a substrate has been labeled by the fluorophore according to various embodiments disclosed herein, the fluorescence emission spectrum of the fluorescent labeled product may be measured. For example, according to certain embodiments, the intensity of the fluorescence emission spectrum may be determined and may be quantitatively correlated to the concentration of labeled product in the composition. In other embodiments, the fluorescence emission spectrum of the fluorescent labeled product may be taken and qualitatively used to determine the presence of labeled product and therefore used to determine the presence of the target molecule (i.e., the substrate) in the composition.

Figure 11:
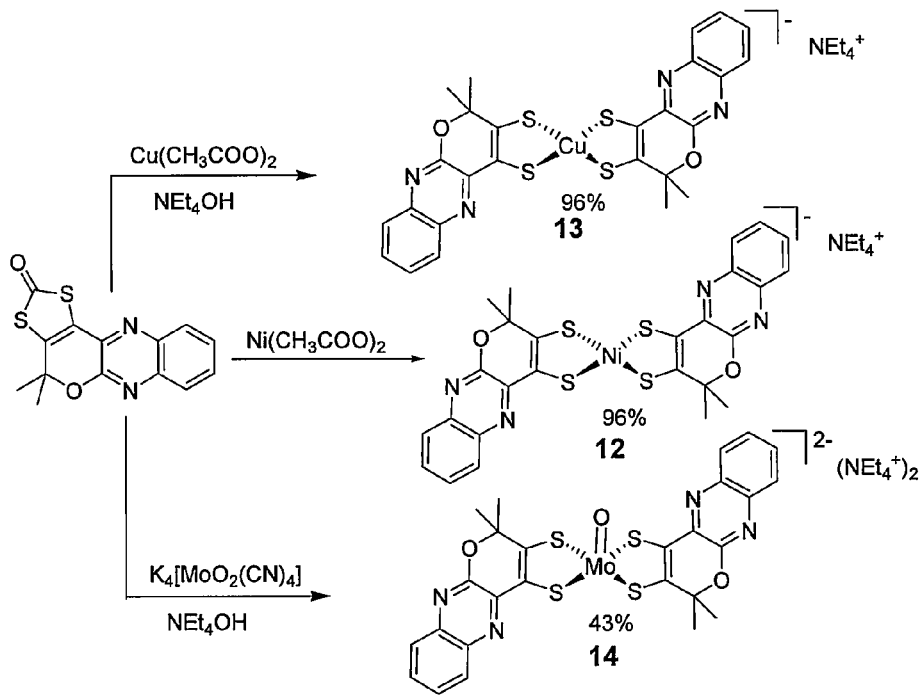
FIG. 11 illustrates the structure of the complexes formed between certain metal ions and a fluorophore according to one embodiment of the present disclosure.
Figure 12:
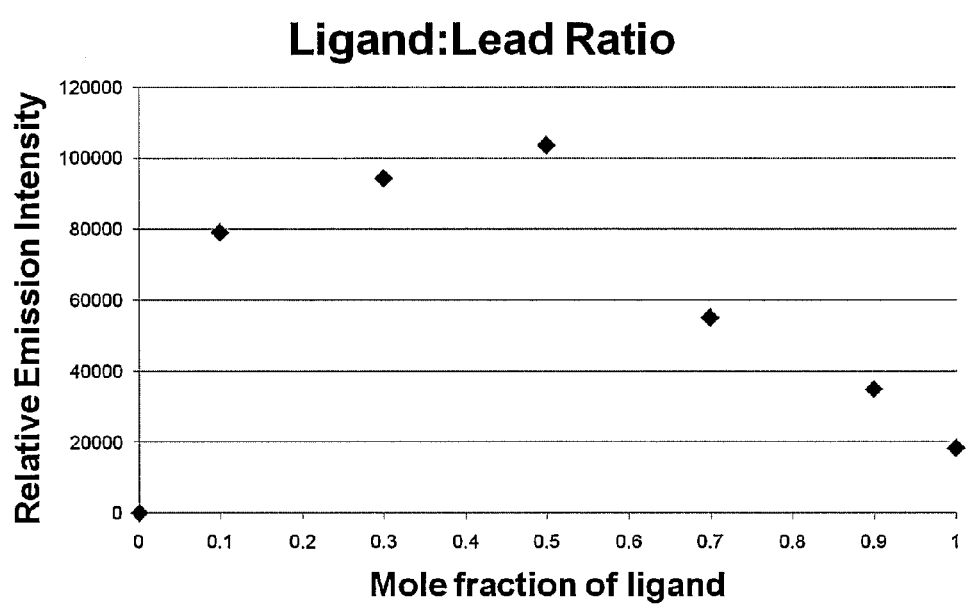
FIG. 12 illustrates a plot of the intensity of the fluorescence emission spectrum relative to ligand/metal complex ratio.
Figure 13:
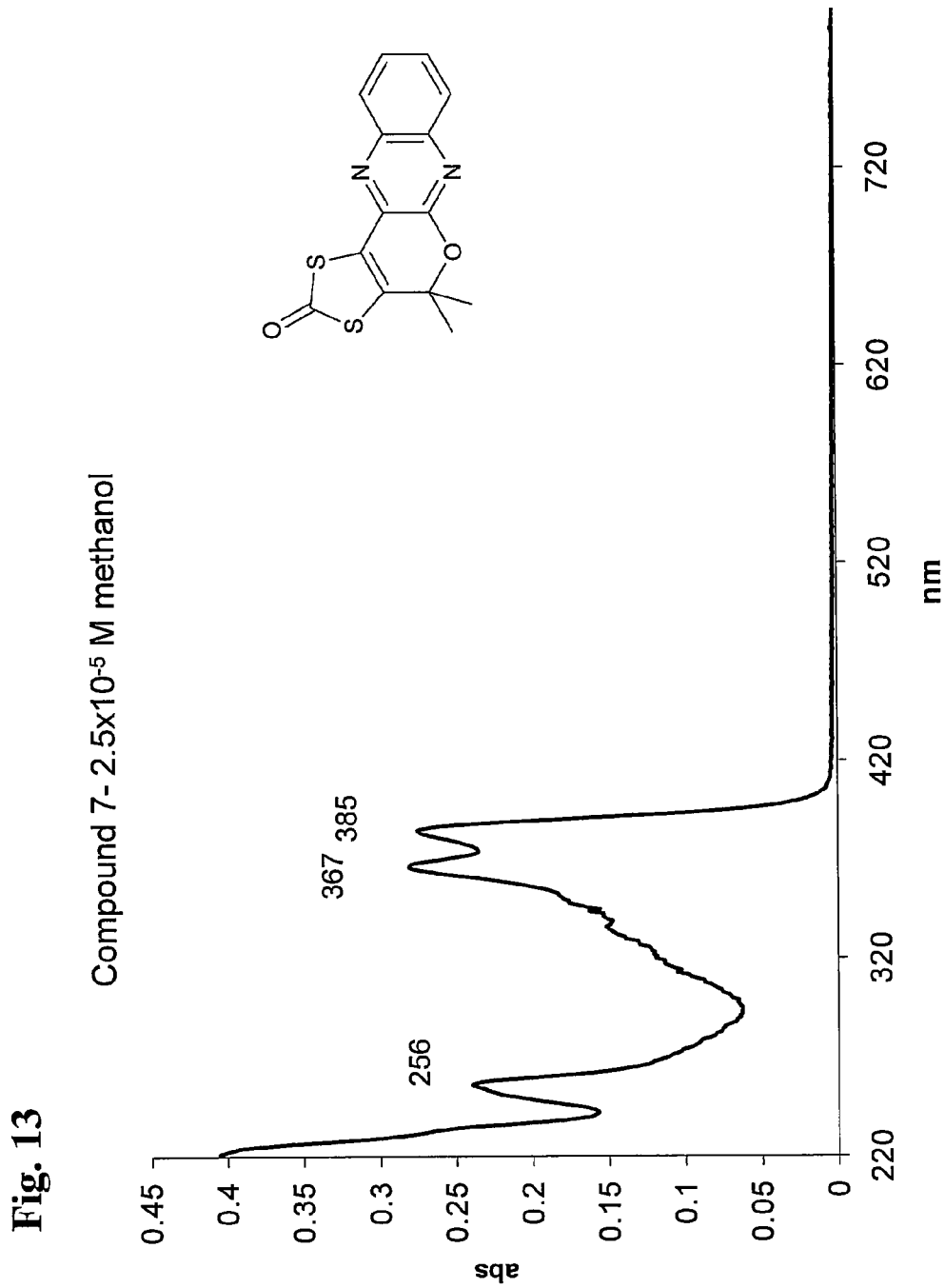
FIGS. 13-14 illustrate electronic spectra and excitation and emission spectra of one fluorophore of the present disclosure in methanol.
Figure 14:
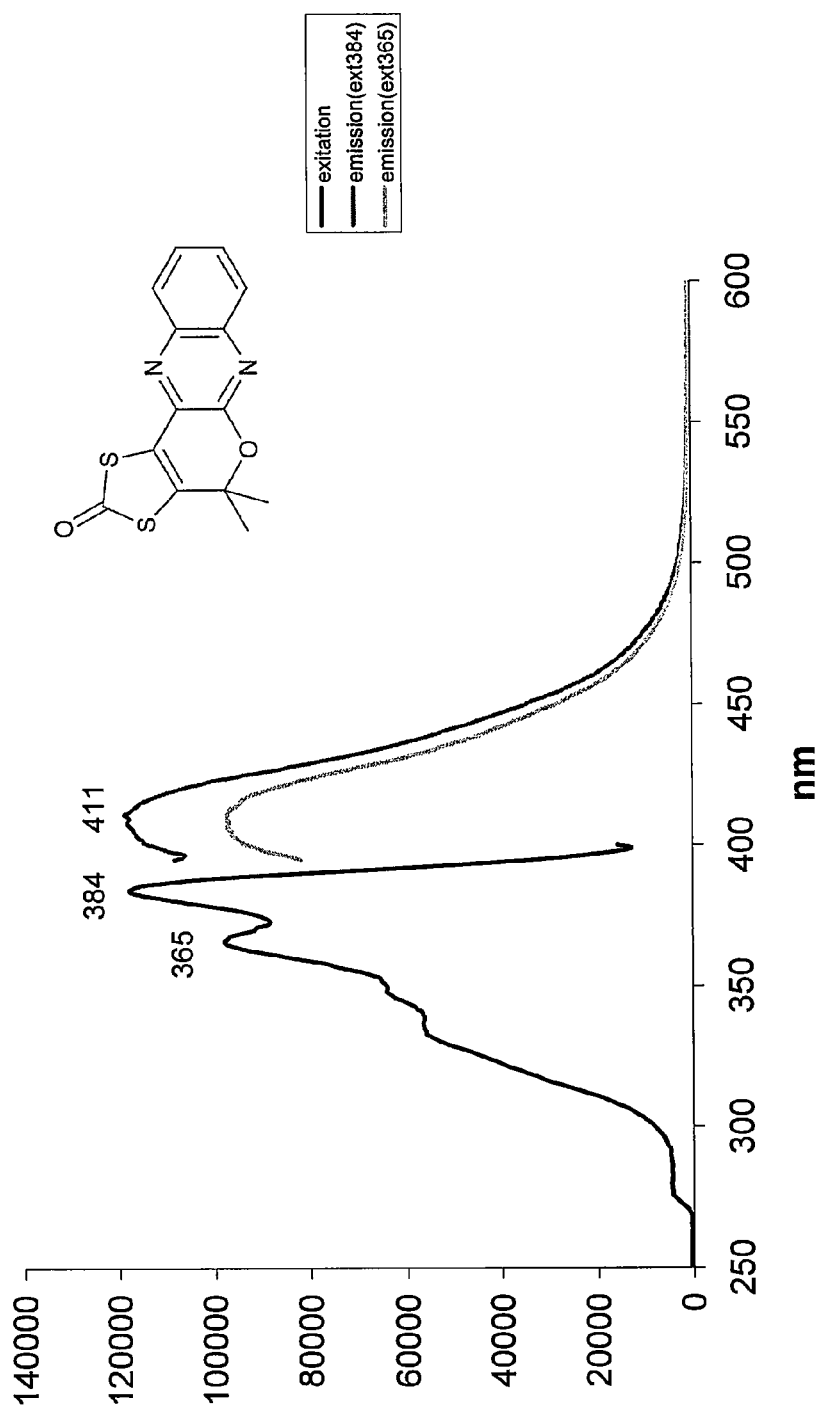
Figure 15:
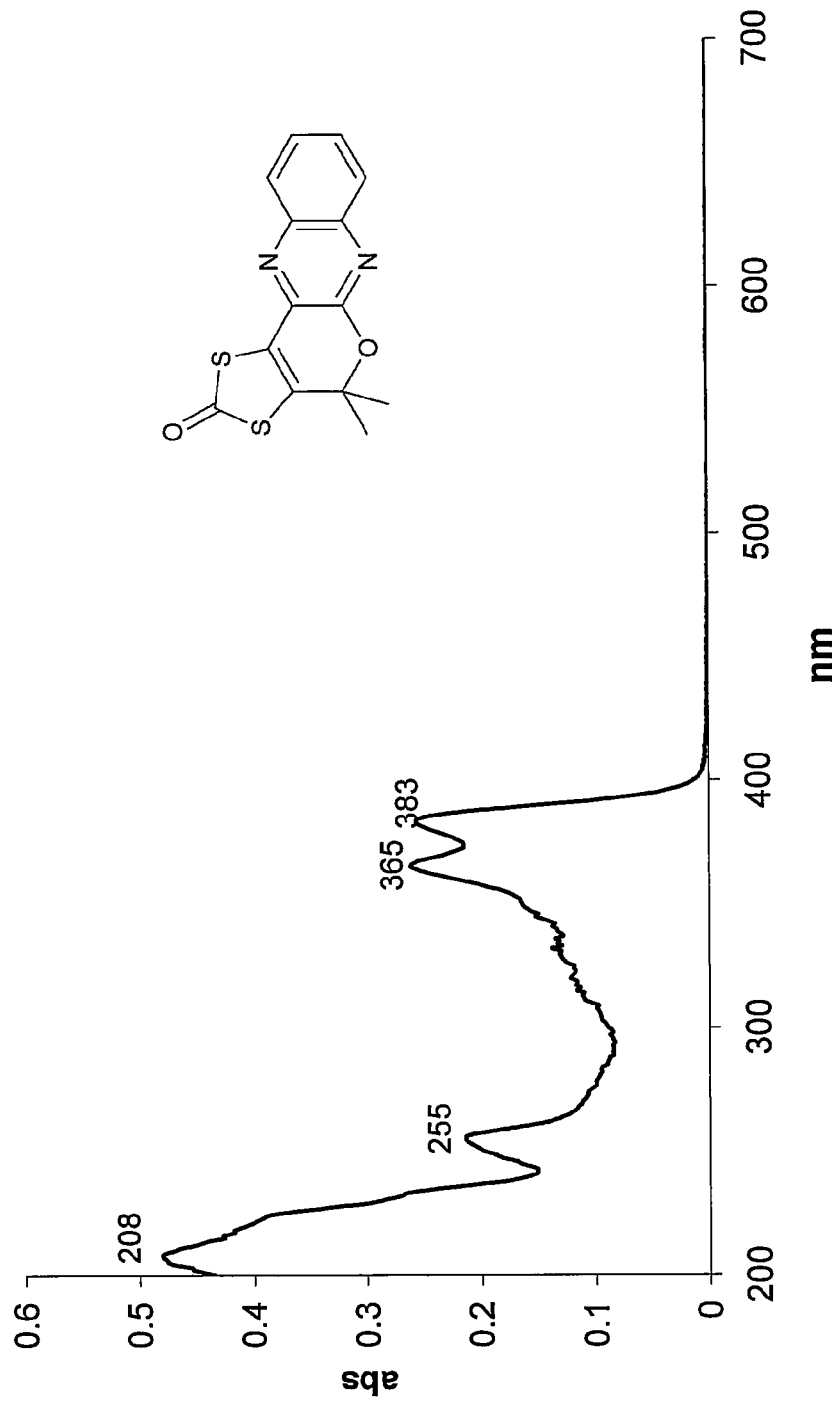
FIGS. 15-18 illustrate electronic spectra and excitation and emission spectra of one fluorophore of the present disclosure in acetonitrile.
Figure 16:
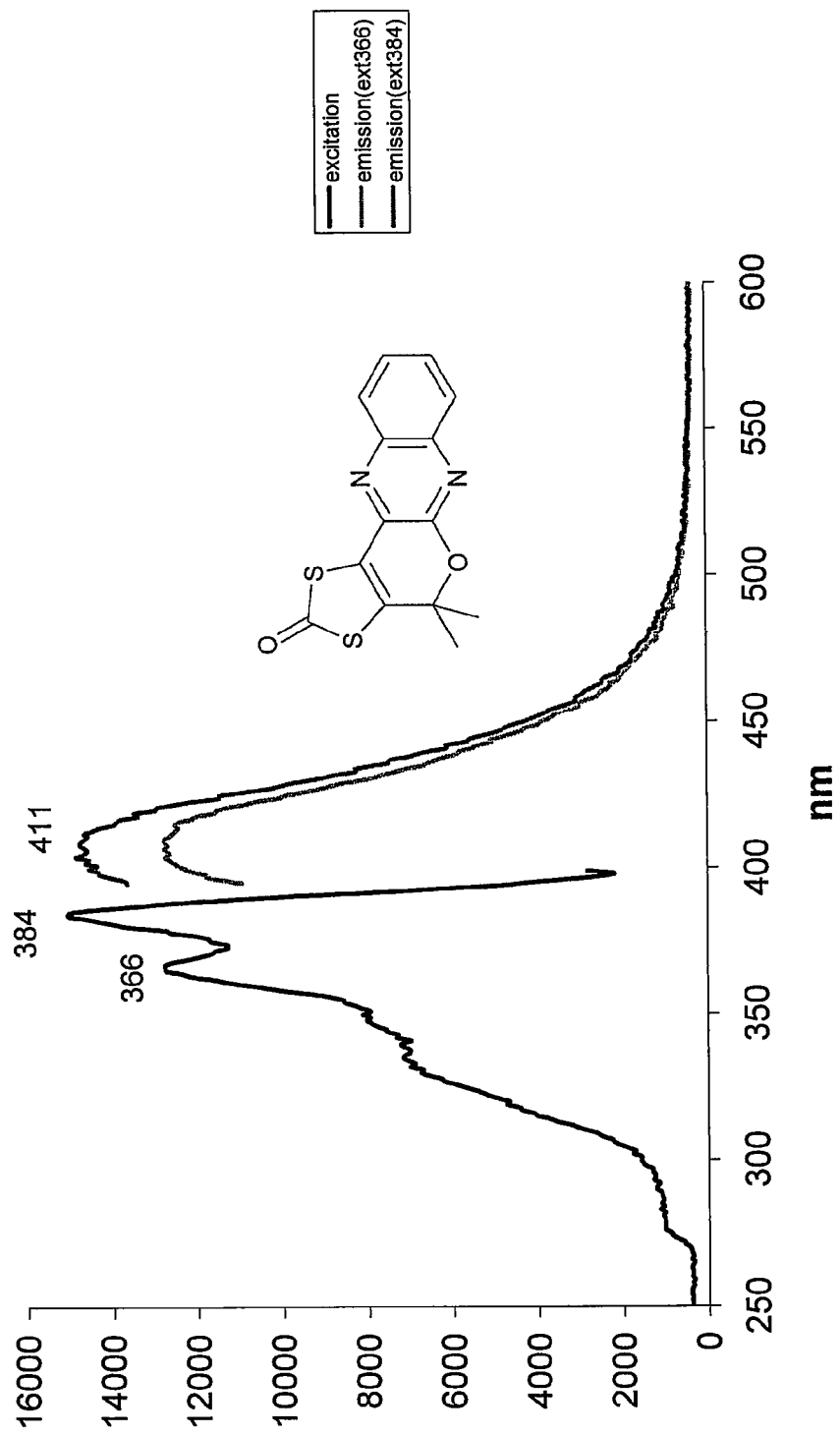
Figure 17:
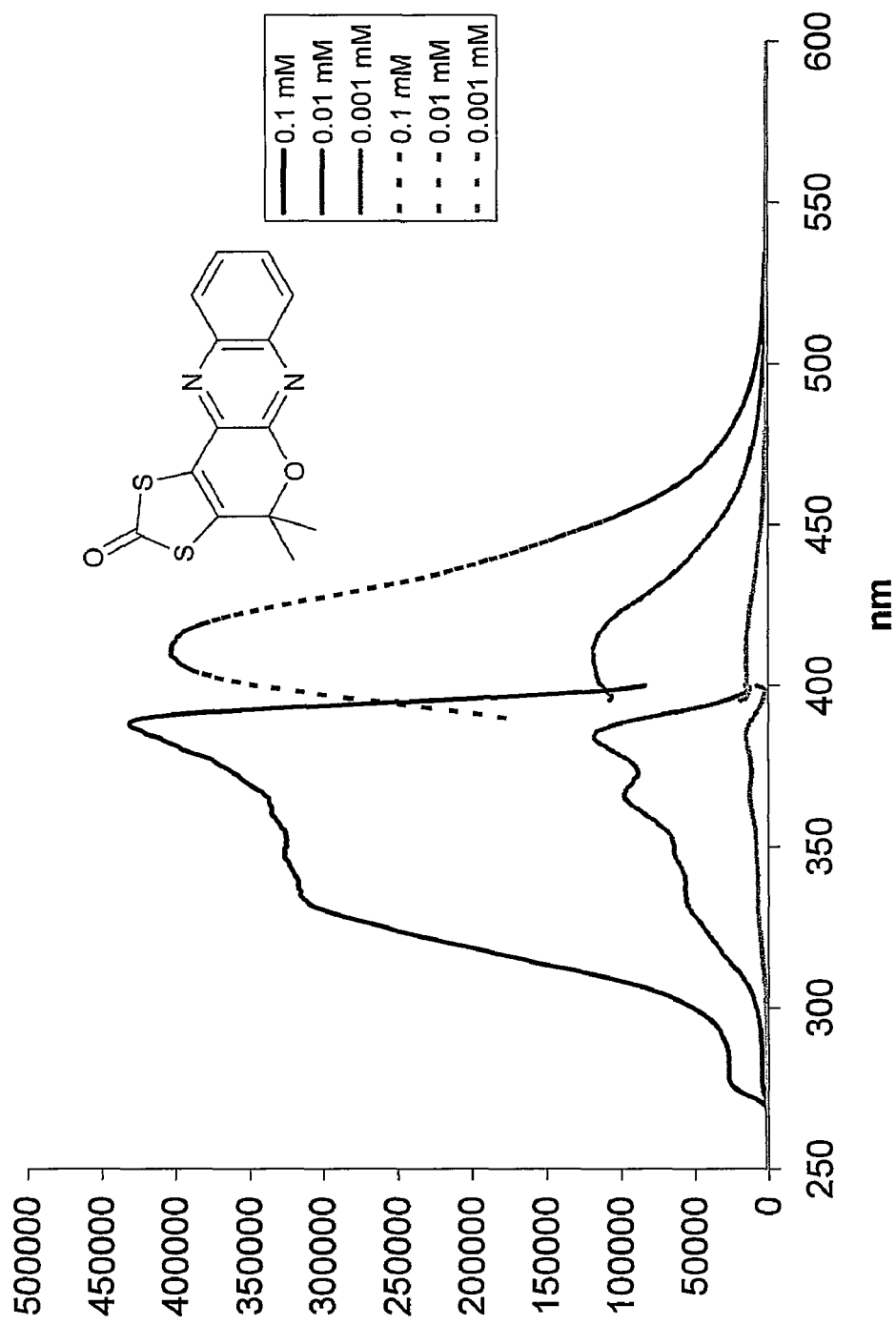
Figure 18:
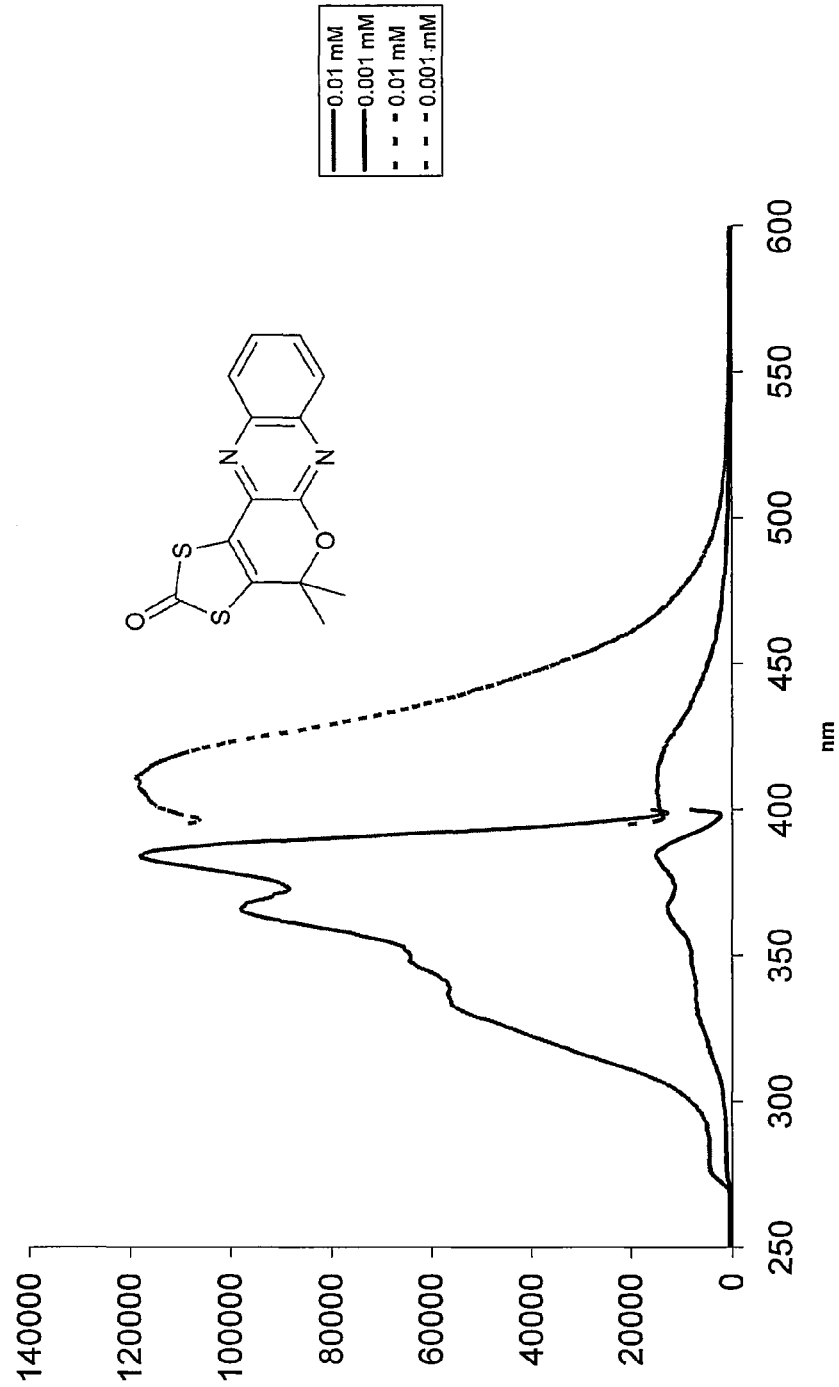
Figure 19:
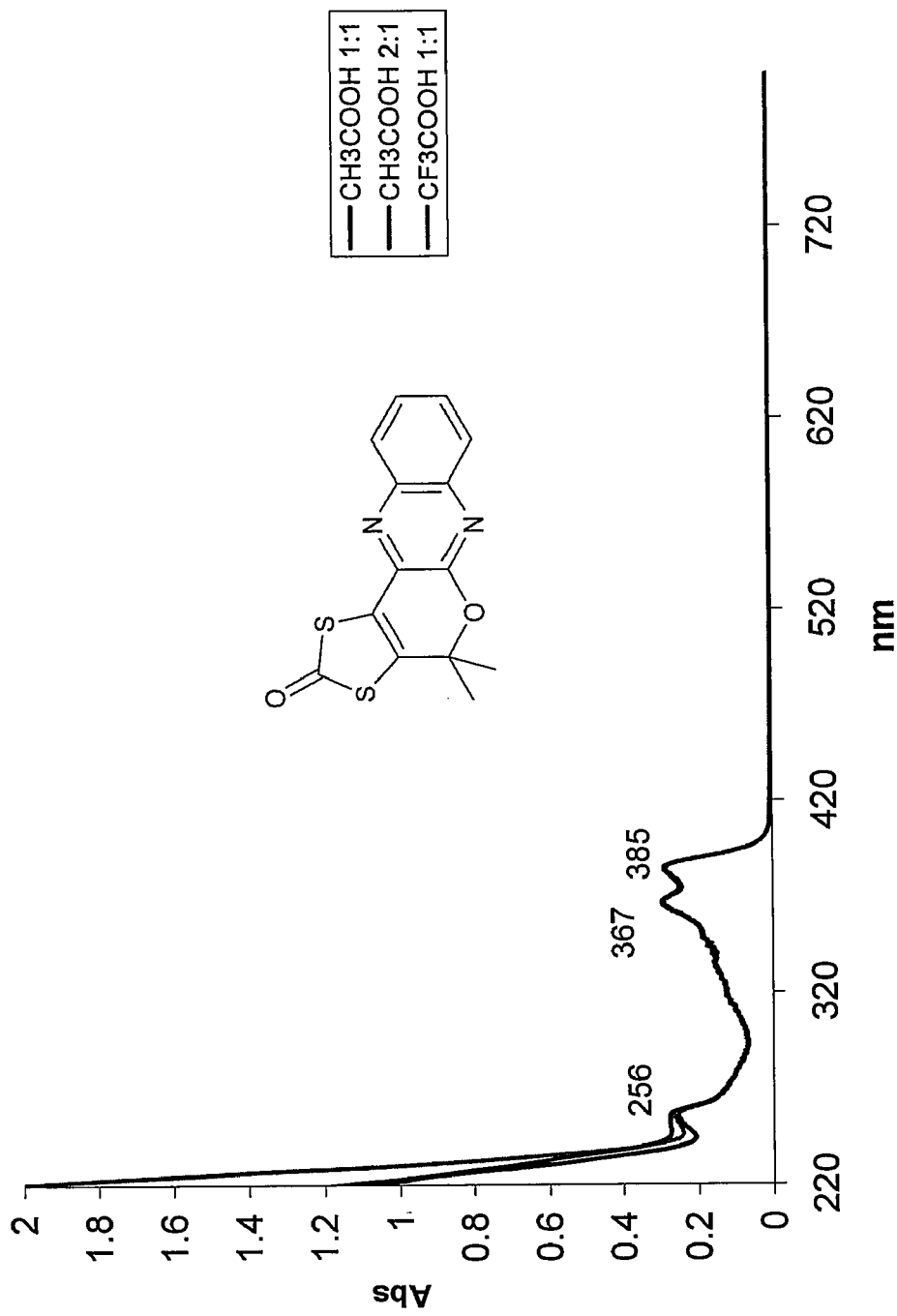
FIGS. 19-23 illustrate electronic spectra and excitation and emission spectra of one fluorophore of the present disclosure in methanol with acid or NEt$_4$OH.
Figure 20:
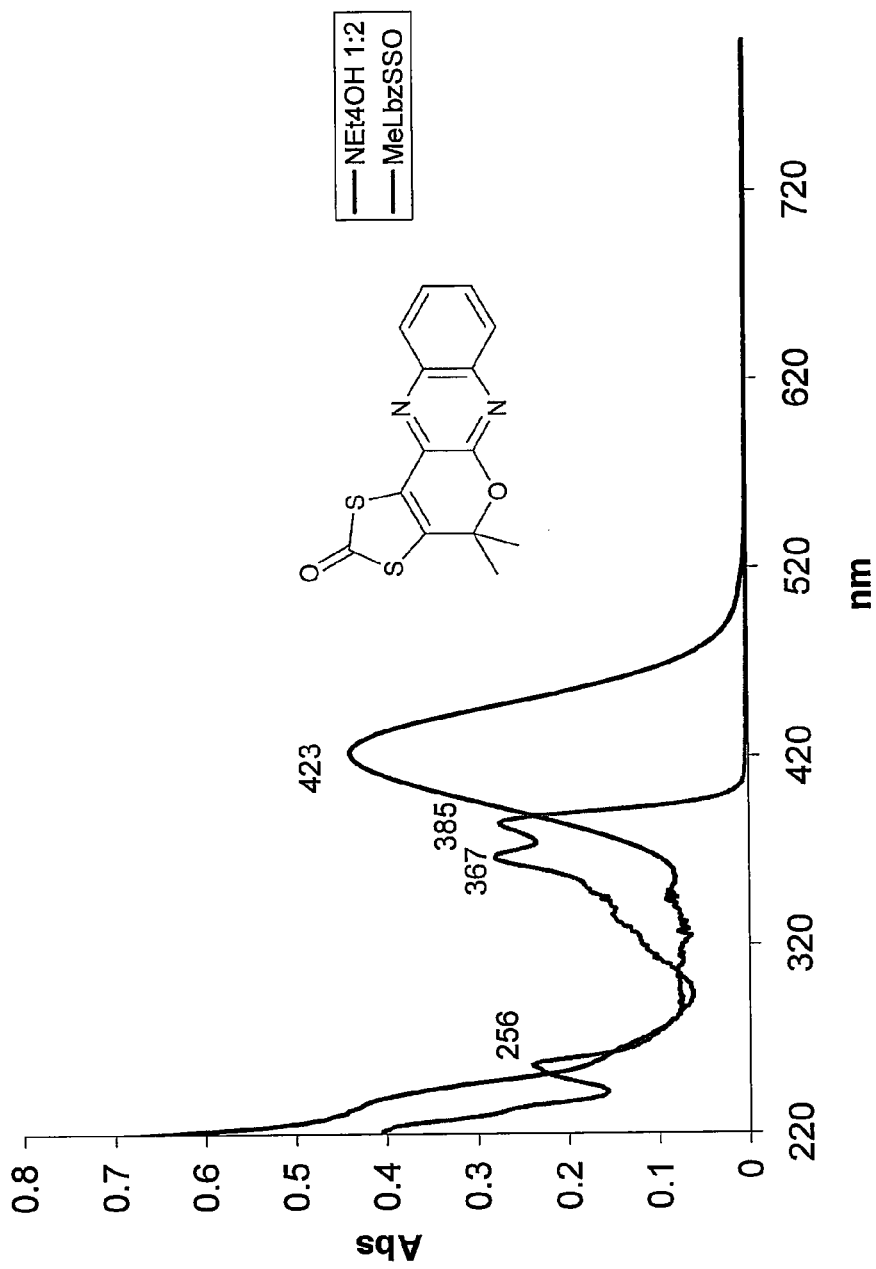
Figure 21:
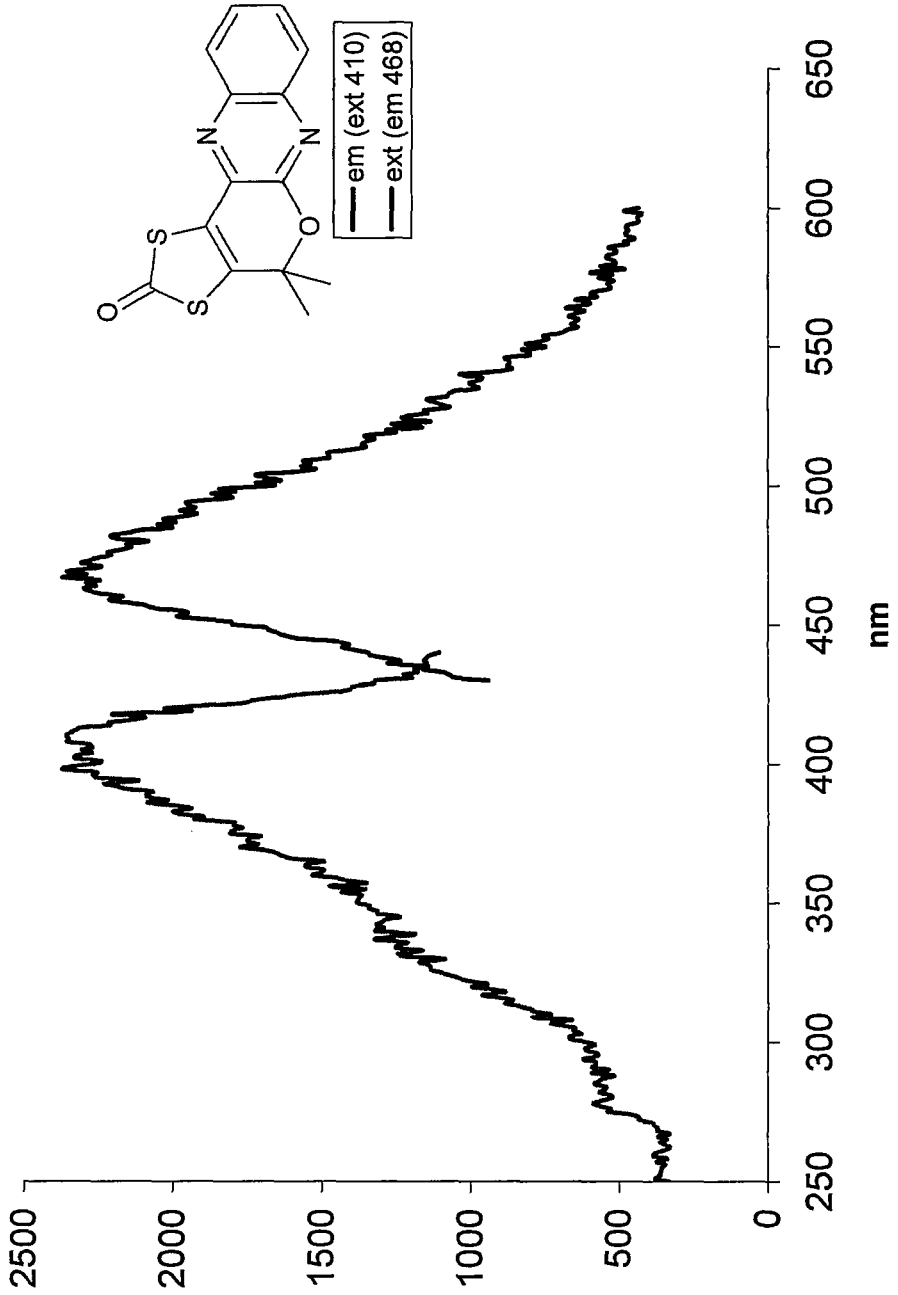
Figure 22:
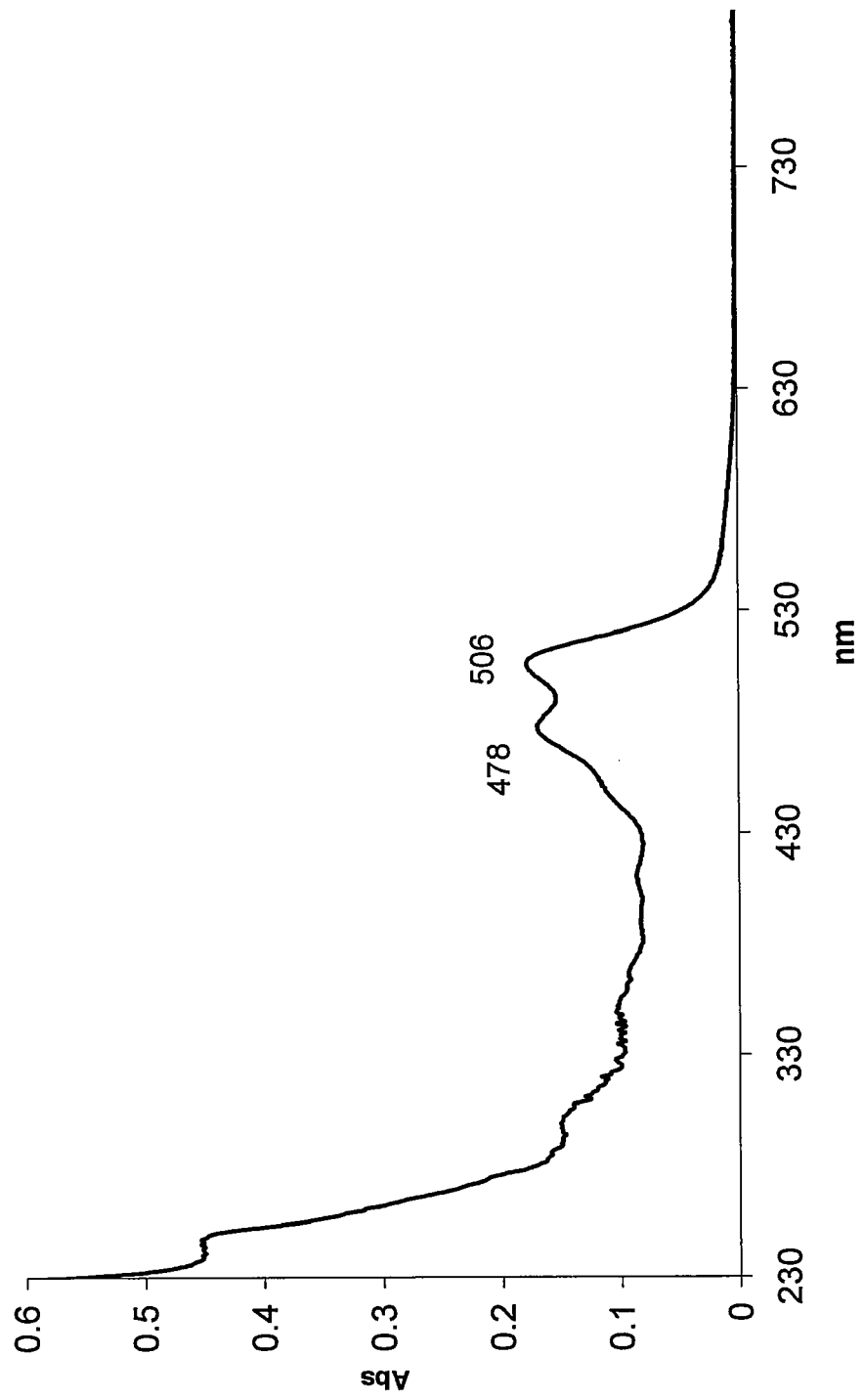
Figure 23:
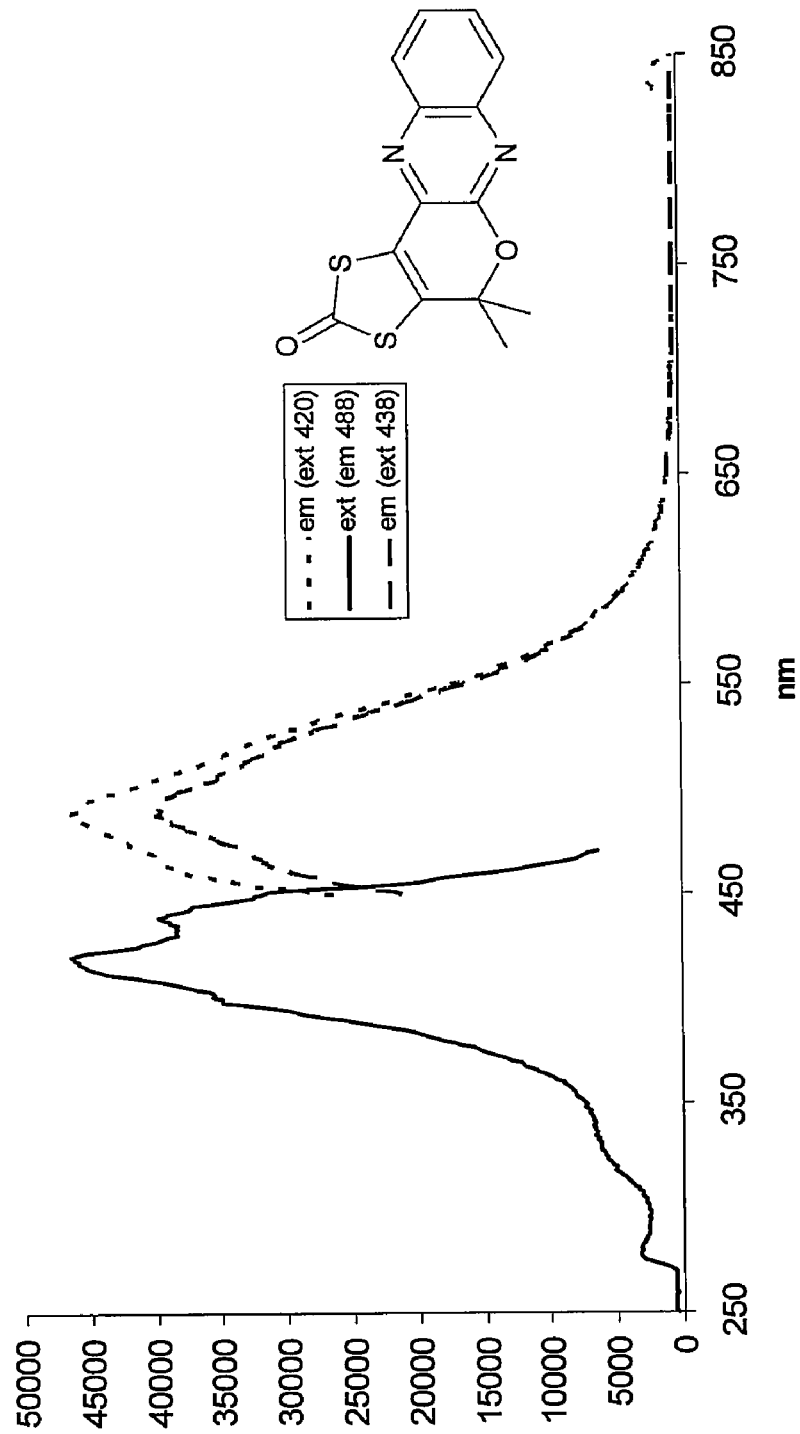
Figure 24:
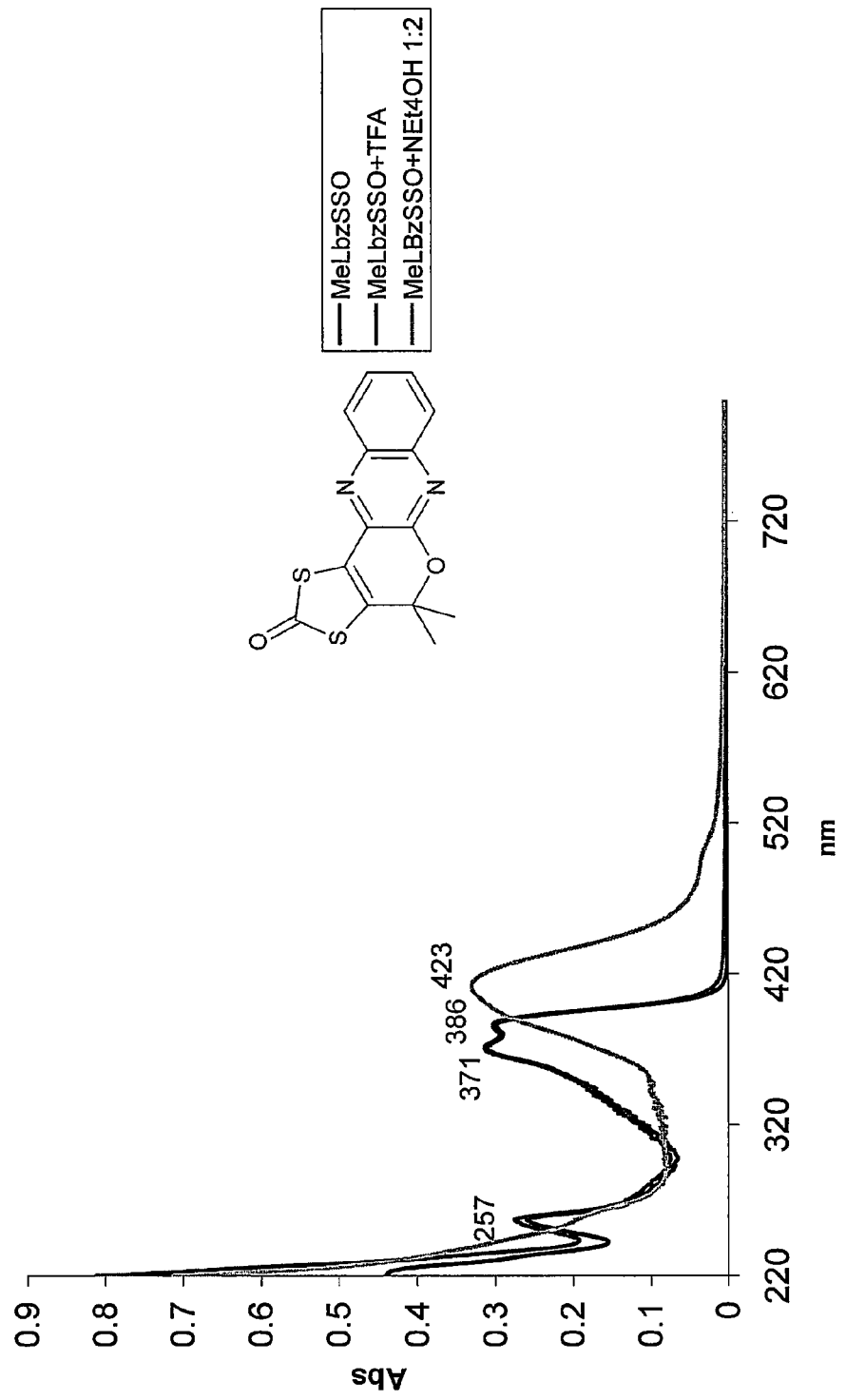
FIGS. 24-28 illustrate electronic spectra and excitation and emission spectra of one fluorophore of the present disclosure in methanol with trifluoroacetic acid (TFA) or NEt$_4$OH.
Figure 25:
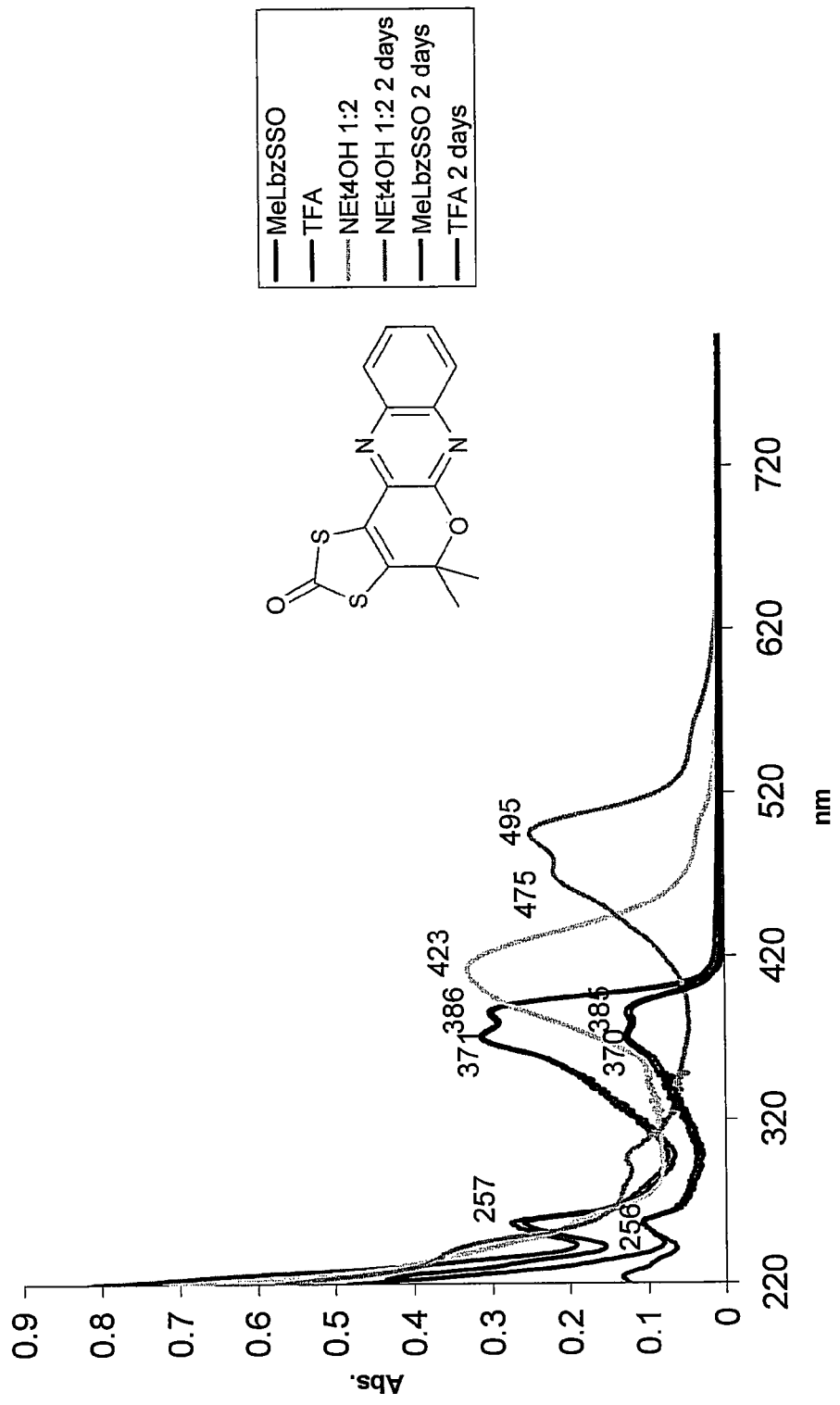
Figure 26:
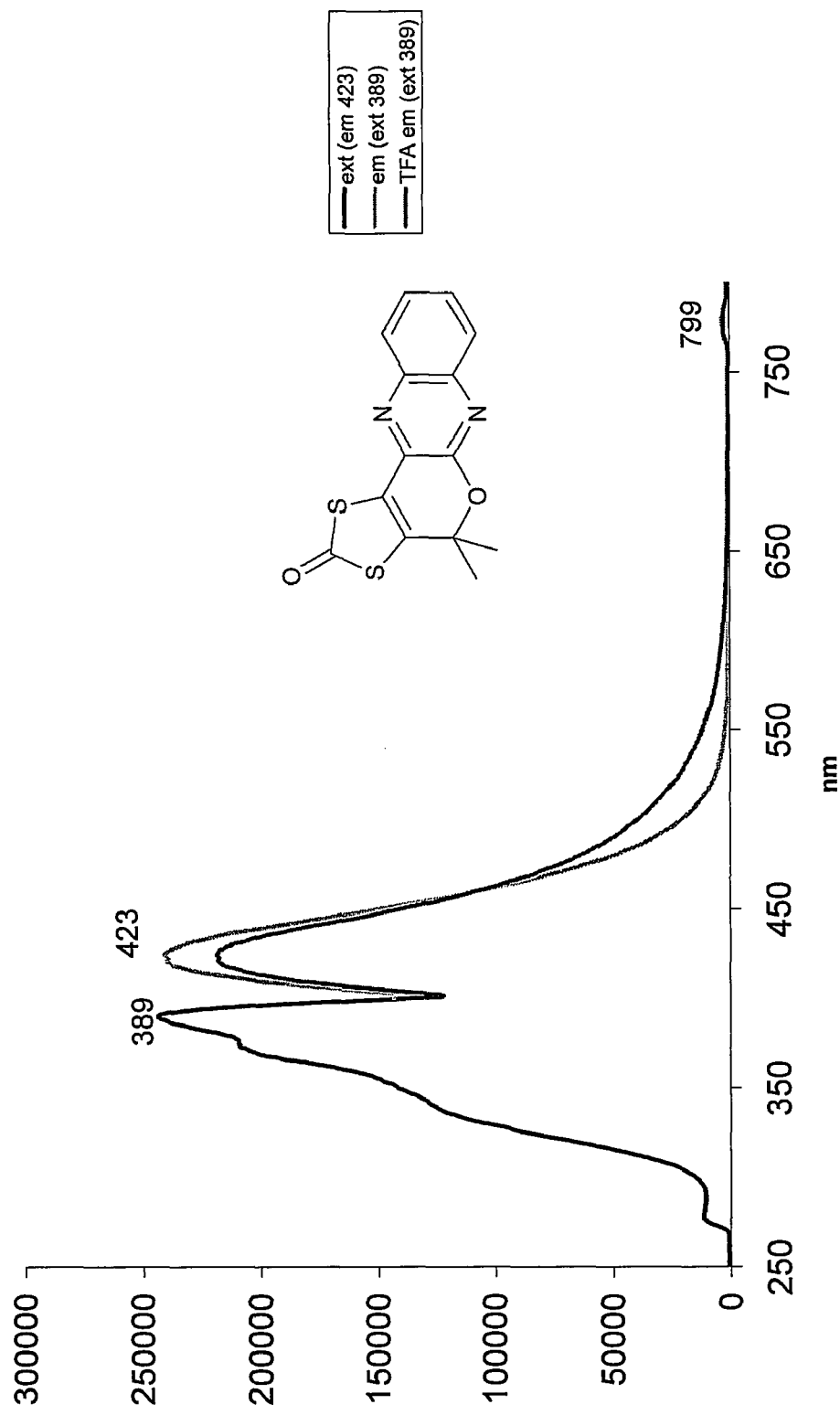
Figure 27:
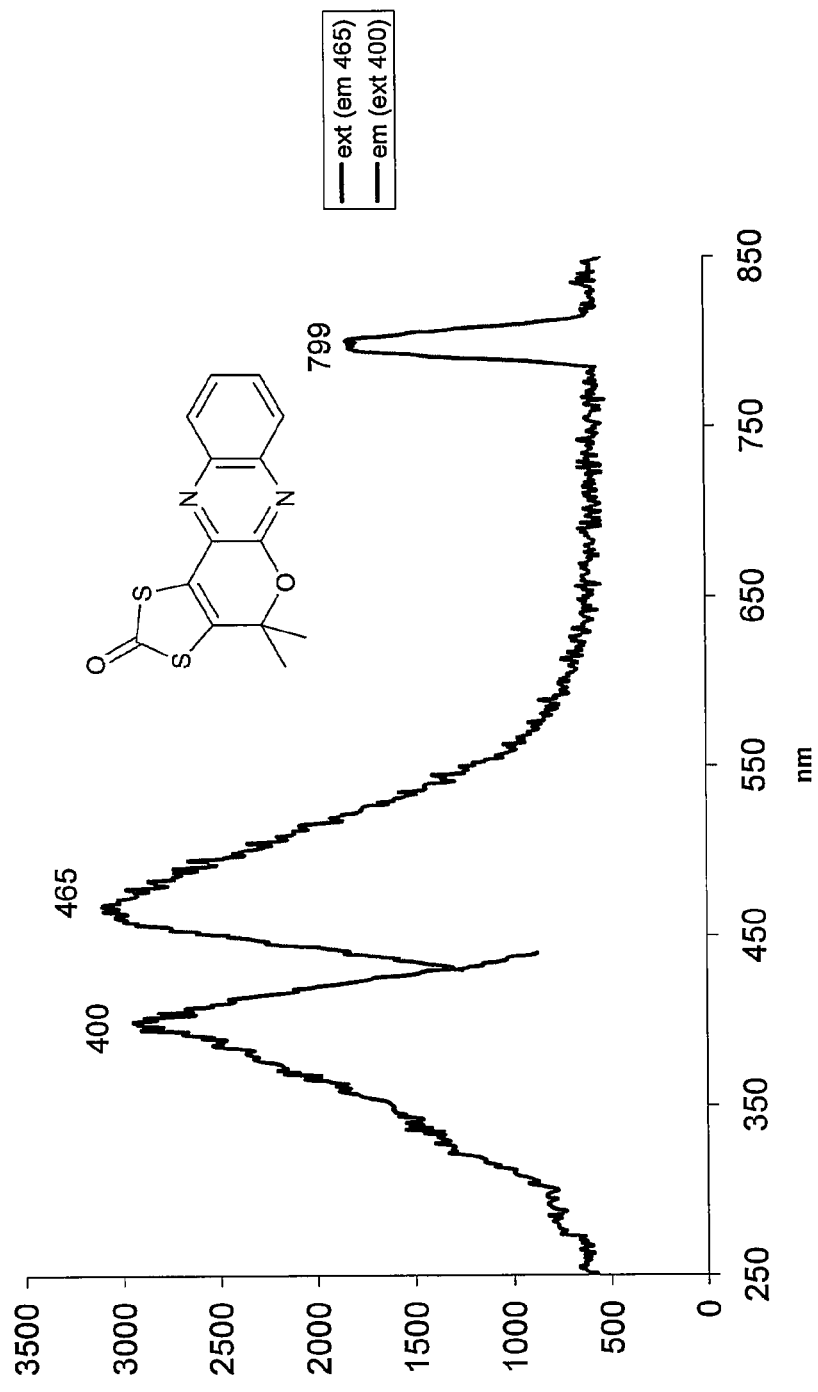
Figure 28:
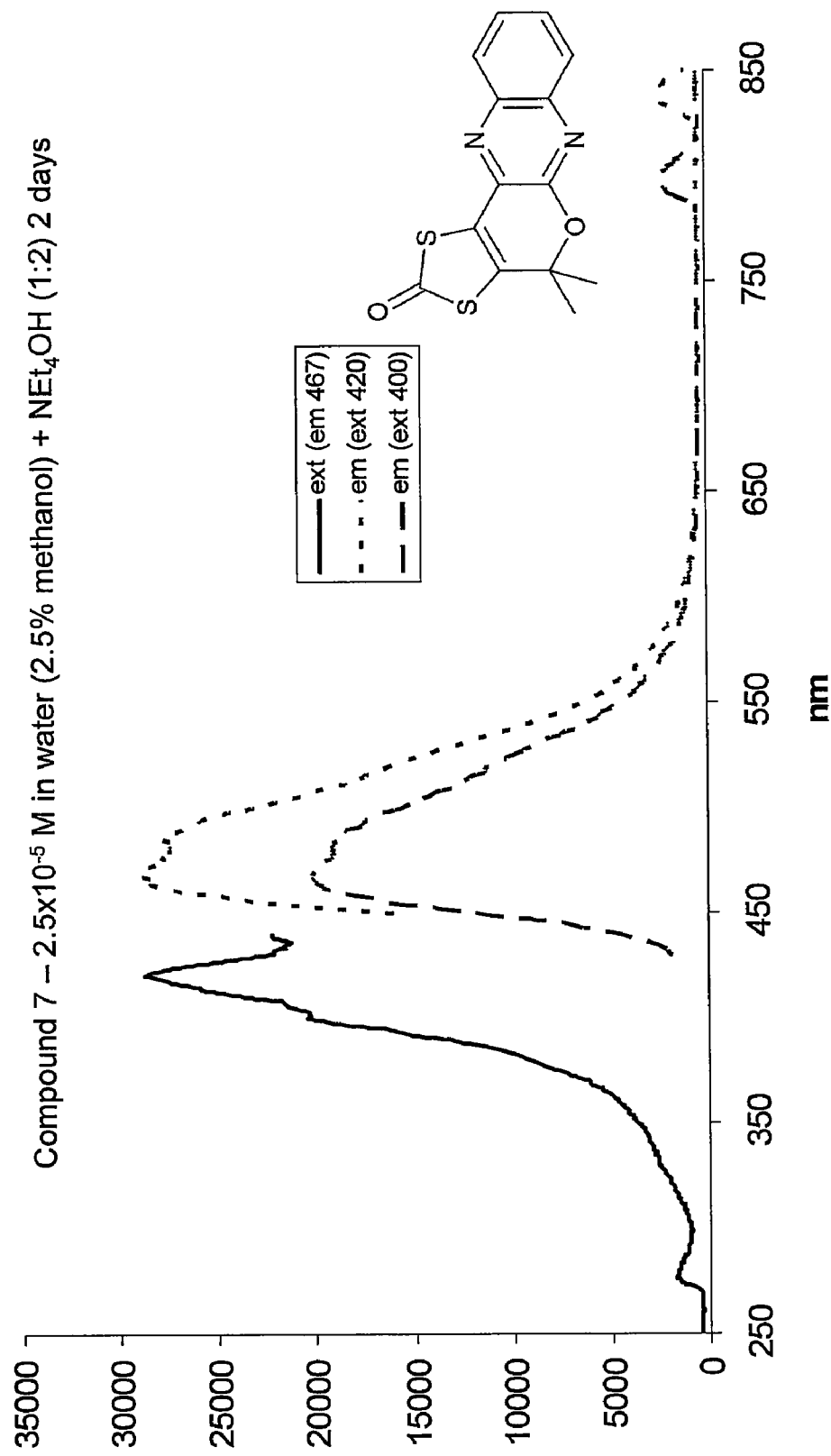
Figure 29:
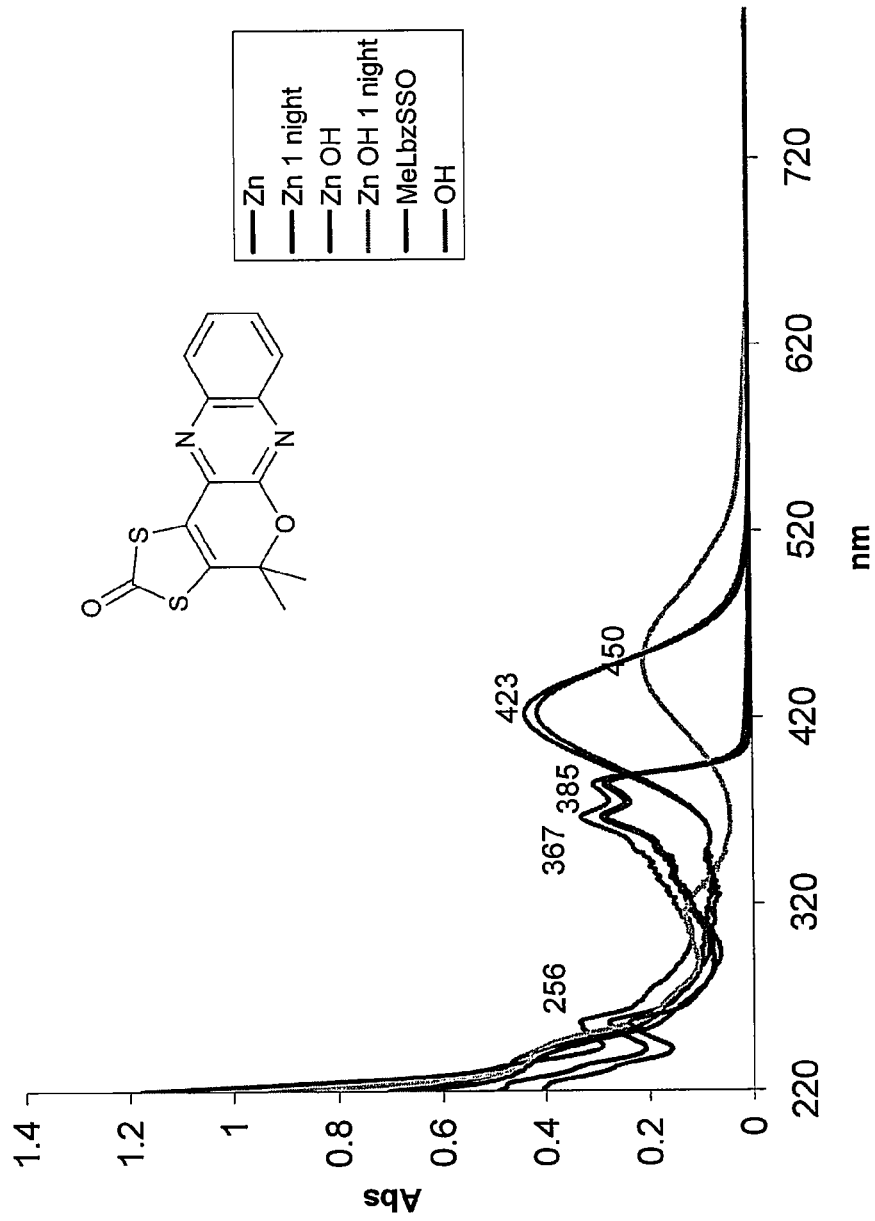
FIGS. 29-37 illustrate electronic spectra and excitation and emission spectra of one fluorophore of the present disclosure complexed to metal ions ($Zn^{2+}$, $Cd^{2+}$, $Hg^{2+}$, and $Pb^{2+}$).
Figure 30:
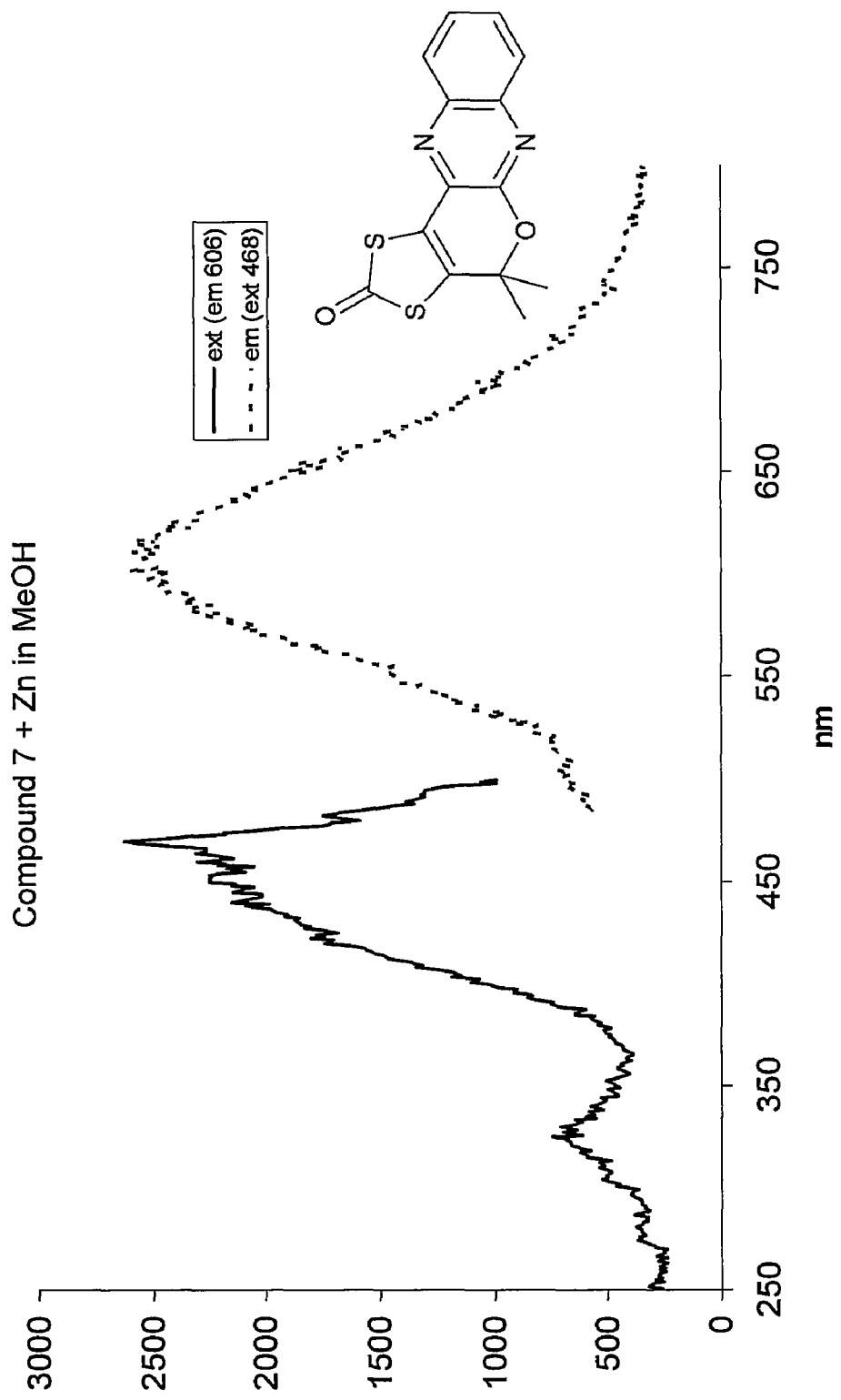
Figure 31:
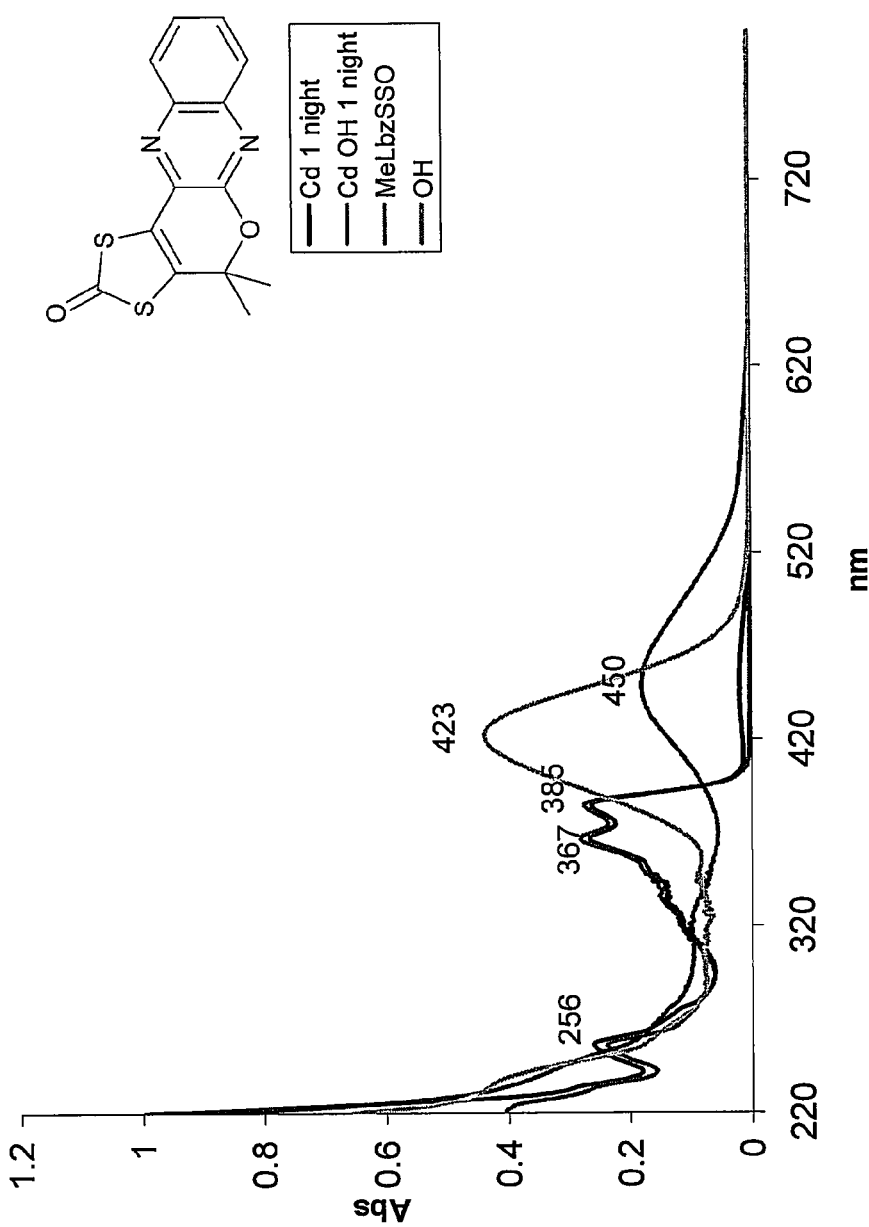
Figure 32:
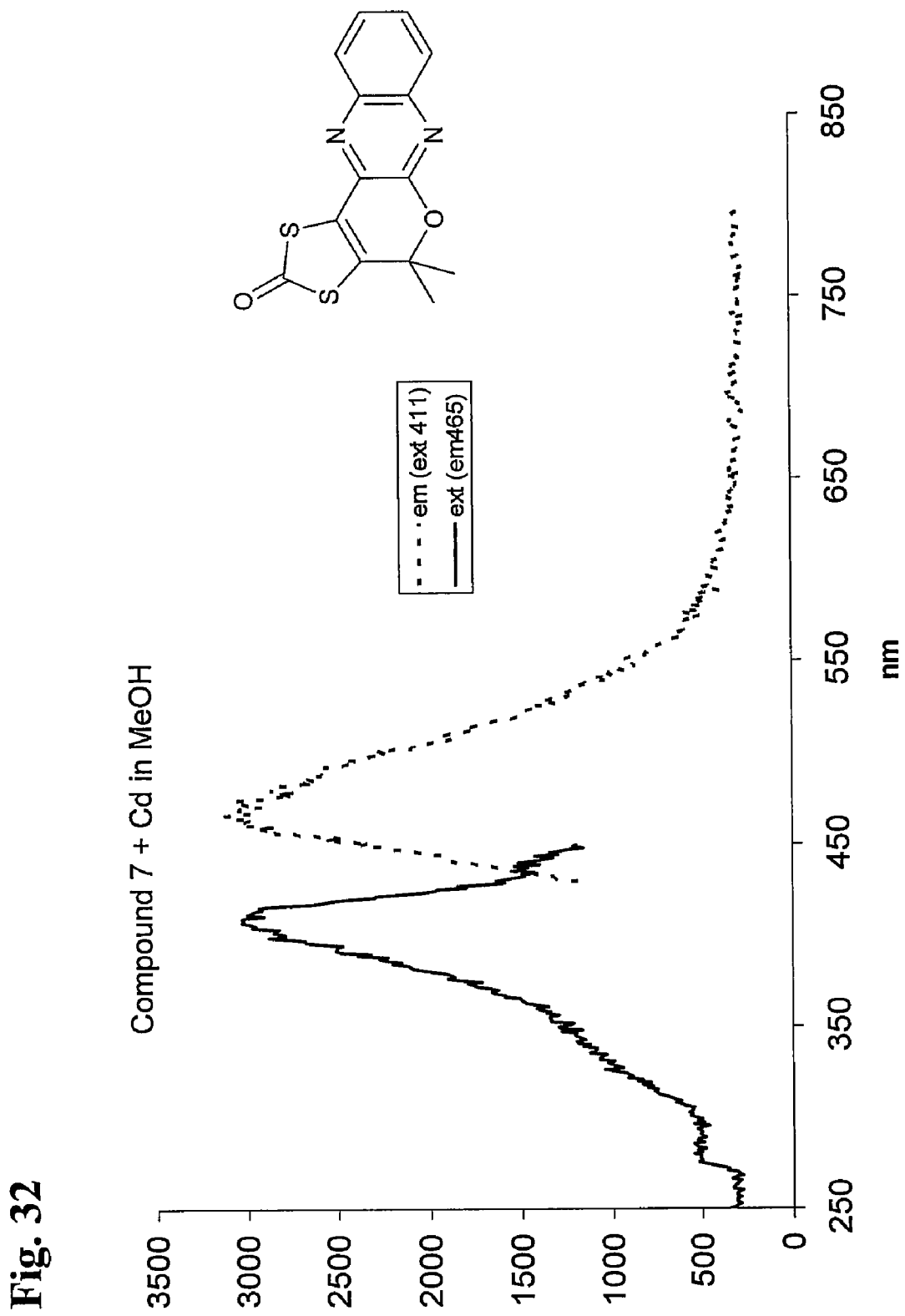
Figure 33:
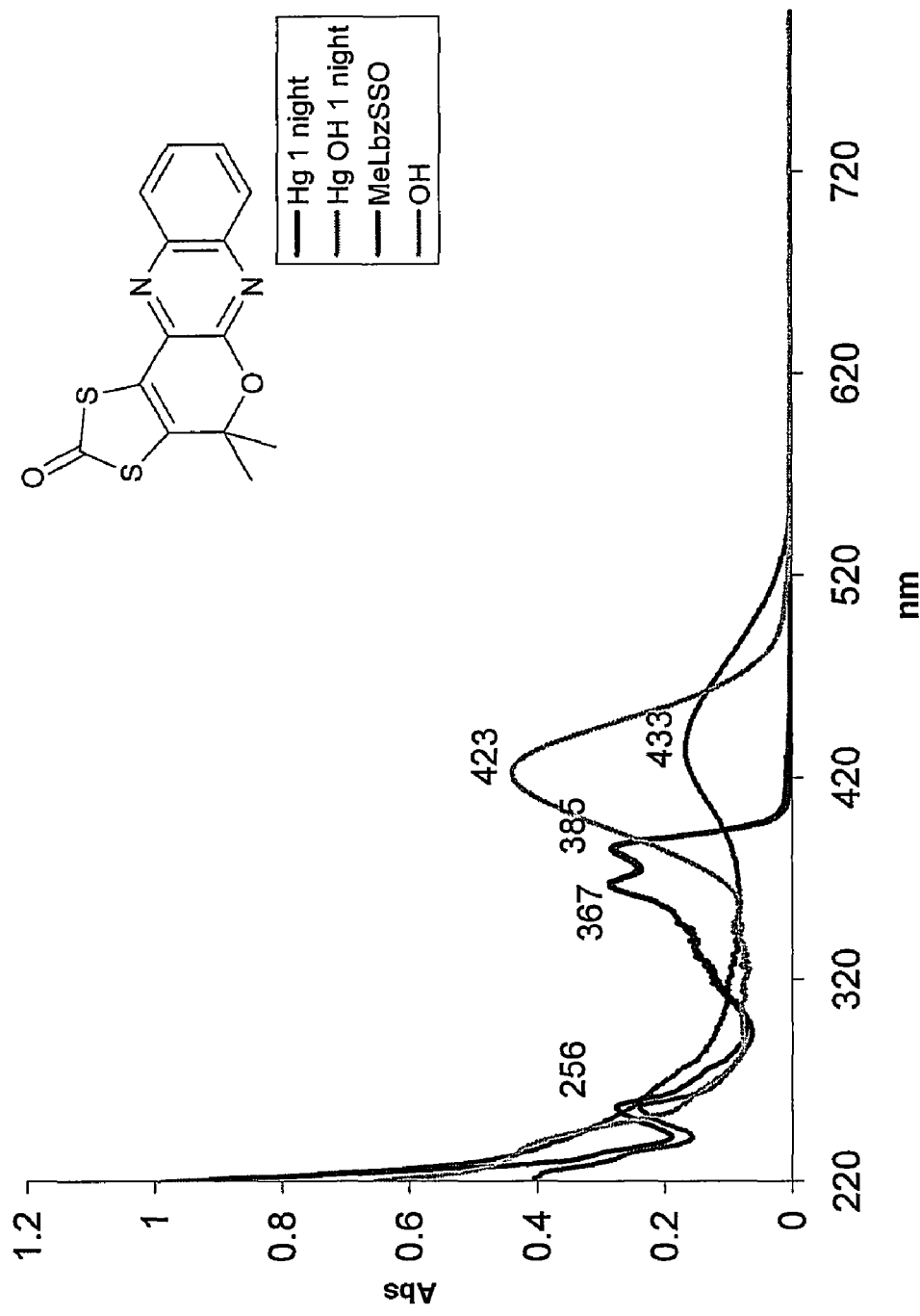
Figure 34:
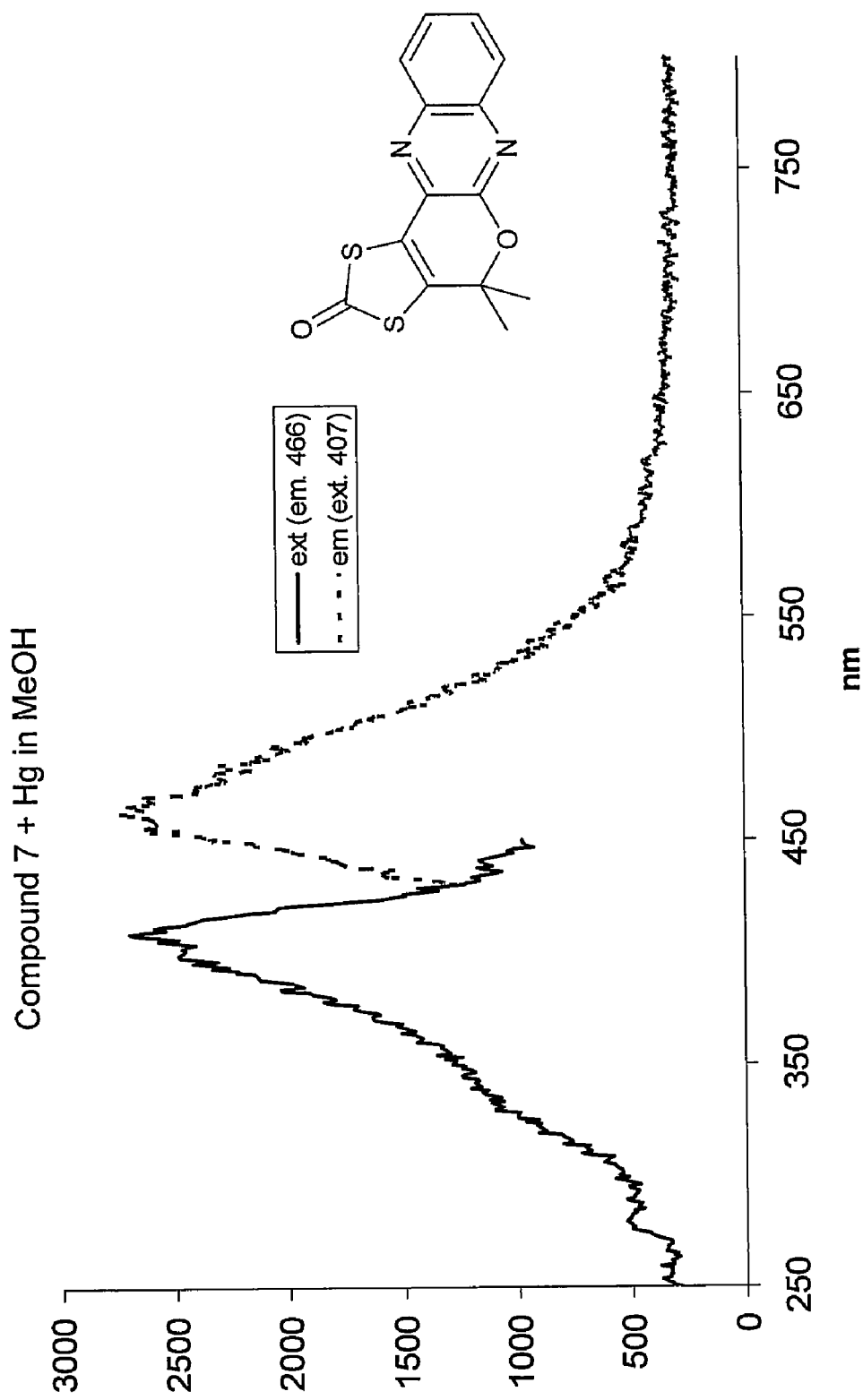
Figure 35:
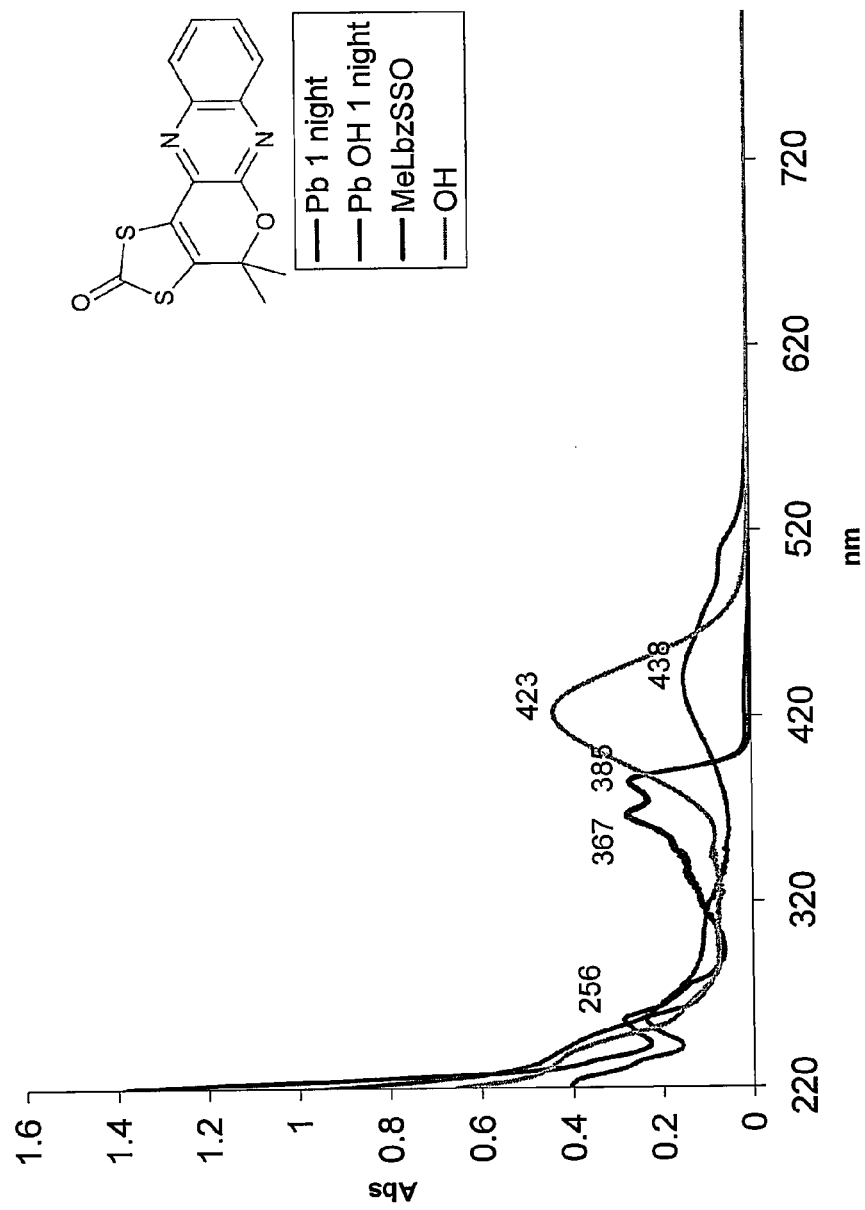
Figure 36:
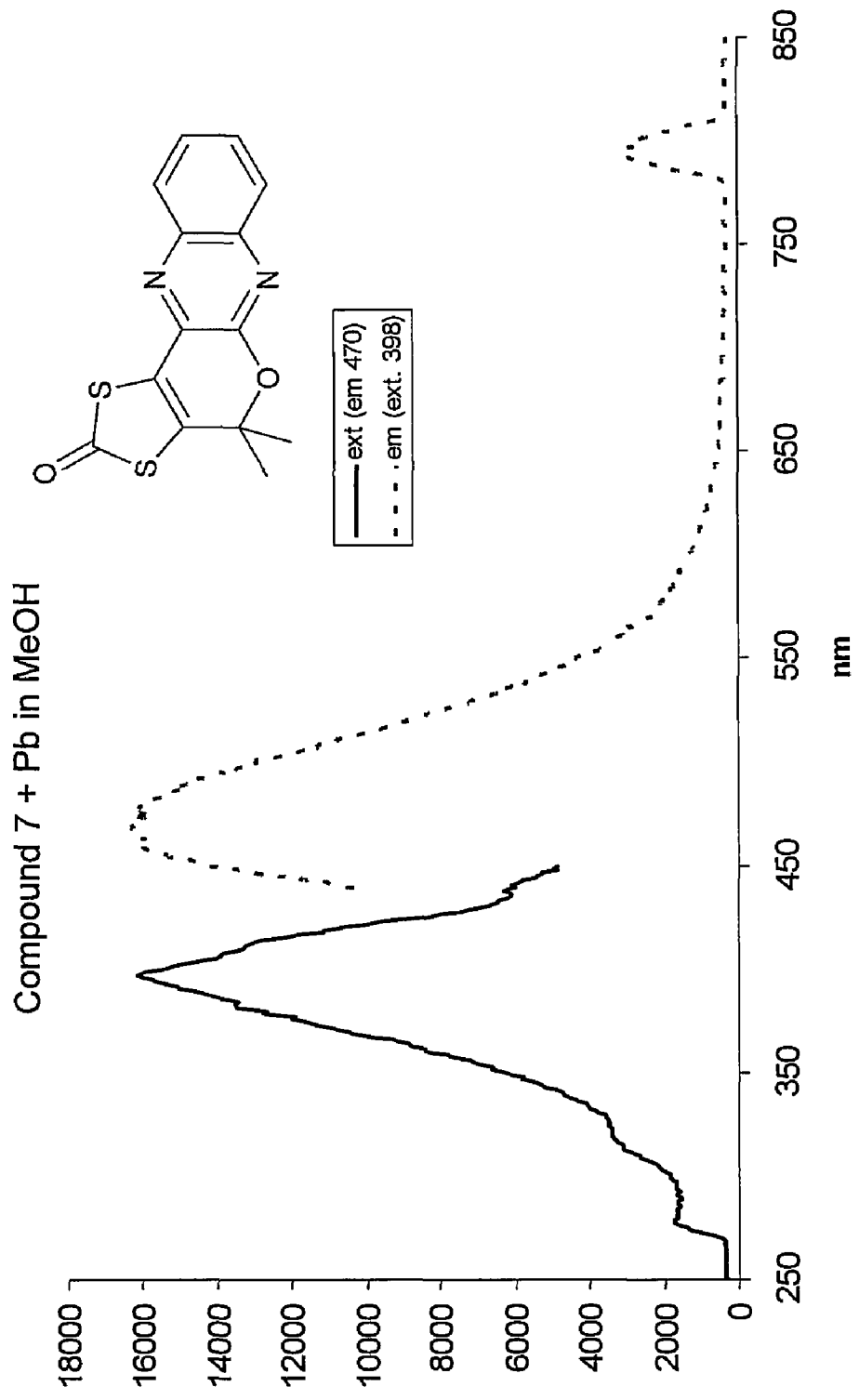
Figure 37:
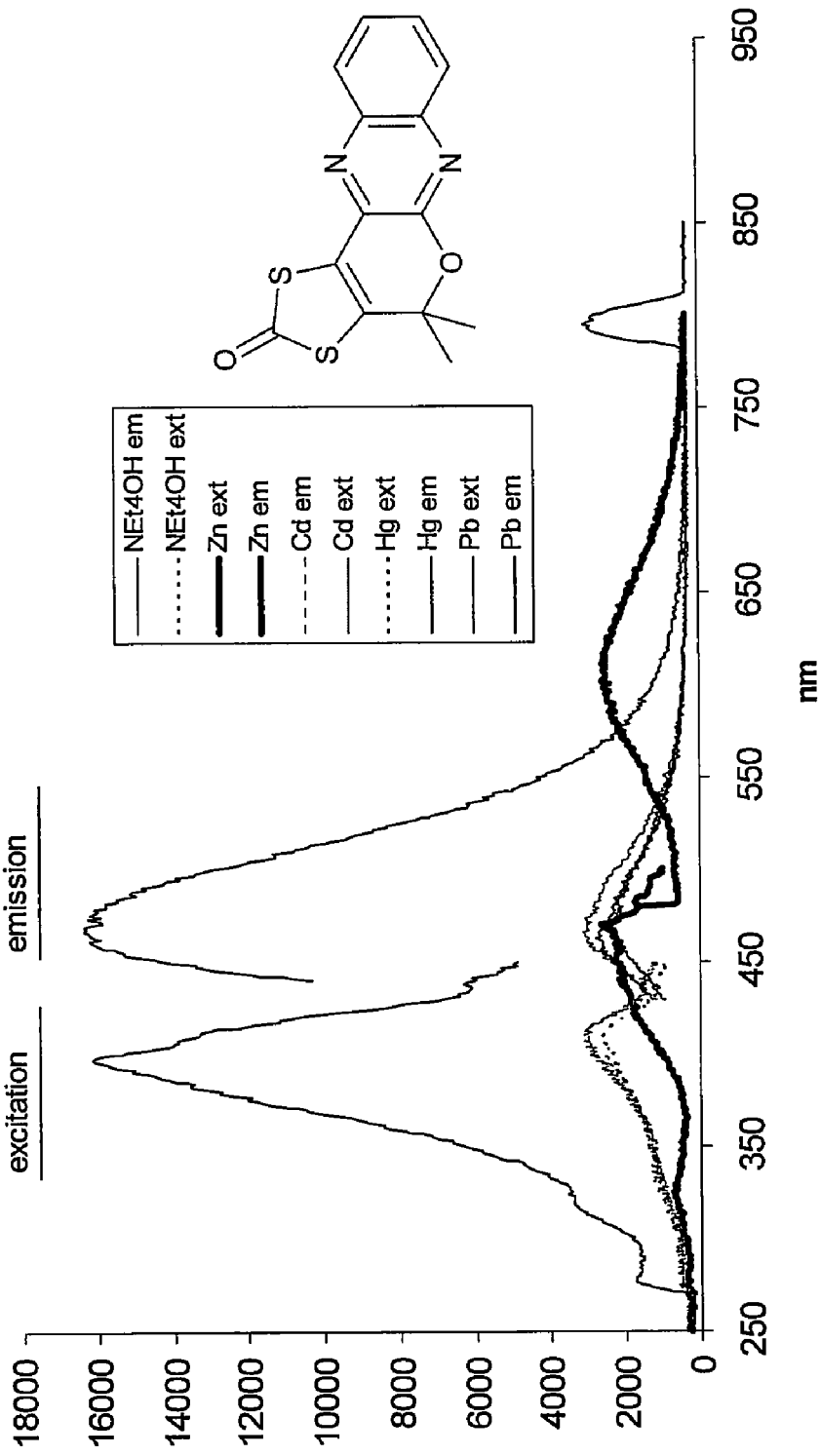
Figure 38:
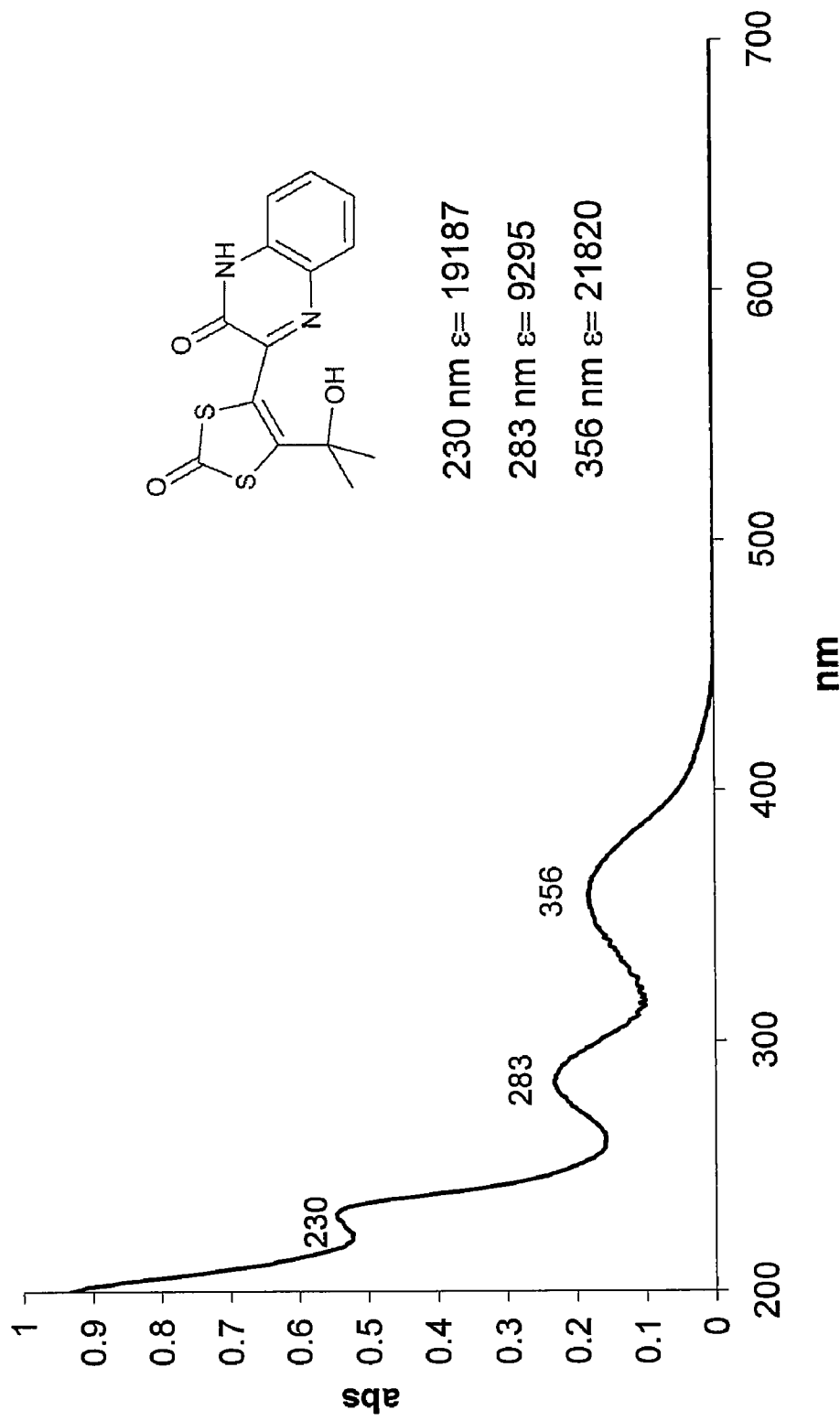
FIGS. 38-39 illustrate electronic spectra and excitation and emission spectra of the open form of one fluorophore of the present disclosure.
Figure 39:
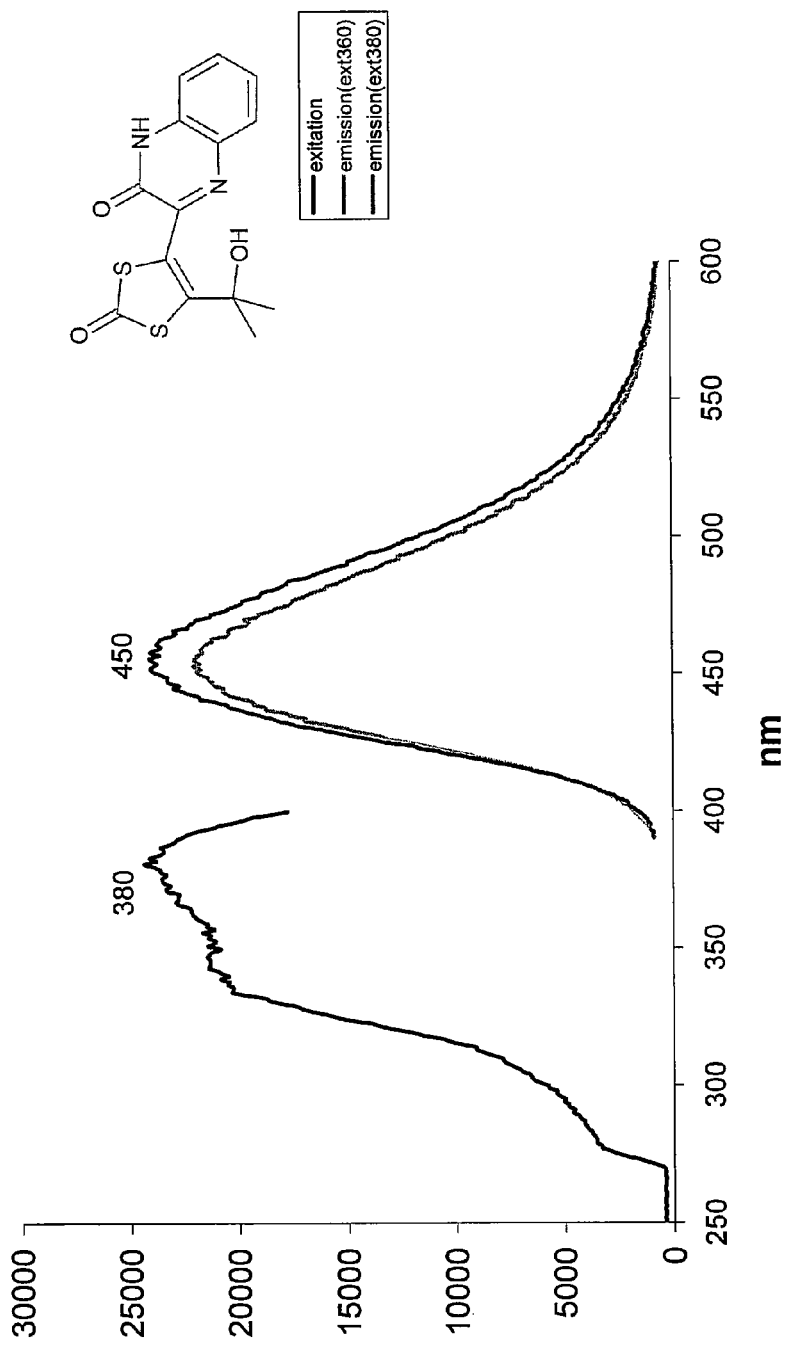
Figure 40:
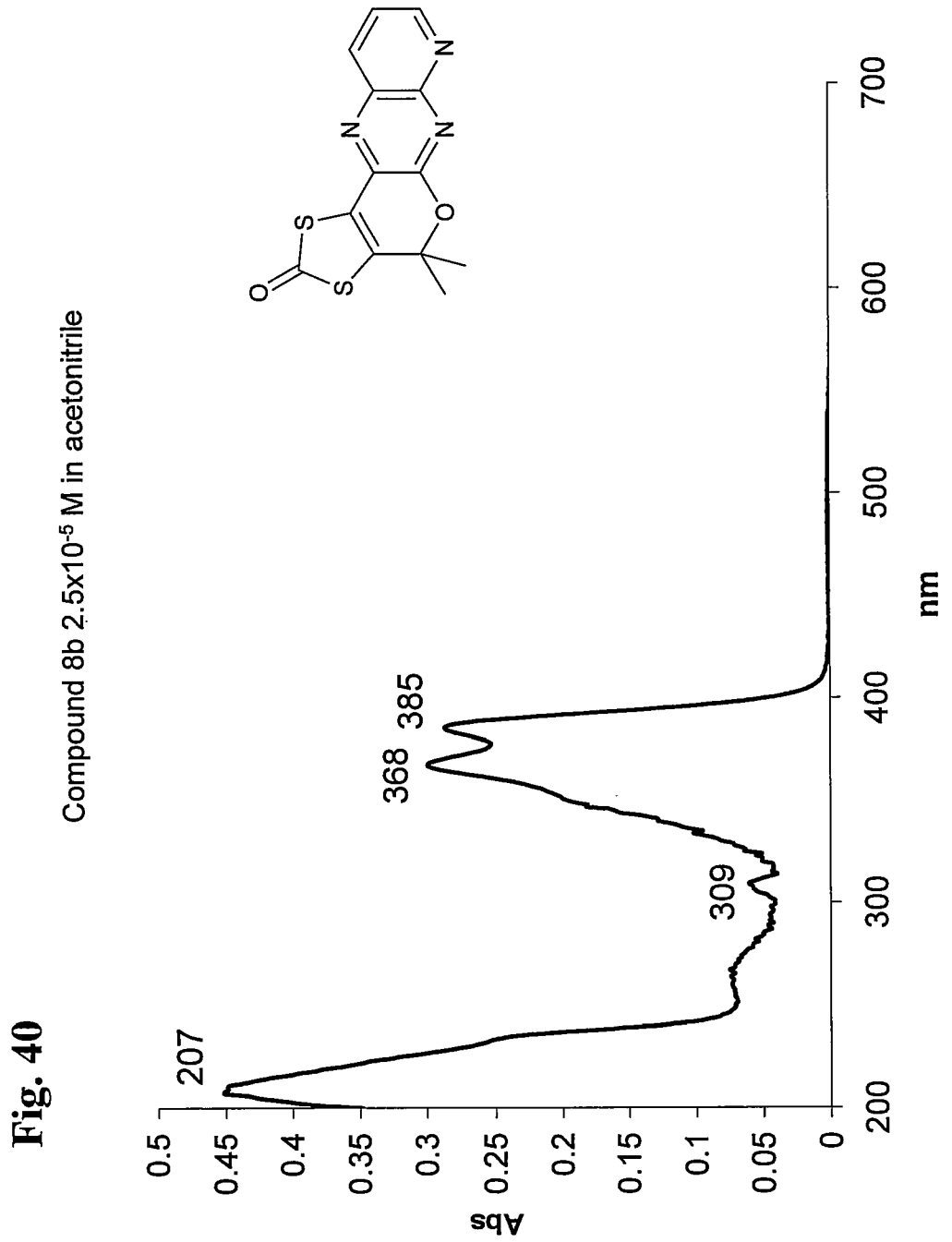
FIGS. 40-41 illustrate electronic spectra and excitation and emission spectra of one fluorophore of the present disclosure.
Figure 41:
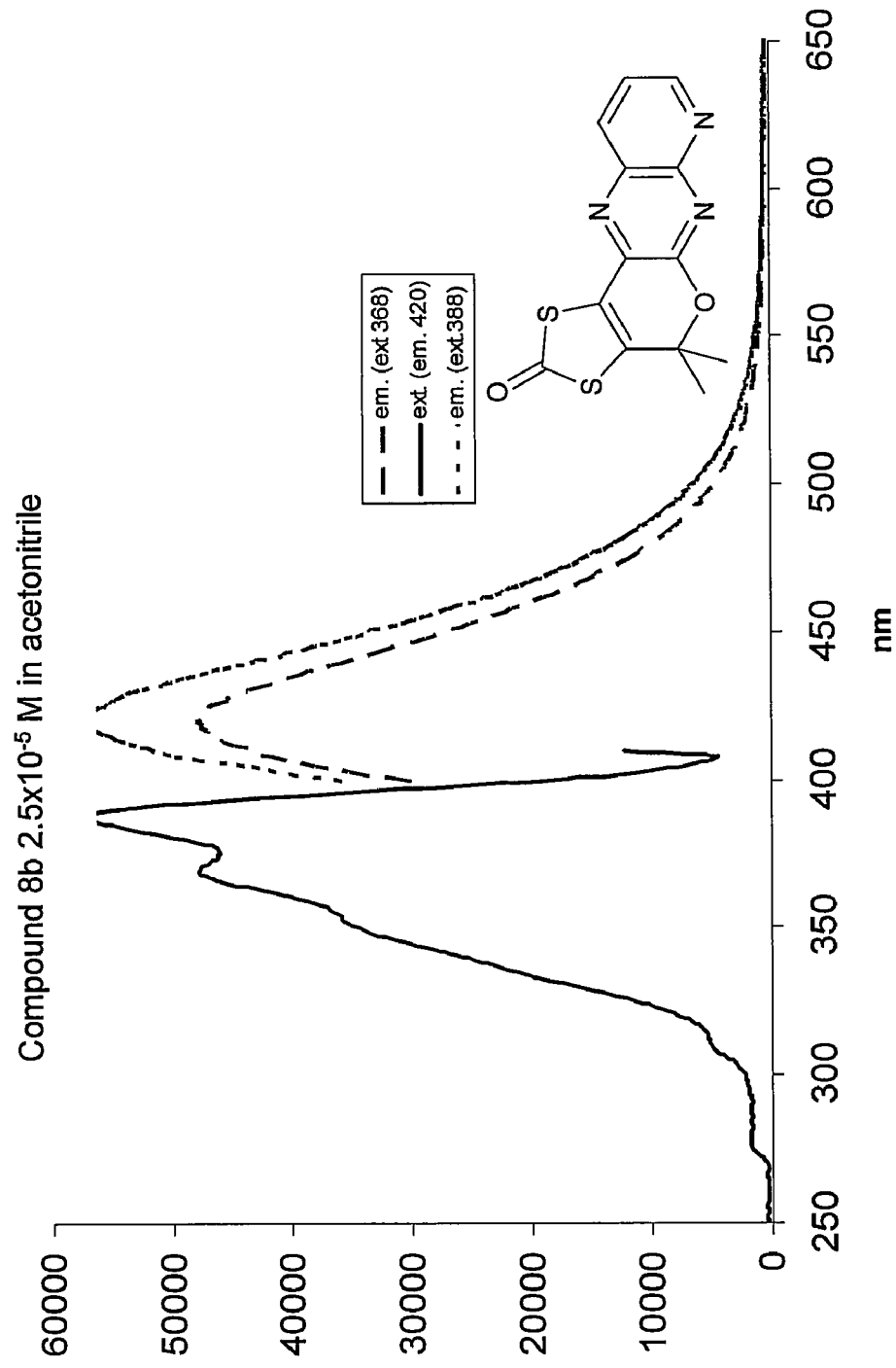
Figure 42:
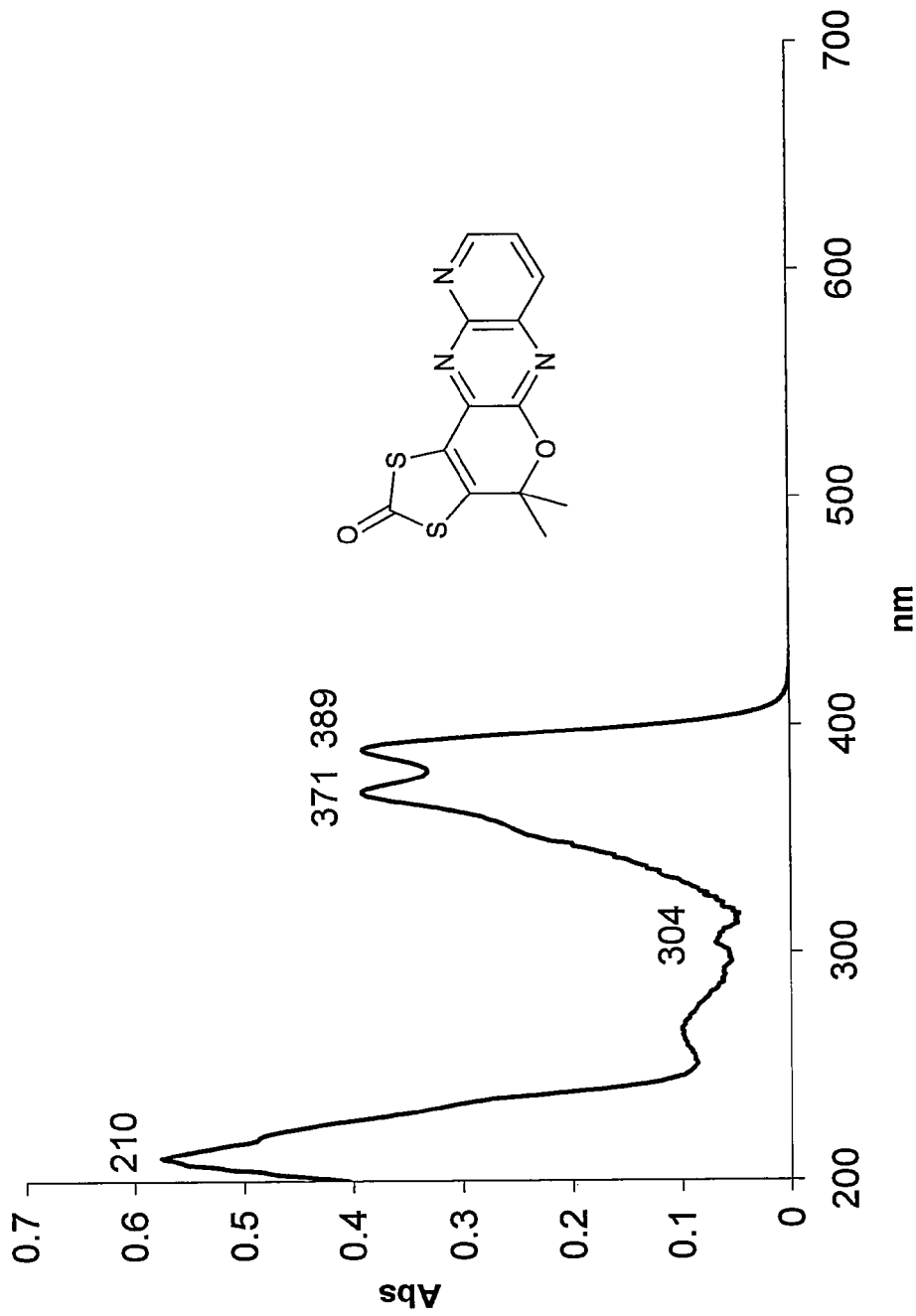
FIGS. 42-44 illustrate electronic spectra and excitation and emission spectra of one fluorophore of the present disclosure.
Figure 43:
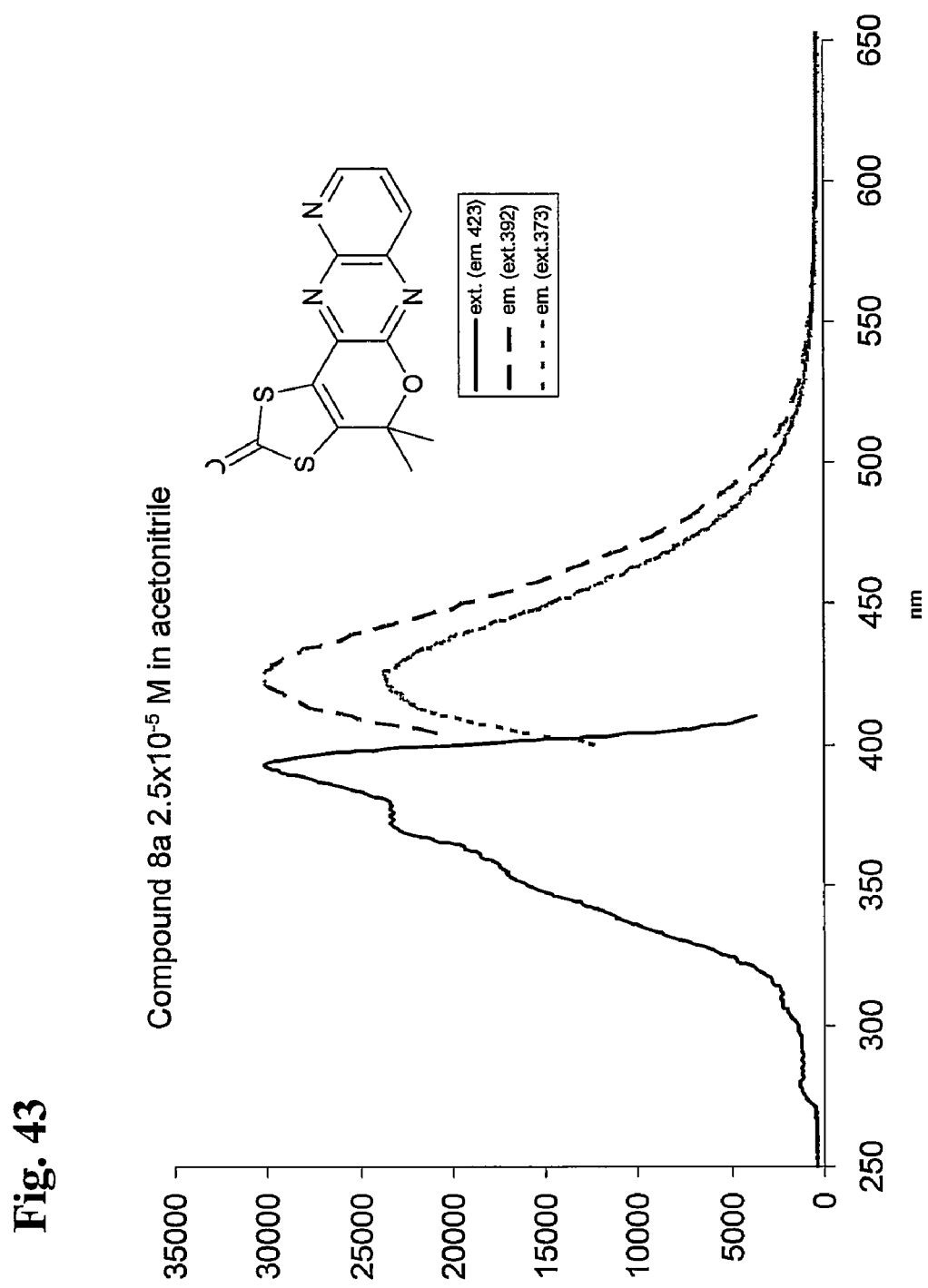
Figure 44:
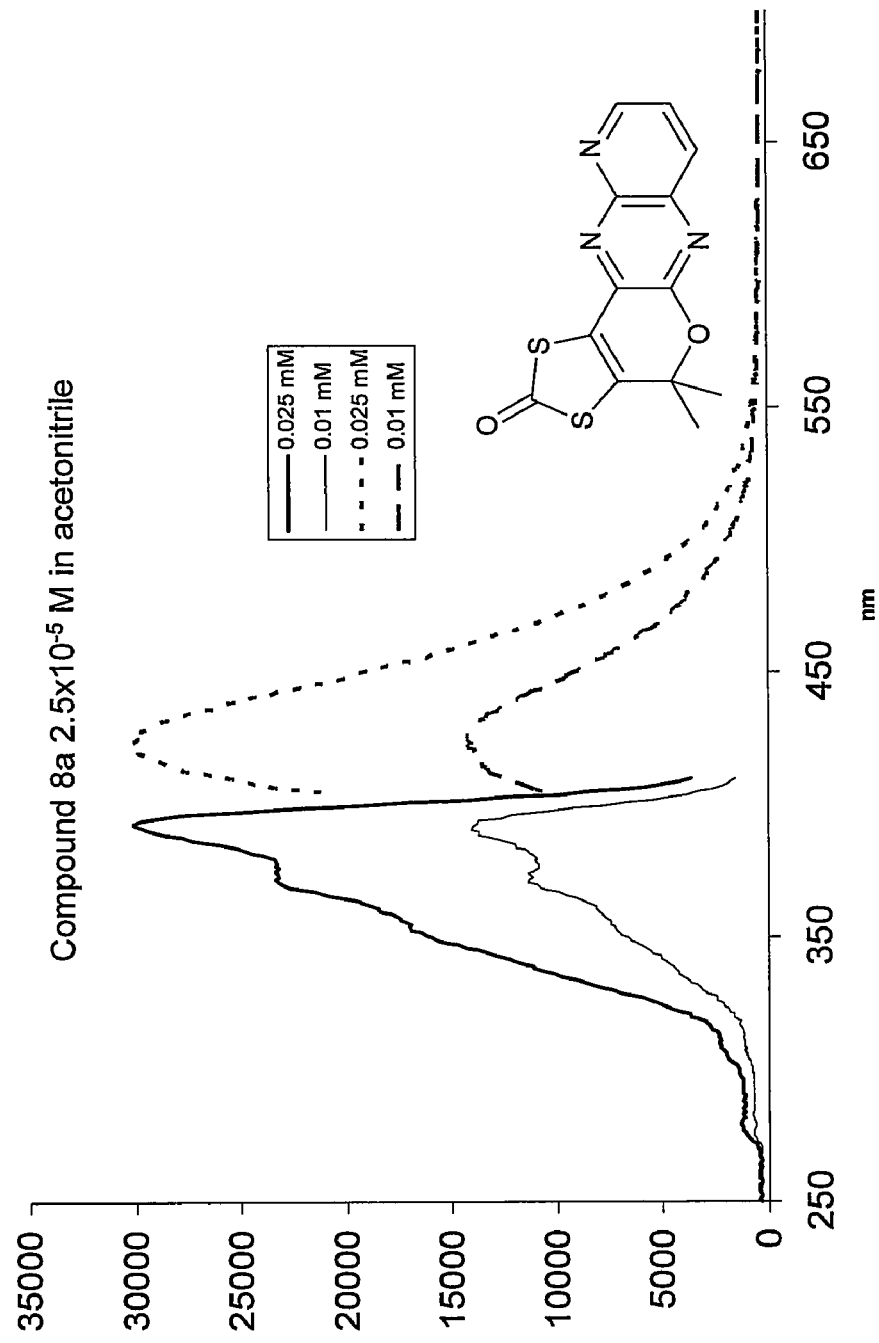
Figure 45:
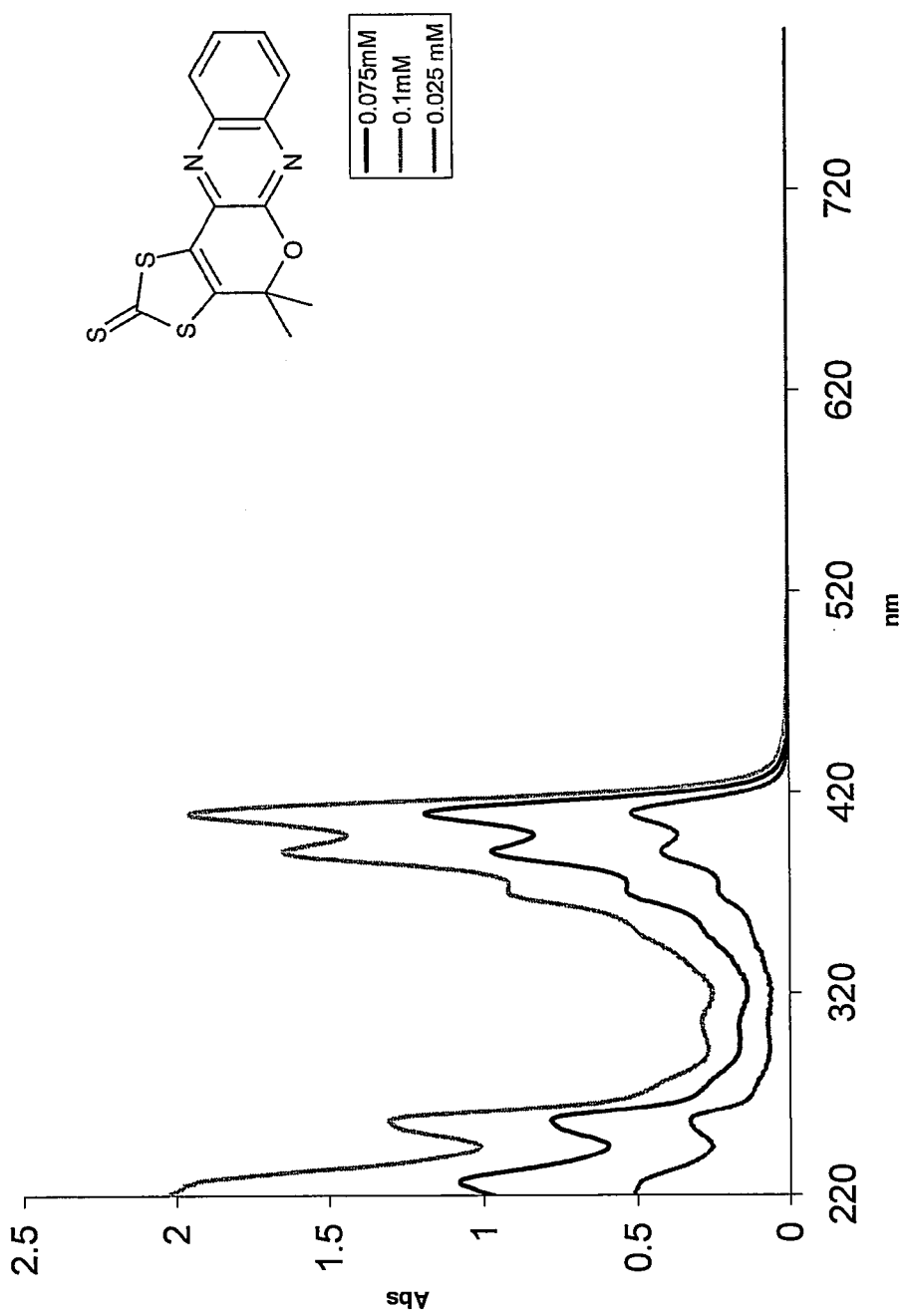
FIGS. 45-46 illustrate electronic spectra and excitation and emission spectra of one fluorophore of the present disclosure.
Figure 46:
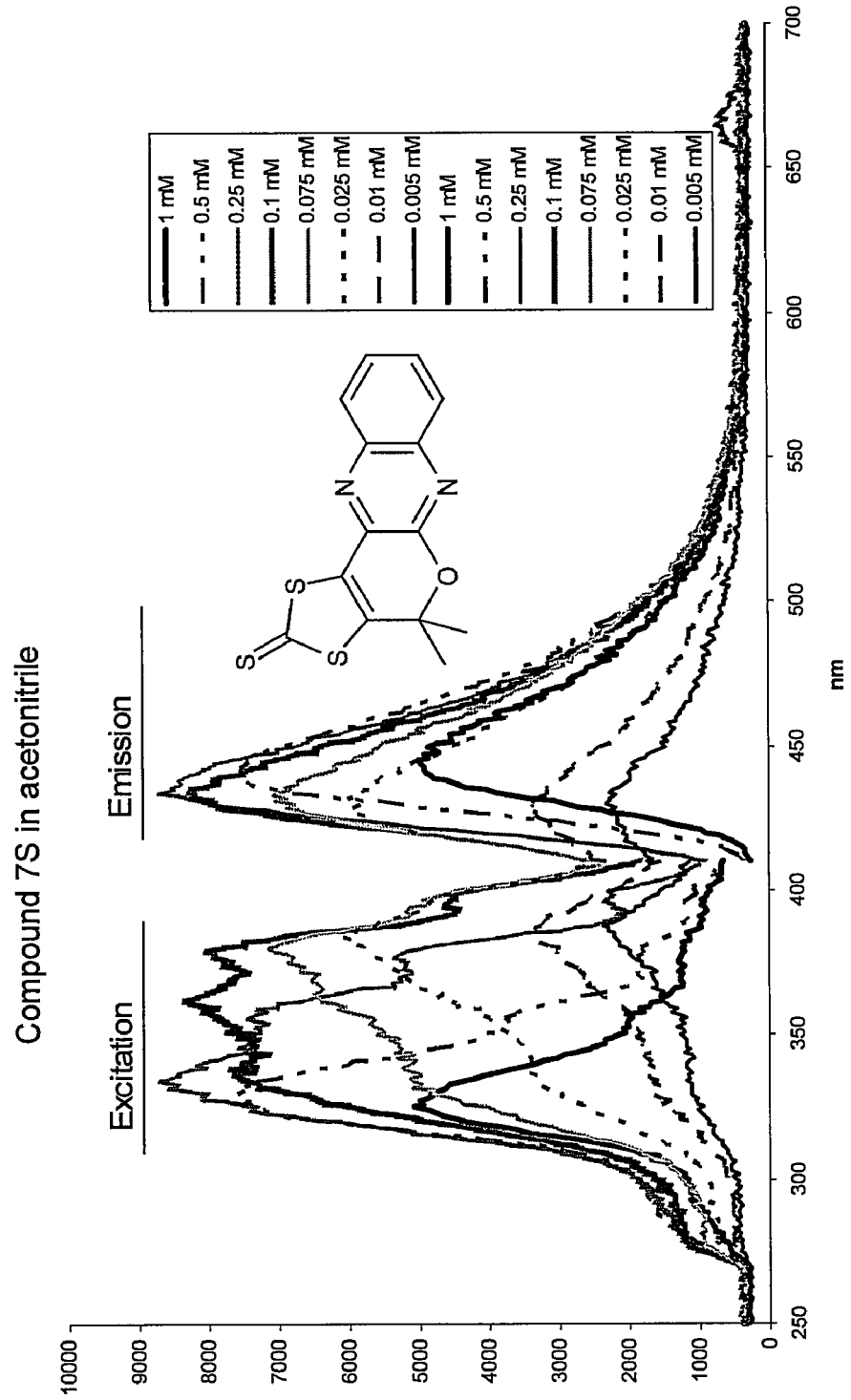
Figure 47:
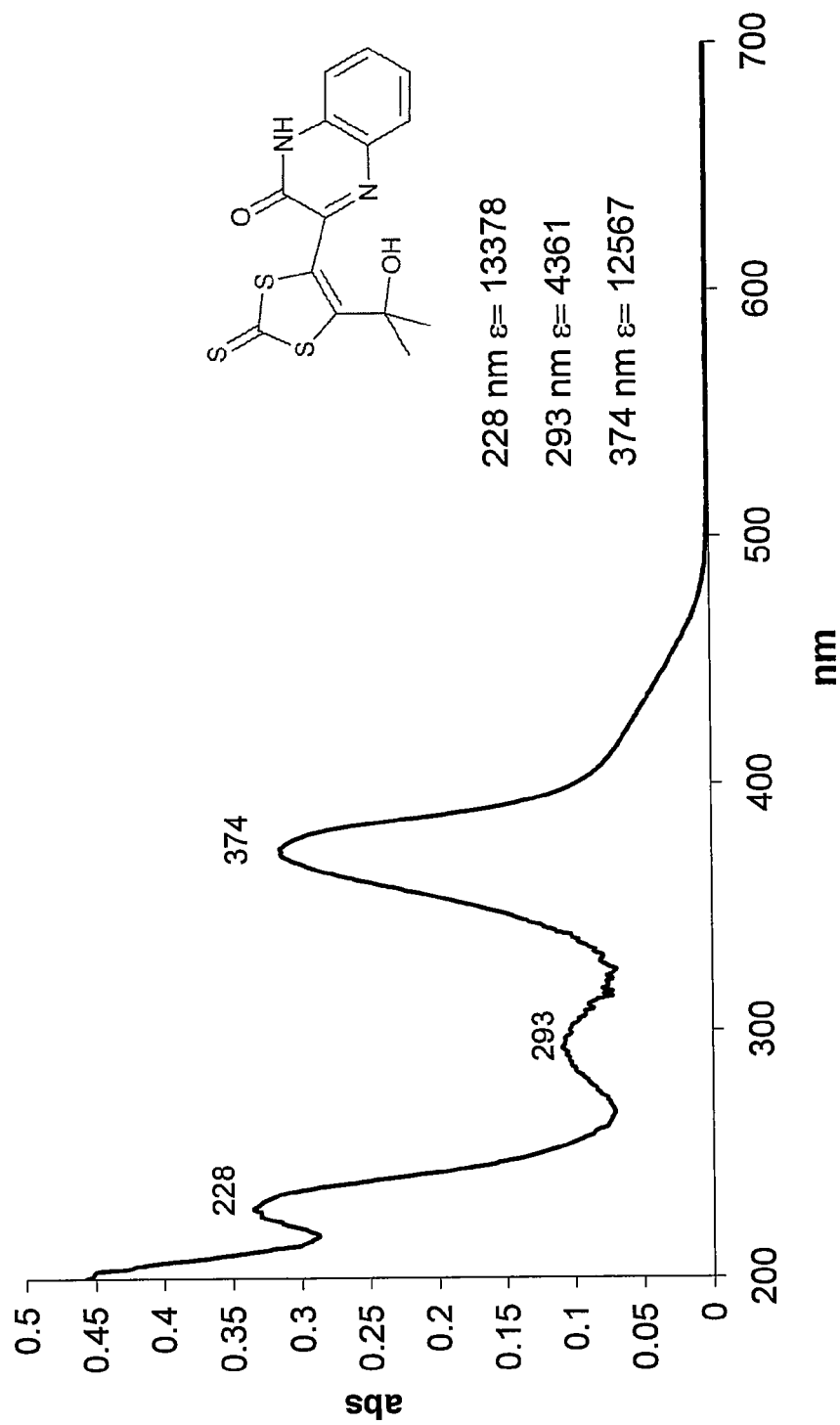
FIGS. 47-48 illustrate electronic spectra and excitation and emission spectra of the open form of one fluorophore of the present disclosure.
Figure 48:
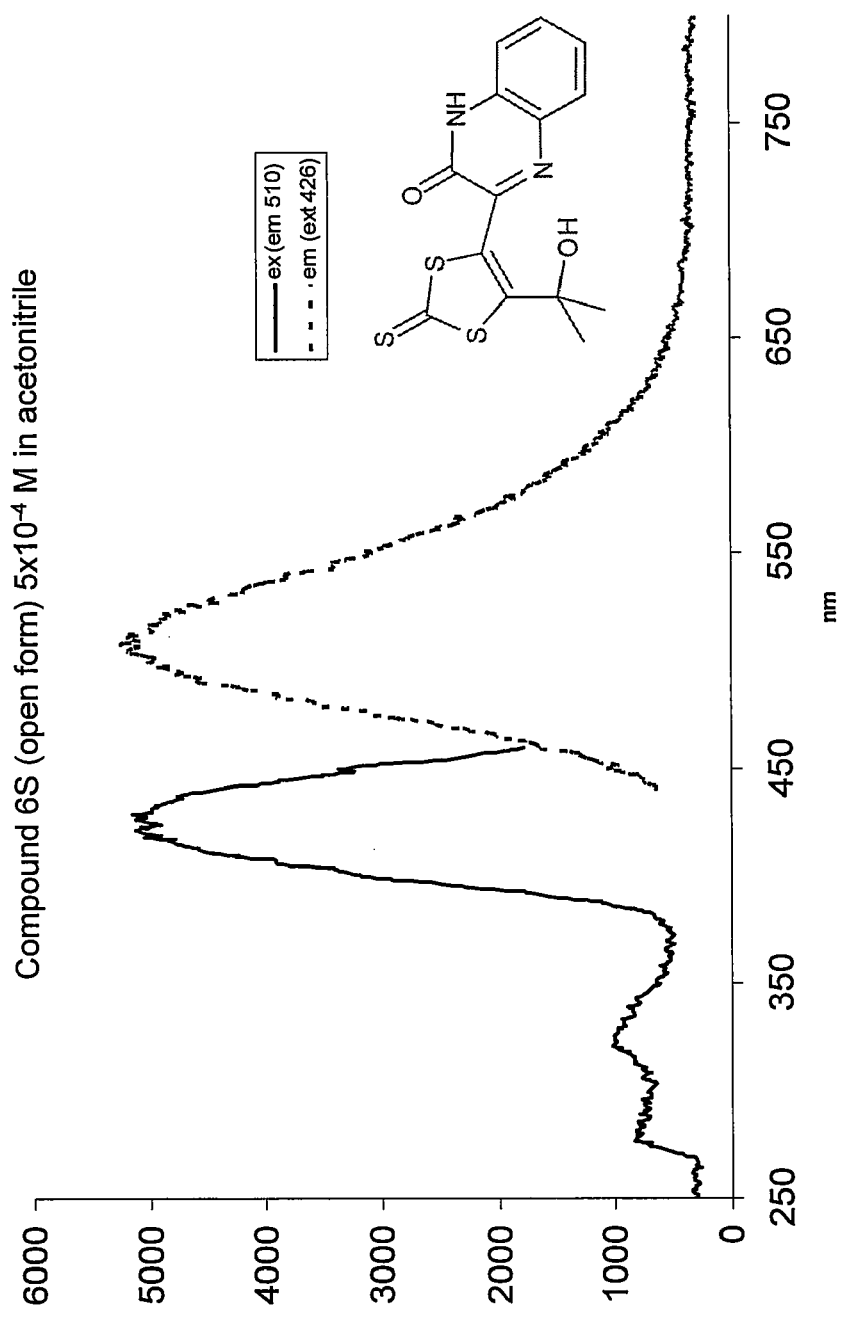

According to other embodiments, the fluorophores of the present disclosure may be used markers for metal ions, for example, to determine the presence of metal ions (such as a metal sensor). For example, under basic conditions, fluorescence of the fluorophores may be quenched when in the presence of certain transition metal ions. However, in the presence of other closed shell metal ions (such as, for example, $Zn^{2+}$, $Cd^{2+}$, $Hg^{2+}$, and $Pb^{2+}$) the fluorescence of the fluorophores may still be present. In certain embodiments, differential fluorescence wavelengths between complexes of the fluorophores and the metal ions can be used as sensors for such metal ions. For example, fluorophore 7 may be complexed with different metal ions and, depending on the type and charge of the metal ion, have a fluorescent emission of light with a different wavelength according to the complexed metal ion. As can be seen in FIG. 8, significant fluorescence is observed when fluorophore 7 is complexed with $Pb^{2+}$ ions, where the fluorescence is at a wavelength which is different from fluorescence wavelength observed from the other ions. In this example, the $Pb^+$/fluorophore complex fluoresces at a wavelength of ~470 nm, whereas the $Zn^{2+}$/fluorophore complex fluorescence shifts to a higher energy wavelength of ~606 nm after 24 hours of incubation. The structure of the complex of fluorophore 7 and the $Cu^{2+}$, $Ni^{2+}$, and $Mo^{4+}$ is shown in FIG. 11. In certain embodiments, the intensity of the fluorescent emission spectrum of the complex may be determined. According to specific embodiments, the fluorescent emission spectrum of the complex may be qualitatively used to determine the presence of a metal ion in a solution or, alternatively, may be quantitatively used (for example, by the intensity of the emission spectrum) to determine the concentration of the metal ion in the composition. For example, FIG. 12 shows how the intensity of fluorescence varies according to the concentration of the metal/fluorophore complex. Thus, the fluorophores of the present disclosure may be used as potential markers for metal ions.

The fluorophores according to certain embodiments of the present disclosure may be used as a component in an electronic device. For example, the fluorophores of the present disclosure may be used as an organic electronic material. In other embodiments, the fluorophores may be used in a molecular electronic device. For example, the fluorophores of the present disclosure may be used as a component in an LCD (liquid crystal display) screen or organic LED (light emitting diode), for example as a photostable fluorophore having a blue or bluish emission maximum. Non-limiting examples of the use of fluorophores as components of electronic devices are disclosed in PCT Publication No. WO/2004/051616, the disclosure of which is incorporated in its entirety by reference herein.

Figure 2:
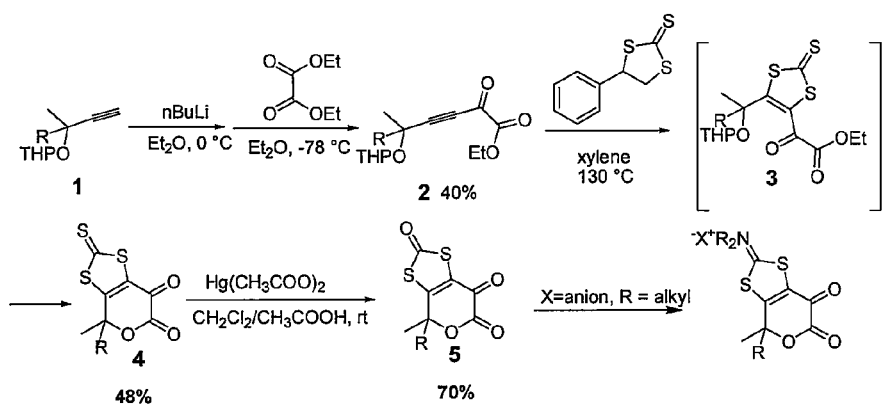
FIG. 2 illustrates a synthetic scheme for the synthesis of an intermediate for the preparation of the fluorophores according to the present disclosure.

According to various embodiments, the fluorophores of the present disclosure may be readily synthesized using organic chemistry techniques. For example, the synthesis of various embodiments of the fluorophores is described herein. It should be noted that the featured embodiments are intended to be exemplary and are in no way limiting to the scope of the fluorophores as described herein. Certain specific examples are discussed in detail in FIGS. 2 through 5, and similar methodologies can be used for synthesizing other fluorophores described herein. As illustrated in FIG. 2, the synthetic approach begins with the protection of the substituted propargyl alcohol with tetrahydropyran protecting group resulting in alkyne 1. The terminal alkyne in compound 1 is then deprotonated with n-butyl lithium and the reaction of the resulting acetylide with diethyl oxalate at a low temperature yields keto ester 2. The presence of an electron-withdrawing group (i.e., the ketone) activates the alkyne functionality toward the reaction with styrene trithiocarbonate to introduce the protected dithiolene moiety. When the reaction was performed neat, the open intermediate 3 was isolated and then transformed to the pyran-dione 4 upon addition of trifluoroacetic acid. Conversely, when the reaction was performed in xylene, the pyran-dione 4 was isolated directly. Next, the dithiolethione functionality may be converted to the dithiolone by treating compound 4 with mercuric acetate. The resulting dithiolone 5 can be converted to an imine or iminium ion, 5a or 5b respectively, by reacting the dithiolone with an appropriate amine. As will be understood by one having ordinary skill in the art, any of compounds 4, 5, 5a, or 5b may be converted to the fluorophore, thereby resulting in variations of X as shown in formula I.

Figure 3:
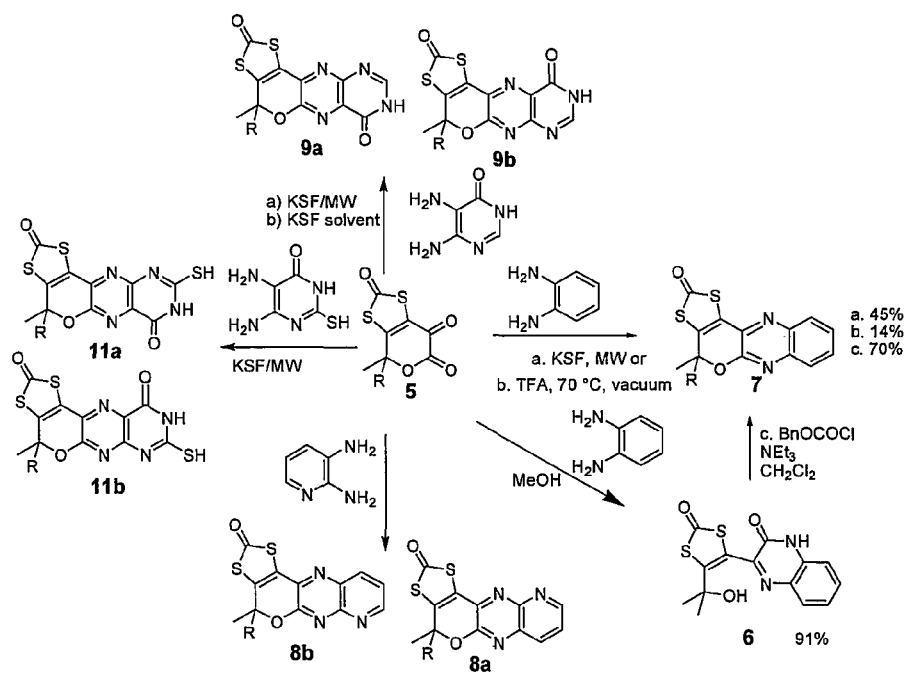
FIGS. 3 through 5 illustrate synthetic schemes for generating fluorophores possessing structurally distinct formulas according to various embodiments of the present disclosure.
Figure 4:
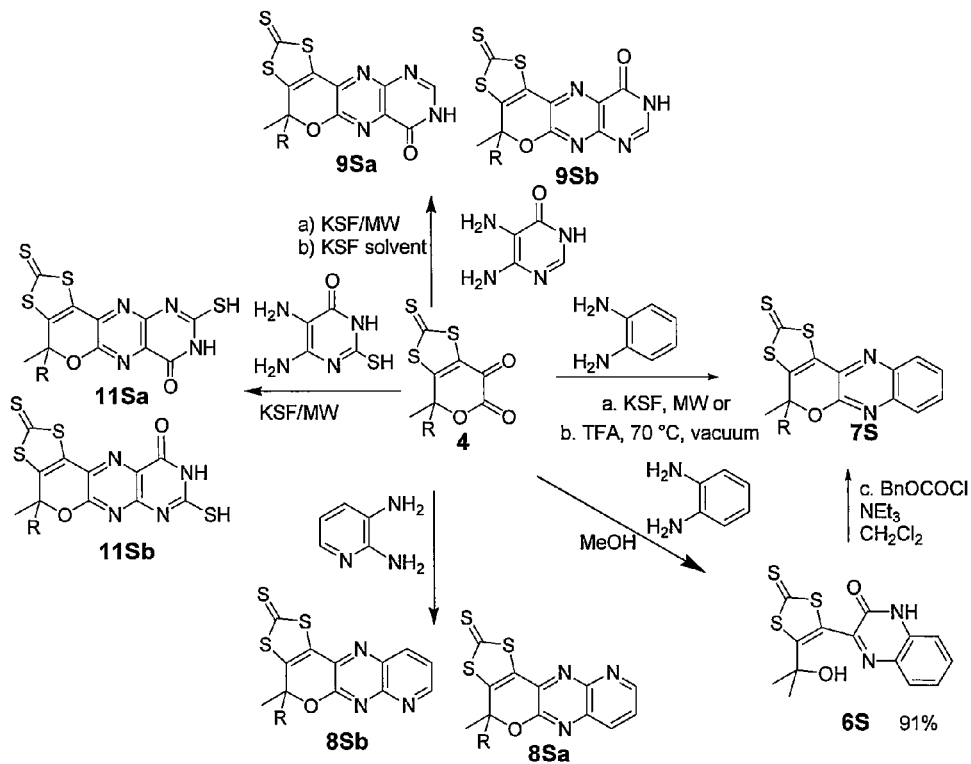
Figure 5:
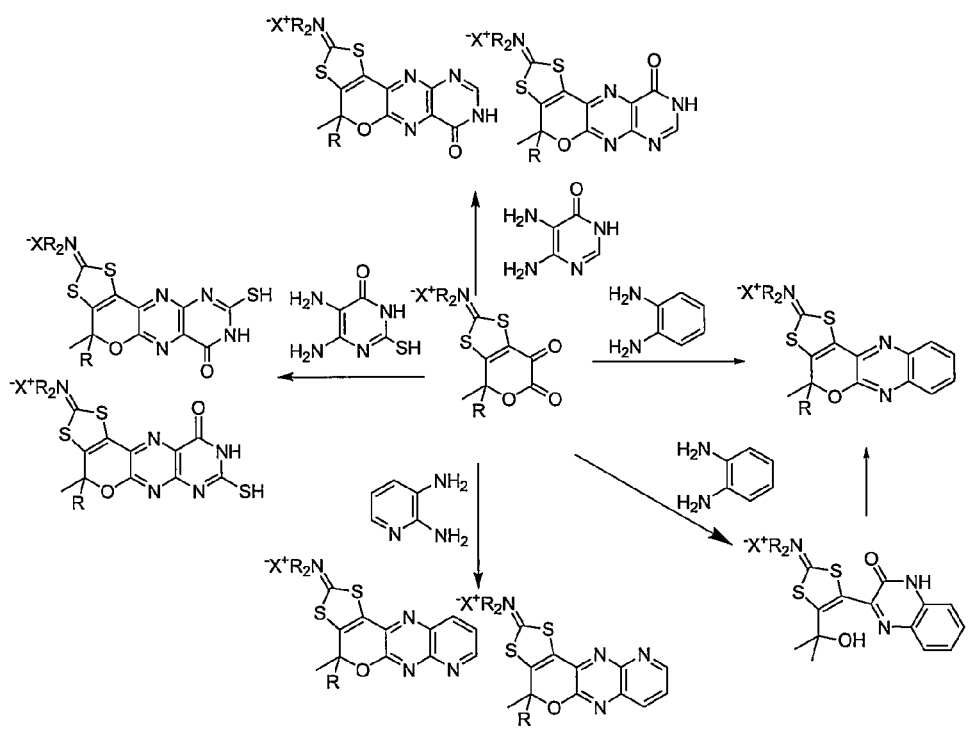

Once the diketo-compounds 4, 5, 5a, or 5b are prepared they may be reacted with a variety of diamines to produce different sets of compounds as desired. The condensation reactions resemble the Isay synthesis of pteridines reported by Isay, O., "Eine Synthese des Purins," *Berichte der deutschen Chemischen Gesellschaft.,* 1906, 39, 250-265, the disclosure of which is incorporated in its entirety by reference herein. The synthetic schemes for such reactions are shown in FIGS. 3-5. The structures of the resulting fluorophores have been confirmed by nuclear magnetic resonance spectroscopy and mass spectrometry, and certain fluorophore structures have been confirmed by X-ray crystallography.

Figure 7:
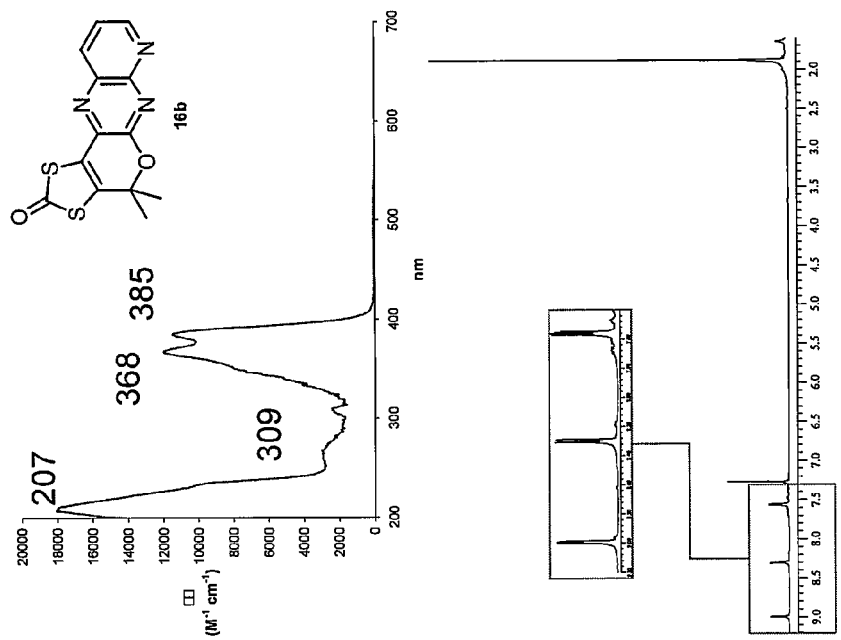
FIGS. 6 and 7 illustrate the electromagnetic absorption spectra and $^1$H NMR spectra of two embodiments of the present disclosure.
Figure 6:
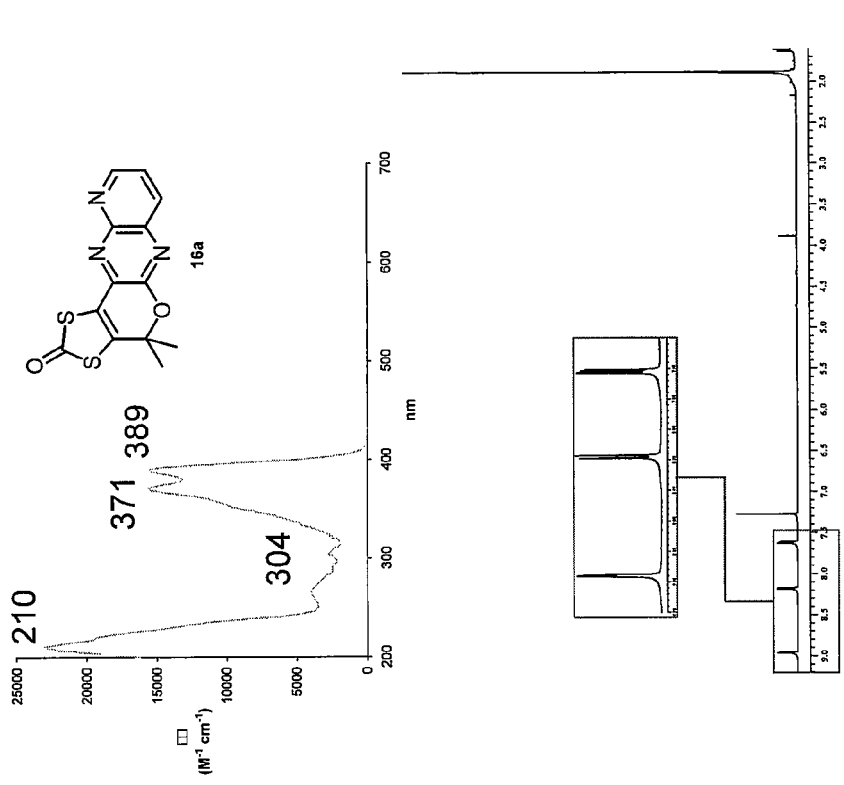

According to one embodiment, diketone 5 (R=methyl) may be condensed with 2,3-diamino pyridine using microwave irradiation ("MW") (equation 1). The resulting pair of isomeric fluorophores may be separated and exhibit different absorption spectrum. The absorption spectra and $^1$H NMR spectra of the two isomeric fluorophores are shown in FIGS. 6 and 7.

Eq. 1

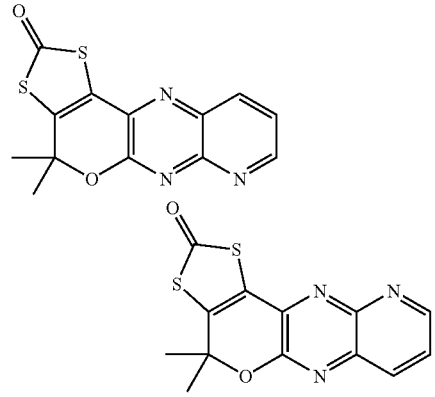

According to another embodiment, diketone 5 (R=ethyl) may be condensed with 5,6-diamino pyrimidone (R=H) using microwave irradiation ("MW") (equation 2). The resulting two isomeric fluorophores may be separated and exhibit different absorption and fluorescence spectra.

Eq. 2

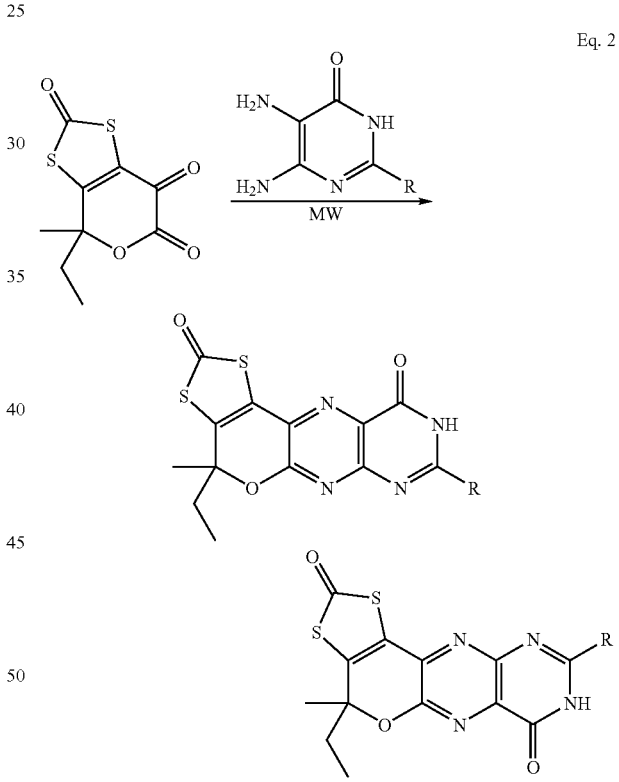

These fluorophores are soluble in common organic solvents, for example, but not limited to, chloroform, methylene chloride, acetonitrile, and methanol and in mixtures of methanol and water. They exhibit fluorescence properties, with the case of fluorophore 7 as an exemplary example. As shown in FIG. 9, the electronic spectrum of a methanolic solution of fluorophore 7 shows three strong absorption bands at 256 nm, 367 nm, and 385 nm, respectively. There is a shoulder near 330 nm and no transition was observed beyond 430 nm. The molar extinction coefficients of these bands are near 10000 or higher. Acetonitrile solutions of fluorophore 7 exhibit very similar spectral features with bands 208 nm, 255 nm, 365 nm, and 383 nm. The spectral features remain unchanged in a mixed solvent such as 2.5% methanol 97.5% water. Fluorophore 7 displays fluorescence, for example, solutions of fluorophore 7 produce blue florescence (that is, emit electromagnetic radiation having a wavelength in the blue region of the visible spectrum) when irradiated with a UV radiation. Fluorophore 7 is stable in acid while in base (i.e., pH>7) it transforms into a less fluorescent substance. Thus, in principle, this compound can be used as a pH sensor. That is, the fluorescence intensity may vary according to the pH of the environment or solution that the fluorophore is in.

Figure 10:
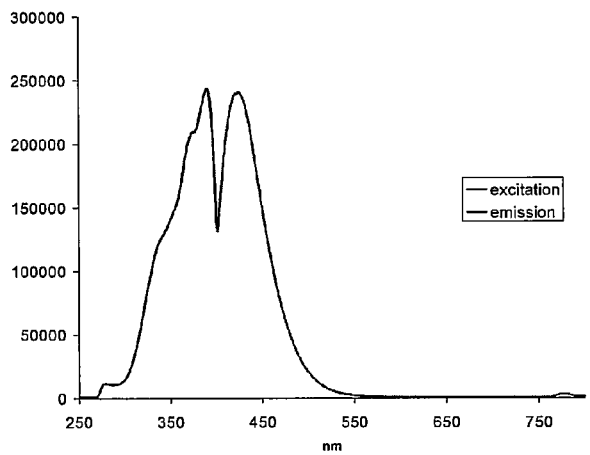
FIG. 10 illustrates the electromagnetic absorption/excitation spectrum and the fluorescence emission spectrum in a mixed solvent system of a fluorophore according to the present disclosure.

Fluorophore 7 exhibits strong fluorescence in acetonitrile as solvent, in methanol as solvent, and in the methanol-water mixed solvent. For an acetonitrile solution of fluorophore 7, when excited at 366 nm or 384 nm band, an emission at 411 nm is observed. Similarly when a methanolic solution of fluorophore 7 is excited at 385 nm or 367 nm, an emission at 415 nm is observed. Finally for a solution of fluorophore 7 in the mixed solvent, when excited at 389 nm, an emission is observed at 423 nm (see FIG. 10). A 0.12 value for the quantum yield of fluorophore 7 in methanol was determined using quinine sulfate as standard.

While various specific embodiments have been described in detail herein, the present disclosure is intended to cover various different combinations of the disclosed embodiments and is not limited to those specific embodiments described herein. Various embodiments of the present disclosure will be better understood when read in conjunction with the following non-limiting Examples. The procedures set forth in the Examples below are not intended to be limiting herein, as those skilled in the art will appreciate that various modifications to the procedures set forth in the Examples, as well as to other procedures not described in the Examples, may be useful in practicing the invention as described herein and set forth in the appended claims.

EXAMPLES

Example 1

3-Methyl-3-tetrahydropyranyloxy-butyne (compound 1) and 4-phenyl-1,3-dithiolane-thione were prepared according to P. G. Baraldi, et al., *Tetrahedron*, 45, 1989, 1517-1532 and C. C. J. Culvenor, et al., *J. Chem. Soc.*, 1946, 1050, the disclosures of each of which are incorporated in their entirety by reference herein. All reactions were conducted under an atmosphere of argon unless otherwise indicated. $CH_2Cl_2$ was distilled over $CaH_2$, $Et_2O$ over Na wire/benzophenone and methanol over Mg. All the other reagents and solvents were used without further purification. Column chromatography was performed on Silica gel 65×250 mesh (Sorbent Technologies).

$^1H$ NMR and $^{13}C$ NMR spectra were recorded at 500 and 125 MHz respectively, on a Varian Unity plus spectrometer. Proton peak positions were referenced to tetramethylsilane (TMS, set at $\delta$=0.00) in $CDCl_3$ and to the peak of residual non-deuterated solvent set at $\delta$=3.31 in $CD_3OD$. Carbon peak positions were referenced to the central peak of the solvent set at $\delta$=77.0 in $CDCl_3$, $\delta$=49.0 in $CD_3OD$. Infrared spectra were recorded on a Nicolet 380 FT-IR (Thermo) spectrometer. UV-vis spectra were obtained on a Perkin-Elmer Cary 300 spectrometer and on an Olis Cary-14 spectrophotometer in quartz cells (path length 10 mm). APCI mass spectra were recorded in methanol on a Waters ZMD mass spectrometer set in positive mode (solvent: methanol; cone voltage: 20 V; corona 2.7 kV; source temperature: 130 C; flow rate 100 μL/min) or negative mode (solvent: methanol; cone voltage: −20 V; corona 2.5 kV; source temperature: 130° C.; flow rate 100 μL/min). ESI-MS were recorded on a Waters ZMD mass spectrometer set in the negative ionization mode (solvent: methanol; cone voltage: 20 V; capillary voltage: 2.9 kV; source temperature: 130° C.; flow rate 150 μL/min). X-ray data collections were carried out on a Bruker Smart Apex II diffractometer, equipped with graphite-monochromator and Mo-Kα radiation ($\lambda$=0.71073 Å). Microwave reaction were performed under solvent-free conditions in the presence of the catalyst montmorillonite KSF) in a STAR System 2 (CEM Corporation) single mode microwave reactor.

Synthesis of Compound 2.

n-Butyl lithium (18 mL, of a 1.6 M solution in hexane, 28 mmol) was added to a solution of 3-methyl-3tetrahydropyranyloxy-butyne (3.3 g, 19 mmol) in $Et_2O$, previously cooled at 0° C. The resulting solution was stirred for 30 min at 0° C., then cooled to −78° C. and diethyl oxalate (4.3 mL, 29.4 mmol) was added. The reaction was followed by TLC (hexane/AcOEt 90:10). After ca. 2 h the reaction mixture was poured in a cold aqueous solution of $NH_4Cl$. The aqueous layer was extracted with of $Et_2O$ (3×25 mL). The organics were dried over $MgSO_4$, the solvent was removed under reduced pressure and the resulting pale yellow oil was purified by chromatography (silica gel, hexane/AcOEt 90:10) to give ethyl 5-methyl-2-oxo-5-(tetrahydro-2H-pyran-2-yloxy) hex-3-ynoate (2) as a pale yellow liquid. Yield: 2.04 g (40%). $^1H$-NMR spectrum in $CDCl_3$ (ppm): 5.10 (m, 1H), 4.38 (q, 2H), 4.36 (m, 2H), 3.96 (m, 2H), 3.54 (m, 2H), 1.85 (m, 2H), 1.75 (m, 2H), 1.64 (s, 3H), 1.59 (s, 3H), 1.40 (t, 3H). $^{13}C$-NMR spectrum in $CDCl_3$ (ppm): 169.3, 158.7, 101.4, 96.2, 81.6, 70.5, 63.1, 31.5, 29.2, 28.9, 25.2, 19.9, 13.8, 13.8. Selected IR (neat, cm$^-$): 2209, 1741, 1689. MS-APCI calculated for $C_{14}H_{20}O_5$ [M]$^-$ 268.13. found 267.96.

Synthesis of Compound 4.

Ethyl 5-methyl-2-oxo-5-(tetrahydro-2H-pyran-2-yloxy) hex-3-ynoate (2) (1.0 g, 3.7 mmol) and 4-phenyl-1,3-dithiolane-thione (2.0 g, 9.3 mmol) were dissolved in xylene (15 mL). The deep yellow solution was heated to 130° C. for ca. 4 h under Ar (the reaction was followed by TLC, eluent: $CH_2Cl_2$). The solvent was removed under reduced pressure and purification of the residue by chromatography (silica gel, $CH_2Cl_2$) provided 4,4-dimethyl-2-thioxo-4H-[1,3]dithiolo [4,5-c]pyran-6,7-dione (4) as a yellow solid. Yield: 0.44 g (48%). $^1H$-NMR spectrum in $CDCl_3$ (ppm): 1.88 (s, 6H). $^{13}C$-NMR spectrum in $CDCl_3$ (ppm): 205.3, 167.7, 162.6, 157.8, 153.6, 83.2, 31.9. Selected IR (neat, cm$^-$): 1747, 1681, 1557, 1460. MS-ESI calculated for $C_7H_8O_4S_2Na$ [M+Na]$^+$ 268.96. found 268.79.

Synthesis of Compound 5.

Mercury acetate (181 mg, 0.568 mmol) was added to a stirred solution of 4,4-dimethyl-2-thioxo-4H-[1,3]dithiolo[4,5-c]pyran-6,7-dione (6) (100 mg, 0.406 mmol) in $CH_2Cl_2$/AcOH (3:1). The reaction was followed by TLC (silica, $CH_2Cl_2$) and after ca. 30 min the mixture is filtered through a celite pad to remove the mercury salts. The resulting solution was washed first with water (3×15 mL) and then with sat. aqueous $NaHCO_3$ (5×10 mL), and dried over $MgSO_4$. Removal of the solvent under reduced pressure afforded pure 4,4-dimethyl-4H-[1,3]dithiolo[4,5-c]pyran-2,6,7-trione (5) a pale beige solid. Yield: 65 mg (70%). $^1H$-NMR spectrum in $CDCl_3$ (ppm): 1.88 (s, 6H). $^{13}C$-NMR spectrum in $CDCl_3$ (ppm): 184.5, 163.5, 160.4, 153.5, 128.3 84.2, 31.8. Selected IR (neat, cm$^{-1}$): 1746, 1693, 1641, 1552, 1453. MS-ESI calculated for $C_7H_8O_4S_2$ [M+H]$^+$ 230.98. found 230.78; calculated for $C_7H_8O_4S_2Na$ [M+Na]$^+$) 252.96. found 252.79.

Synthesis of Compound 6.

o-Phenylenediamine (50 mg, 0.22 mmol) was added to a stirred solution of 4,4-dimethyl-4H-[1,3]dithiolo[4,5-c]pyran-2,6,7-trione (5) (100 mg, 0.43 mmol) in methanol (15 mL). The solution was stirred overnight then the solvent was removed under reduced pressure and the residue was purified by crystallization from CHCl$_3$/hexane yielding pure 3-(5-(2-hydroxypropan-2-yl)-2-oxo-1,3-dithiol-4-yl)quinoxalin-2(1H)-one (6) as a light orange solid. Yield: 124.5 mg (91%). $^1$H-NMR spectrum in CDCl$_3$ (ppm): 10.40 (bs, 1H), 7.88 (d, 1H), 7.62 (t, 1H), 7.43 (d, 1H), 7.28 (t, 1H), 4.28 (s, 1H), 1.61 (s, 6H). $^1$H-NMR spectrum in CD$_3$OD (ppm): 7.82 (d, 1H), 7.60 (t, 1H), 7.39 (d, 1H), 7.36 (t, 1H), 1.52 (s, 6H). $^{13}$CNMR spectrum in CD$_3$OD (ppm): 194.6; 158.7; 156.0; 148.2; 136.0; 132.6; 127.9; 125.5; 123.6; 122.3; 119.2; 77.3; 33.8. Selected IR (neat, cm$^-$): 1667, 1598. MS-ESI calculated for C$_{14}$H$_{11}$N$_2$O$_3$S$_2$ [M–H]$^-$ 319.03. found 318.87. UV-vis in acetonitrile ($\lambda_{max}$, nm ($\epsilon$, M$^{-1}$ cm$^{-1}$)): 230 (19187), 283 (9295), 356 (21820).

Synthesis of Compound 7.

Method 1: 4,4-Dimethyl-4H-[1,3]dithiolo[4,5-c]pyran-2,6,7-trione (5) (80 mg, 0.347 mmol), o-phenylenediamine (40 mg, 0.347 mmol) and trifluoroacetic acid (70 µL) were mixed in a mortar until a homogeneous solid was obtained. The solid was heated to 70° C. in a vacuum oven for 18 h. The crude was purified by chromatography (silica gel, CH$_2$Cl$_2$). The first fraction collected was pure 4,4-Dimethyl-4H-5-oxa-1,3-dithia-6,11-diaza-cyclopenta[a]anthracen-2-one (7). Yield: 15 mg (14%). A second fraction was collected from the column using a mixture of CH$_2$Cl$_2$ and methanol (98:2) as solvent, which was identified as 3-(5-(2-hydroxypropan-2-yl)-2-oxo-1,3-dithiol-4-yl)quinoxalin-2(1H)-one (6). Yield: 25 mg (22%). $^1$H-NMR spectrum in CDCl$_3$ (ppm): 7.96 (d, 1H), 7.83 (d, 1H), 7.66 (t, 1H), 7.60 (t, 1H), 1.84 (s, 6H, Me). $^{13}$C-NMR spectrum in CDCl$_3$ (ppm): 189.0; 152.5; 141.0; 140.7; 139.6; 133.7; 130.5; 128.6; 128.1; 127.5; 124.2; 81.2; 30.0. Selected IR (neat, cm$^-$): 1705, 1664, 1624, 1461, 1409. MS-APCI calculated for C$_{14}$H$_{11}$N$_2$O$_2$S$_2$ [M+H]$^+$ 303.02. found 302.93. UV-vis in acetonitrile ($\lambda_{max}$, nm ($\epsilon$, M$^{-1}$ cm$^{-1}$)): 208 (19187), 255 (8543), 365 (10418), 383 (10244). UV-vis in methanol ($\lambda_{max}$, nm ($\epsilon$, M$^{-1}$ cm$^{-1}$)): 256 (10988), 367 (11194), 385 (9568).

Method 2: 4,4-Dimethyl-4H-[1,3]dithiolo[4,5-c]pyran-2,6,7-trione (5) (150 mg, 0.65 mmol), o-phenylenediamine (75 mg, 0.65 mmol) and montmorillonite KSF (100 mg) were mixed in a mortar until a homogeneous solid was obtained then the solid mixture was transferred into a test tube and irradiated with microwaves for 4 min. The resulting mixture was purified by chromatography (silica gel, CH$_2$Cl$_2$) to give pure 4,4-Dimethyl-4H-5-oxa-1,3-dithia-6,1,1-diaza-cyclopenta[a]anthracen-2-one (7). Yield: 90 mg (45%).

Method 3: 3-(5-(2-Hydroxypropan-2-yl)-2-oxo-1,3-dithiol-4-yl)quinoxalin-2(1H)-one (6) (130 mg, 0.405 mmol) was partially dissolved in CH$_2$Cl$_2$ (10 mL). Benzylchloroformate (125 µL, 0.81 mmol) and triethylammine (120 µL) were added and the resulting yellow solution was stirred overnight. The volume of the solution was reduced to ca. 3 mL and it was purified by chromatography (silica gel, CH$_2$Cl$_2$) to give pure 4,4-Dimethyl-4H-5-oxa-1,3-dithia-6,11-diaza-cyclopenta[a]anthracen-2-one (7). Yield: 82 mg (70%).

Example 2

Determination of Stoichiometry of Pb/Ligand Complex: In this Example, the relative intensity of the fluorescent emission of the Pb$^{2+}$/Ligand was determined at varying mole fraction of ligand.

A solution of ligand 4,4-Dimethyl-4H-5-oxa-1,3-dithia-6,11-diaza-cyclopenta[a]anthracen-2-one (7) in 2.5% methanol in water containing a 1:2 ratio of ligand to Et$_4$NOH was titrated with a solution of the metal salt (lead acetate) in 2.5% methanol in water. The mole fraction of the ligand in the solution was varied. The mixture of metal and ligand was incubated for an hour after addition to ensure complex formation and then the fluorescent emission spectrum intensity was measured and plotted against the mole fraction of ligand. The plot of the emission intensity vs. mole fraction of fluorophore is presented in FIG. 12. The maximum fluorescence intensity was observed at a mole fraction of 0.5 indicating a 1:1 complex. In addition, the intensity of the fluorescence was greater for the complex than for the uncomplexed ligand. Thus indicating that binding of the metal to the ligand could act as a sensor, showing the presence of metal ion in solution.

Although the invention has been described in detail in the foregoing embodiment for the purpose of illustration, it is to be understood that such detail is solely for that purpose and that variations can be made therein by those skilled in the art without departing from the spirit and scope of the invention.

We claim:

1. A compound having the formula:

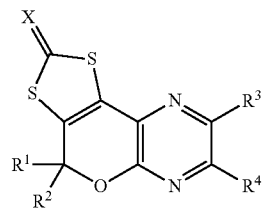

wherein
X is selected from the group consisting of O and S;
R$^1$ and R$^2$ are independently selected from the group consisting of hydrogen, C$_1$-C$_6$ alkyl, hydroxy C$_1$-C$_6$ alkyl, and phenyl; and
R$^3$ and R$^4$ come together to form one of a benzo ring, a heteroaryl ring, and a substituted heteroaryl ring, wherein the heteroaryl substituents are one or more of amino, C$_1$-C$_6$ alkyl, and amino C$_1$-C$_6$ alkyl.

2. The compound of claim 1, wherein R$^3$ and R$^4$ come together to form a benzo ring.

3. The compound of claim 1, wherein R$^3$ and R$^4$ come together to form a heteroaryl ring or substituted heteroaryl ring, the compound having the formula:

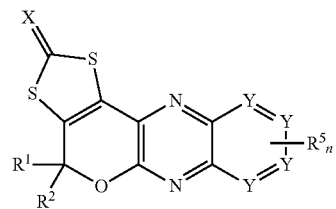

wherein Y is C or N, provided that at least one Y is N and n is an integer from 0 to 3 and R$^5$ is selected from the group consisting of amino, C$_1$-C$_6$ alkyl, and amino C$_1$-C$_6$ alkyl.

4. The compound of claim 1, wherein the compound fluoresces with an emission maximum at a wavelength from 300 nm to 600 nm.

5. The compound of claim 1, wherein the compound fluoresces with an emission maximum at a wavelength from 450 nm to 500 nm.

6. An electronic device comprising:
a compound having a formula

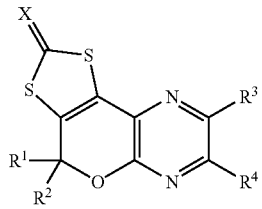

wherein

X is selected from the group consisting of O and S;

$R^1$ and $R^2$ are independently selected from the group consisting of hydrogen, $C_1$-$C_6$ alkyl, hydroxy $C_1$-$C_6$ alkyl, and phenyl; and $R^3$ and $R^4$ come together to form one of a benzo ring, a heteroaryl ring, and a substituted heteroaryl ring, wherein the heteroaryl substituents are one or more of amino, $C_1$-$C_6$ alkyl, and amino $C_1$-$C_6$ alkyl.

7. The electronic device of claim 6, wherein the device is selected from a liquid crystal display screen and an organic light emitting diode.

* * * * *